(12) United States Patent
Resconi et al.

(10) Patent No.: US 9,469,699 B2
(45) Date of Patent: Oct. 18, 2016

(54) CATALYSTS

(71) Applicant: BOREALIS AG, Vienna (AT)

(72) Inventors: Luigi Resconi, Ferrara (IT); Pascal Castro, Helsinki (FI); Ville Virkkunen, Helsinki (FI); Vyatcheslav V. Izmer, Moscow (RU); Dmitry S. Kononovich, Moscow (RU); Pavel Sergeevich Kulyabin, Moscow (RU); Alexander Z. Voskoboynikov, Moscow (RU)

(73) Assignee: BOREALIS AG, Vienna (AT)

( * ) Notice: Subject to any disclaimer, the term of this patent is extended or adjusted under 35 U.S.C. 154(b) by 0 days.

(21) Appl. No.: 14/654,409

(22) PCT Filed: Dec. 19, 2013

(86) PCT No.: PCT/EP2013/077335
§ 371 (c)(1),
(2) Date: Jun. 19, 2015

(87) PCT Pub. No.: WO2014/096164
PCT Pub. Date: Jun. 26, 2014

(65) Prior Publication Data
US 2016/0002369 A1 Jan. 7, 2016

(30) Foreign Application Priority Data
Dec. 21, 2012 (EP) .................................... 12199261

(51) Int. Cl.
*C07F 17/00* (2006.01)
*C08F 4/6592* (2006.01)
(Continued)

(52) U.S. Cl.
CPC ........... *C08F 4/65927* (2013.01); *C07C 1/321* (2013.01); *C07C 17/16* (2013.01); *C07C 45/00* (2013.01); *C07C 51/00* (2013.01);
(Continued)

(58) Field of Classification Search
CPC .............................. C07F 17/00; C08F 4/65917
See application file for complete search history.

(56) References Cited

U.S. PATENT DOCUMENTS 6,787,618 B1  9/2004  Winter et al.
7,405,261 B2  7/2008  Schulte et al.
(Continued)

FOREIGN PATENT DOCUMENTS

EP    0537686 A1    4/1993
EP    0776913 A2    6/1997
(Continued)

OTHER PUBLICATIONS

Deng, H. et al., Synthesis of High-Melting, Isotactic Polypropene with $C_2$-Symmetrical Zirconocenes, Macromol, 29, 6371-6376 (1996).
(Continued)

*Primary Examiner* — Caixia Lu
(74) *Attorney, Agent, or Firm* — Ballard Spahr LLP

(57) ABSTRACT

An asymmetric complex of formula (I)

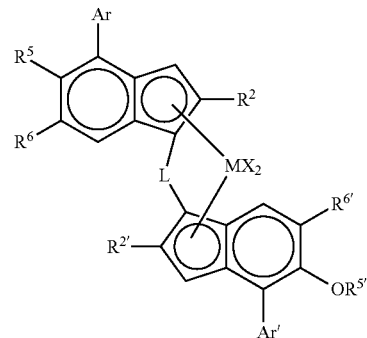

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl;
$R^2$ and $R^{2'}$ are each independently a $C_1$-$C_{20}$ hydrocarbyl radical;
$R^{5'}$ is a $C_{1-20}$ hydrocarbyl group;
$R^5$ is hydrogen, or a $C_{1-20}$ hydrocarbyl group;
$R^6$ is a non tertiary $C_{1-10}$ alkyl group or C6-10-aryl group or C7-10 arylalkyl group or $ZR^3$;
$R^{6'}$ is a tertiary $C_{4-20}$ alkyl group;
Z is O or S;
$R^3$ is a C1-20 hydrocarbyl group optionally substituted with halo;
Ar is an aryl or heteroaryl group having up to 20 carbon atoms optionally substituted by one or more groups $R^1$;
Ar' is an aryl or heteroaryl group having up to 20 carbon atoms optionally substituted by one or more groups $R^1$;
each $R^1$ is a $C_{1-20}$ hydrocarbyl group or two $R^1$ groups on adjacent carbon atoms taken together can form a fused 5 or 6 membered ring with the Ar group, said ring being itself optionally substituted with one or more groups $R^4$; and
each $R^4$ is a $C_{1-20}$ hydrocarbyl group.

14 Claims, No Drawings

(51) Int. Cl.

| | | |
|---|---|---|
| *C08F 210/06* | (2006.01) | |
| *C07F 7/08* | (2006.01) | |
| *C07C 1/32* | (2006.01) | |
| *C07C 17/16* | (2006.01) | |
| *C07C 45/00* | (2006.01) | |
| *C07C 51/00* | (2006.01) | |

(52) U.S. Cl.
CPC ............ *C07F 7/082* (2013.01); *C07F 7/0818* (2013.01); *C07F 17/00* (2013.01); *C08F 210/06* (2013.01)

(56) References Cited

U.S. PATENT DOCUMENTS

| | | |
|---|---|---|
| 2003/0149199 A1 | 8/2003 | Schottek et al. |
| 2004/0260107 A1 | 12/2004 | Oberhoff et al. |
| 2006/0252637 A1 | 11/2006 | Okumura |
| 2007/0135596 A1 | 6/2007 | Voskoboynikov et al. |
| 2009/0163643 A1 | 6/2009 | Kiss et al. |

FOREIGN PATENT DOCUMENTS

| | | | |
|---|---|---|---|
| EP | 1070729 | A2 | 1/2001 |
| EP | 1270614 | A2 | 1/2003 |
| EP | 1448578 | A1 | 8/2004 |
| EP | 1636245 | A1 | 3/2006 |
| EP | 1692144 | A2 | 8/2006 |
| EP | 2340649 | A1 | 7/2011 |
| EP | 2532687 | A2 | 12/2012 |
| EP | 2535372 | A1 | 12/2012 |
| WO | WO-01/48034 | | 7/2001 |
| WO | WO-02/02575 | | 1/2002 |
| WO | WO-02/02576 | | 1/2002 |
| WO | WO-03/045551 | | 6/2003 |
| WO | WO-03/051934 | A2 | 6/2003 |
| WO | WO-2004/106351 | A1 | 12/2004 |
| WO | WO-2005/023889 | A1 | 3/2005 |
| WO | WO-2005/105863 | A2 | 11/2005 |
| WO | WO-2007/107448 | A1 | 9/2007 |
| WO | WO-2007/116034 | A1 | 10/2007 |
| WO | WO-2007/135596 | A1 | 11/2007 |
| WO | WO-2009/054831 | A1 | 4/2009 |
| WO | WO-2009/054832 | A1 | 4/2009 |
| WO | WO-2009/054833 | A2 | 4/2009 |
| WO | WO-2011/076433 | A2 | 6/2011 |
| WO | WO-2011/076617 | A1 | 6/2011 |
| WO | WO-2014/096164 | A1 | 6/2014 |
| WO | WO-2014/096166 | A1 | 6/2014 |
| WO | WO-2014/096171 | A1 | 6/2014 |
| WO | WO-2014/096282 | A1 | 6/2014 |

OTHER PUBLICATIONS

Elder et al., Synthesis and Performance of *ansa*-Metallocene Catalysts with substituted Heterocyclic and Indenyl Ligands, Kinetics and Catalysis, vol. 47, No. 2, 2006, 192-197.

Ewen, J. et al., Chiral *Ansa* Metallocenes with Cp Ring-Fused to Thiophenes and Pyrroles: Syntheses, Crystal Structures, and Isotactic Polypropylene Catalysts, J. Am. Chem. Soc. 2001, 123, 4763-4773.

Ewen, J. et al., Evaluation of the dimethylsiyl-bis(2-methyl-4-phenyl-1-indenyl) ligand with group 4 triad metals in propene polymerizations with methylaluminoxane, Macromol. Rapid Commun. 19, 71-73 (1998).

Izmer, V. et al., Palladium-Catalyzed Pathways to Aryl-Substituted Indenes: Efficient Synthesis of Ligands and the Respective *ansa*-Zirconocenes, Organometallics 2006, vol. 25, No. 5, pp. 1217-1229.

Nifant'ev, Ilya E. et al., 5-Methoxy-Substituted Zirconium Bis-indenyl *ansa*-Complexes: Synthesis, Structure, and Catalytic Activity in the Polymerization and Copolymerization of Alkenes, Organometallics, vol. 31, No. 14, 4962-4970 (Jul. 23, 2012).

Nifant'ev, Ilya E. et al., Asymmetric *ansa*-Zirconocenes Containing a 2-Methyl-4-aryltetrahydroindacene Fragment: Synthesis, Structure, and Catalytic Activity in Propylene Polymerization and Copolymerization, Organometallics 2011, 30, 5744-5752.

Spaleck, W. et al., New Bridged zirconocenes for olefin polymerization: Binuclear and hybrid structures, Journal of Molecular Catalysis A: Chemical 128, 279-287 (1998).

Spaleck, W. et al., The Influence of Aromatic Substituents on the Polymerization Behavior of the Bridged Zirconocene Catalysts, Organometallics 1994, vol. 13, No. 3, 954-963.

International Search Report and Written Opinion mailed May 30, 2014 by the International Searching Authority for International Application No. PCT/EP2013/077344, which was published as WO 2014/096171 on Jun. 26, 2014 (Inventor—Castro et al.; Applicant—Borealis AG) (13 pages).

International Search Report and Written Opinion mailed May 27, 2014 by the International Searching Authority for International Application No. PCT/EP2013/077339, which was published as WO 2014/096166 on Jun. 26, 2014 (Inventor—Resconi et al.; Applicant—Borealis AG) (13 pages).

International Search Report and Written Opinion mailed May 30, 2014 by the International Searching Authority for International Application No. PCT/EP2013/077335, which was published as WO 2014/096164 on Jun. 26, 2014 (Inventor—Resconi, et al.; Applicant—Borealis AG) (15 pages).

International Search Report and Written Opinion mailed Mar. 3, 2014 by the International Searching Authority for International Application No. PCT/EP2013/077531, which was published as WO 2014/096282 on Jun. 26, 2014 (Inventor—Resconi, et al.; Applicant—Borealis AG) (10 pages).

U.S. Appl. No. 14/654,401, filed Jun. 19, 2015, Castro, P. et al.
U.S. Appl. No. 14/654,405, filed Jun. 19, 2015, Resconi, L. et al.
U.S. Appl. No. 14/654,413, filed Jun. 19, 2015, Resconi, L. et al.

CATALYSTS

CROSS-REFERENCE TO RELATED APPLICATIONS

This application is a U.S. National Phase Application of International Application No. PCT/EP2013/077335, filed on Dec. 19, 2013, which claims priority to European Patent Application No. 12199261.4, filed Dec. 21, 2012, each of which are hereby incorporated by reference in their entirety.

This invention relates to new asymmetrical bisindenyl complexes and catalysts comprising those complexes. The invention also relates to the use of the new bisindenyl metallocene catalysts for the production of polypropylene with high molecular weight at good activity levels.

Metallocene catalysts have been used to manufacture polyolefins for many years. Countless academic and patent publications describe the use of these catalysts in olefin polymerisation. Metallocenes are now used industrially and polyethylenes and polypropylenes in particular are often produced using cyclopentadienyl based catalyst systems with different substitution patterns.

The present inventors sought new metallocenes, which provide high molecular weight capability, especially in the case of propylene homopolymerisation and copolymerization between ethylene and propylene. In the case of existing catalysts, the copolymer molecular weight is often strongly reduced by ethylene incorporation or higher molecular weights are obtained at the expense of catalyst activity. In addition, the overall productivity of the existing catalysts still needs to be improved.

The present inventors have found a new class of asymmetric, chiral, racemic, anti, bridged bisindenyl metallocenes which are simple to synthesize despite their asymmetry and which are readily separable from their syn (meso-like) isomers. The two indenyl ligands are different from each other, that is, each indenyl ligand bears a set of substituents that are either chemically different, or located in different positions with respect to the other indenyl ligand. For the purpose of this invention, anti means that the two indenyl ligands are oriented in opposite directions with respect to the cyclopentadienyl-metal-cyclopentadienyl plane, while syn means that the two indenyl ligands are oriented in the same direction with respect to the cyclopentadienyl-metal-cyclopentadienyl plane.

They have high catalyst productivity and improved performance in the production of high molecular weight polypropylene homopolymers, and in the production of propylene copolymers. During copolymer manufacture, the metallocenes of the invention possess reduced chain transfer to ethylene, enabling the production of high molecular weight random and heterophasic copolymers.

The catalysts of the invention are new although similar catalysts are of course known in the art. The metallocene rac-Et(2,4,7-Me$_3$Ind)$_2$ZrCl$_2$/MAO is known. In U.S. Pat. No. 7,405,261, rac-Et[2,7-Me$_2$-4-(4-tBuPh)Ind]$_2$ZrCl$_2$ is reported to produce iPP with a melting temperature of 156° C., by polymerizing liquid propylene at 65° C.

WO2007/116034 describes various symmetrical complexes including ones based on 2-methyl-4-phenyl-5-methoxy-6-tertbutyl indenyl ligands.

WO2009/054831 describes zirconocenes with a 2-methyl-4,7-aryl substitution pattern, such as rac-Me$_2$Si[2-Me-4,7-(4-tBuPh)$_2$Ind]$_2$ZrCl$_2$. The melting temperatures of the homopolymers are still quite low, being in all cases below 150° C. despite the relatively low polymerization temperature of 65° C.

WO02/02576 describes conventionally supported metallocenes such as rac-Me$_2$Si[2-Me-4-(3,5-tBu$_2$Ph)Ind]$_2$ZrCl$_2$. These metallocene catalysts, activated with MAO or a borate, on a silica support, at a polymerisation temperature of 60 or 70° C., give iPP with Tm between 156 and 159° C.

The metallocene rac-9-silafluorenyl-9,9-[2-Me-4-(3,5-tBu$_2$Ph)Ind]$_2$ZrCl$_2$ also gives high melting temperature iPP and is described in WO02/02575.

The synthesis of 2-methyl-4-phenyl-6-isopropylindene and the corresponding C$_2$-symmetric zirconocene:

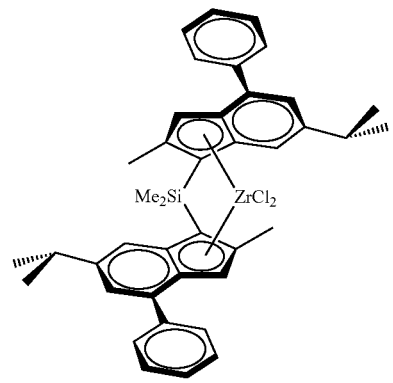

have been described in Basell patent EP 776913 and EP 1 270 614. The polymerization results, however, indicate that this metallocene has no remarkable difference compared to its analogues without the 6-isopropyl substituent. Voskoboynikov and co-workers (US patent application US 2007/0135596 and Organometallics 2006, 25, 1217-1229) have reported the synthesis of the same metallocene, but its polymerization performance has not been reported.

All the above examples are based on C$_2$-symmetric metallocenes, that is those in which both indenyl ligands are identically substituted. The present invention however, is concerned with asymmetrical ligand structures.

There are also several examples of isoselective bisindenyl metallocenes having C$_1$-symmetry, that is metallocene complexes in which the two bridged indenyl ligands have different substitution pattern.

Spaleck et al. in Journal of Molecular Catalysis A: Chemical 128, 1998, 279-287 describes some bisindenyl catalysts which are asymmetric but which lack any substituents on the 6 or 7 position of the 6-membered ring. These complexes, although of relative simple structure, have a quite poor performance in propylene polymerization.

In WO2005/105863 and WO2004/106531, various asymmetric catalysts are disclosed which have a branched alkyl group at the 2-position of the ring. Such catalysts have poor activity. WO2001/048034 also requires branched structures at the 2-position of the metallocenes therein.

WO2004/106351 describes ligands carrying 2-methyl-4-aryl-6-methyl substituents. The metallocene anti-dimethylsilandiyl(2,6-dimethyl-4-(4'-tert-butylphenyl)indenyl)(2-isopropyl-4-(4'-tert-butylphenyl)indenyl)zirconium dichloride is described in Basell patent application WO2005-023889 where it is used to polymerize propylene in liquid phase, followed by a gas phase copolymerization step. Polymerization activities are quite low.

EP-A-1692144 describes asymmetrical catalysts based on tricyclic rings.

The present inventors seek alternative asymmetrical catalysts that can allow the formation of interesting polypropylene polymers and copolymers at high catalyst activities. Also, in all the above cases, the preparation of the indenes require multistep syntheses which render the ligands quite expensive.

Our invention concerns the use of asymmetrical metallocenes, especially the anti-isomers thereof, bearing as Π-ligands two indenyls which are different in their substitution pattern while still being relatively simple to synthesize. In particular we have now discovered that by using a suitable combination of indenyl ligands, preferably where both indenes are 2-alkyl substituted, and by using particular catalyst formulation technology, isotactic polypropylene with melting temperature close or above 150° C. can be produced with very high productivities and having high molecular weights.

The metallocenes of the present invention are bridged bisindenyl complexes having C1-symmetry, that is the two indenyl ligands have different substitution patterns, where one of the indenyls bears a non tertiary alkyl group in position 6. The other ligand carries an alkoxy type ligand at the 5-position and a tertiary ligand at the 6-position.

These metallocenes have surprisingly been found to possess higher activities than previously reported asymmetric catalysts.

SUMMARY OF INVENTION

Thus, viewed from one aspect the invention provides an asymmetric complex of formula (I)

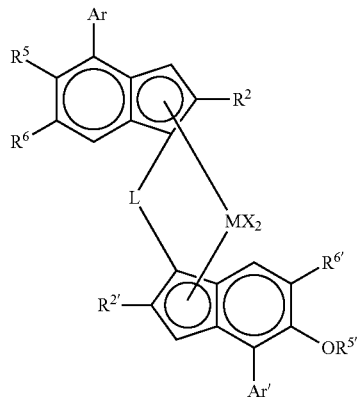

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl;
$R^2$ and $R^{2'}$ are each independently a $C_1$-$C_{20}$ hydrocarbyl radical;
$R^{5'}$ is a $C_{1-20}$ hydrocarbyl group;
$R^5$ is hydrogen, or a $C_{1-20}$ hydrocarbyl group;
$R^6$ is a non tertiary $C_{1-10}$ alkyl group or C6-10-aryl group or C7-10 arylalkyl group or $ZR^3$;
Z is O or S;
$R^{6'}$ is a tertiary $C_{4-20}$ alkyl group;
$R^3$ is a C1-20 hydrocarbyl group optionally substituted with halo;

Ar is an aryl or heteroaryl group having up to 20 carbon atoms optionally substituted by one or more groups $R^1$;
Ar' is an aryl or heteroaryl group having up to 20 carbon atoms optionally substituted by one or more groups $R^1$;
each $R^1$ is a $C_{1-20}$ hydrocarbyl group or two $R^1$ groups on adjacent carbon atoms taken together can form a fused 5 or 6 membered ring with the Ar group, said ring being itself optionally substituted with one or more groups $R^4$; and
each $R^4$ is a $C_{1-20}$ hydrocarbyl group.

Viewed from another aspect the invention provides a catalyst comprising (i) an asymmetric complex of formula (I)

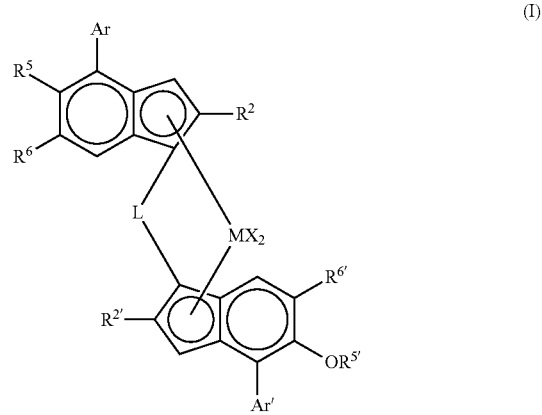

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl;
$R^2$ and $R^{2'}$ are each independently a $C_1$-$C_{20}$ hydrocarbyl radical;
$R^{5'}$ is a $C_{1-20}$ hydrocarbyl group;
$R^5$ is hydrogen, or a $C_{1-20}$ hydrocarbyl group;
$R^6$ is a non tertiary $C_{1-10}$ alkyl group or C6-10-aryl group or C7-10 arylalkyl group or $ZR^3$;
Z is O or S;
$R^{6'}$ is a tertiary $C_{4-20}$ alkyl group;
$R^3$ is a C1-20 hydrocarbyl group optionally substituted with halo.

Ar is an aryl or heteroaryl group having up to 20 carbon atoms optionally substituted by one or more groups $R^1$;
Ar' is an aryl or heteroaryl group having up to 20 carbon atoms optionally substituted by one or more groups $R^1$;
each $R^1$ is a $C_{1-20}$ hydrocarbyl group or two $R^1$ groups on adjacent carbon atoms taken together can form a fused 5 or 6 membered ring with the Ar group, said ring being itself optionally substituted with one or more groups $R^4$; and
each $R^4$ is a $C_{1-20}$ hydrocarbyl group;
and (ii) a cocatalyst comprising a compound of a group 13 metal, e.g. Al or boron.

The catalyst of the invention can be used in non-supported form or in solid form. The catalyst of the invention may be used as a homogeneous catalyst or heterogeneous catalyst.

The catalyst of the invention in solid form, preferably in solid particulate form, can be either supported on an external carrier material, like silica or alumina, or, in a particularly preferred embodiment, is free from an external carrier, however still being in solid form. For example, the solid catalyst is obtainable by a process in which (a) a liquid/liquid emulsion system is formed, said liquid/liquid emulsion system comprising a solution of the catalyst components (i) and (ii) dispersed in a solvent so as to form dispersed droplets; and (b) solid particles are formed by solidifying said dispersed droplets.

Viewed from another aspect the invention provides a process for the manufacture of a catalyst as hereinbefore defined comprising obtaining a complex of formula (I) and a cocatalyst as hereinbefore described;

forming a liquid/liquid emulsion system, which comprises a solution of catalyst components (i) and (ii) dispersed in a solvent, and solidifying said dispersed droplets to form solid particles.

Viewed from another aspect the invention provides the use in olefin polymerisation of a catalyst as hereinbefore defined, especially for the formation of a polyolefin, especially a polyethylene or polypropylene, such as a polypropylene homopolymer or copolymer.

Viewed from another aspect the invention provides a process for the polymerisation of at least one olefin comprising reacting said at least one olefin with a catalyst as hereinbefore described, especially for the formation of polypropylene.

DEFINITIONS

Throughout the description the following definitions are employed.

By free from an external carrier is meant that the catalyst does not contain an external support, such as an inorganic support, for example, silica or alumina, or an organic polymeric support material.

The term asymmetric means that the top and bottom ligands in the catalyst cannot be the same.

The term $C_{1-20}$ hydrocarbyl group therefore includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or of course mixtures of these groups such as cycloalkyl substituted by alkyl. Linear and branched hydrocarbyl groups cannot contain cyclic units. Aliphatic hydrocarbyl groups cannot contain aryl rings.

Unless otherwise stated, preferred $C_{1-20}$ hydrocarbyl groups are $C_{1-20}$ alkyl, $C_{4-20}$ cycloalkyl, $C_{5-20}$ cycloalkylalkyl groups, $C_{7-20}$ alkylaryl groups, $C_{7-20}$ arylalkyl groups or $C_{6-20}$ aryl groups, especially $C_{1-10}$ alkyl groups, $C_{6-10}$ aryl groups, or $C_{7-12}$ arylalkyl groups, e.g. $C_{1-8}$ alkyl groups. Most especially preferred hydrocarbyl groups are methyl, ethyl, propyl, isopropyl, tertbutyl, isobutyl, $C_{5-6}$-cycloalkyl, cyclohexylmethyl, phenyl or benzyl.

The term halo includes fluoro, chloro, bromo and iodo groups, especially chloro groups, when relating to the complex definition.

The oxidation state of the metal ion is governed primarily by the nature of the metal ion in question and the stability of the individual oxidation states of each metal ion.

It will be appreciated that in the complexes of the invention, the metal ion M is coordinated by ligands X so as to satisfy the valency of the metal ion and to fill its available coordination sites. The nature of these σ-ligands can vary greatly.

Catalyst activity is defined in this application to be the amount of polymer produced (kg)/g catalyst/h. Catalyst metal activity is defined here to be the amount of polymer produced (kg)/g Metal/h. The term productivity is also sometimes used to indicate the catalyst activity although herein it designates the amount of polymer produced per unit weight of catalyst.

A tertiary substituent herein is one comprising a carbon atom carrying three non H groups such as tert butyl. A non tertiary substituent means the group is free from any carbons carrying three non H groups.

DETAILED DESCRIPTION OF INVENTION

The complexes of the invention are asymmetrical. That means simply that the two indenyl ligands forming the metallocene are different, that is, each indenyl ligand bears a set of substituents that are either chemically different, or located in different positions with respect to the other indenyl ligand. More precisely, they are chiral, racemic bridged bisindenyl metallocenes. Whilst the complexes of the invention may be in their syn configuration ideally, they are in their anti configuration. For the purpose of this invention, racemic-anti means that the two indenyl ligands are oriented in opposite directions with respect to the cyclopentadienyl-metal-cyclopentadienyl plane, while racemic-syn means that the two indenyl ligands are oriented in the same direction with respect to the cyclopentadienyl-metal-cyclopentadienyl plane, as shown in the Figure below.

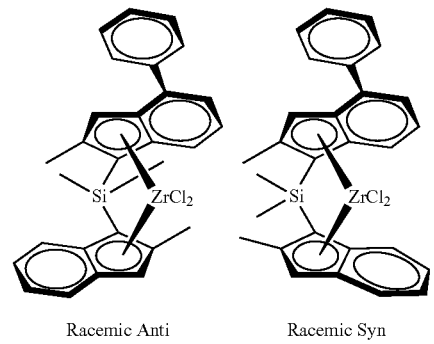

Racemic Anti　　　　　　Racemic Syn

Formula (I) is intended to cover both syn and anti configurations, preferably anti.

In fact, the metallocenes of the invention are $C_1$-symmetric; the anti isomers however maintain a pseudo-$C_2$-symmetry since they maintain $C_2$-symmetry in close proximity of the metal center, although not at the ligand periphery. As will be seen, the use of two different indenyl ligands as described in this invention allows for a much finer structural variation, hence a more precise tuning of the catalyst performance, compared to the typical $C_2$-symmetric catalysts. By nature of their chemistry, both anti and syn enantiomer pairs are formed during the synthesis of the complexes. However, by using the ligands of this invention, separation of the preferred anti isomers from the syn isomers is straightforward.

It is preferred if the metallocenes of the invention are employed as the rac anti isomer. Ideally therefore at least 95% mol, such as at least 98% mol, especially at least 99% mol of the metallocene is in the racemic anti isomeric form.

In the catalysts of the invention:

M is preferably Zr.

Each X, which may be the same or different, is preferably a hydrogen atom, a halogen atom, a R, OR, $OSO_2CF_3$, OCOR, SR, $NR_2$ or $PR_2$ group wherein R is a linear or branched, cyclic or acyclic, $C_{1-20}$ alkyl, $C_{2-20}$ alkenyl, $C_{2-20}$ alkynyl, $C_{6-20}$ aryl, $C_{7-20}$ alkylaryl or $C_{7-20}$ arylalkyl radical; optionally containing heteroatoms belonging to groups 14-16. R is preferably a $C_{1-6}$ alkyl, phenyl or benzyl group.

Most preferably each X is independently a hydrogen atom, a halogen atom, $C_{1-6}$ alkoxy group or an R group, e.g. preferably a $C_{1-6}$ alkyl, phenyl or benzyl group. Most preferably X is chlorine or a methyl radical. Preferably both X groups are the same.

L is preferably an alkylene linker or a bridge comprising a heteroatom, such as silicon or germanium, e.g. —$SiR^8{}_2$—, wherein each $R^8$ is independently $C_{1-20}$ alkyl, $C_{3-10}$ cycloakyl, $C_{6-20}$ aryl or tri($C_{1-20}$ alkyl)silyl, such as trimethylsilyl. More preferably $R^8$ is $C_{1-6}$ alkyl, especially methyl or $C_{3-7}$ cycloalkyl, such as cyclohexyl. Most preferably, L is a dimethylsilyl or a methylcyclohexylsilyl bridge (i.e. Me-Si-cyclohexyl). It may also be an ethylene bridge.

$R^2$ and $R^{2'}$ can be different but they are preferably the same. $R^2$ and $R^{2'}$ are preferably a $C_{1-10}$ hydrocarbyl group such as $C_{1-6}$ hydrocarbyl group. More preferably it is a linear or branched $C_{1-10}$ alkyl group. More preferably it is a linear or branched $C_{1-6}$ alkyl group, especially linear $C_{1-6}$ alkyl group such as methyl or ethyl.

The two Ar groups Ar and Ar' can be the same or different. It is preferred however if the Ar groups are different. The Ar' group may be unsubstituted. The Ar' group is preferably a $C_{6-20}$ aryl group such as a phenyl group or naphthyl group, preferably phenyl. The Ar' group can also be a heteroaryl group, such as carbazolyl. The Ar' is preferably a phenyl based group optionally substituted by groups $R^1$, e.g. a unsubstituted phenyl group or mono or disubstituted phenyl group especially in position 4 of the aryl ring bound to the indenyl ligand or in the 3,5-positions.

The Ar group is preferably a $C_{6-20}$ aryl group such as a phenyl group or naphthyl group, preferably phenyl. The Ar group can also be a heteroaryl group, such as carbazolyl. The Ar group can be unsubstituted or substituted by one or more groups $R^1$, more preferably by one or two $R^1$ groups, especially in position 4 of the aryl ring bound to the indenyl ligand or in the 3,5-positions.

In one embodiment Ar' is unsubstituted and Ar is substituted by one or two groups $R^1$. Alternatively, both Ar' and Ar are substituted.

$R^1$ is preferably a $C_{1-20}$ hydrocarbyl group, such as a $C_{1-20}$ alkyl group. $R^1$ groups can be the same or different, preferably the same. More preferably, $R^1$ is a $C_{2-10}$ alkyl group such as $C_{3-8}$ alkyl group. Highly preferred groups are tert butyl or isopropyl groups. It is preferred if the group $R^1$ is bulky, i.e. is branched. Branching might be alpha or beta to the ring. Branched $C_{3-8}$ alkyl groups are also favoured therefore. It is preferred if $R^1$ groups on the same ring are the same.

In a further embodiment, two $R^1$ groups on adjacent carbon atoms taken together can form a fused 5 or 6 membered non aromatic ring with the Ar group, said ring being itself optionally substituted with one or more groups $R^4$. Such a ring might form a tetrahydroindenyl group with the Ar/Ar' ring or a tetrahydronaphthyl group.

If an $R^4$ group is present, there is preferably only 1 such group. It is preferably a $C_{1-10}$ alkyl group.

It is preferred if there is one or two $R^1$ groups present on the Ar/Ar' group. Where there is one $R^1$ group present, the group is preferably para to the indenyl ring (4-position). Where two $R^1$ groups are present these are preferably at the 3 and 5 positions.

$R^5$ is preferably H or a $C_{1-10}$ alkyl group, such as methyl but most preferably it is H.

$R^{5'}$ is preferably a $C_{1-10}$ alkyl group, e.g. C1-6 alkyl group, such as linear C1-6 alkyl group especially methyl, or a $C_{7-20}$ arylalkyl, such as benzyl, or a $C_{7-20}$ alkylaryl group, such as 2,4,6-trimethylphenyl.

$R^{6'}$ is preferably a tertiary C4-10 alkyl group such as a tertbutyl group. It is preferred if $R^{6'}$ is branched alpha or beta to the ring, preferably alpha to the ring. Branched $C_{4-8}$ alkyl groups are favoured therefore.

$R^6$ is preferably a non tertiary $C_{1-10}$ alkyl group or C6-10-aryl group or C7-10 arylalkyl group such as 2,4,6-trimethylphenyl, or $ZR^3$. More preferably, $R^6$ is a $C_{1-10}$ alkyl group such as $C_{1-6}$ alkyl group. Highly preferred groups are isopropyl, ethyl and methyl. The $R^6$ group is ideally linear.

Z is O or S, preferably O.

$R^3$ is preferably a $C_{1-10}$ hydrocarbyl group, especially a $C_{1-10}$ alkyl group, or aryl group optionally substituted by one or more alkyl or halo groups. Most especially $R^3$ is a $C_{1-6}$ alkyl group, such as a linear $C_{1-6}$ alkyl group, e.g. methyl or ethyl, or a $C_{7-20}$ arylalkyl, such as benzyl, or a $C_{7-20}$ alkylaryl group, such as 2,4,6-trimethylphenyl.

Thus, preferred complexes of the invention are of formula (II)

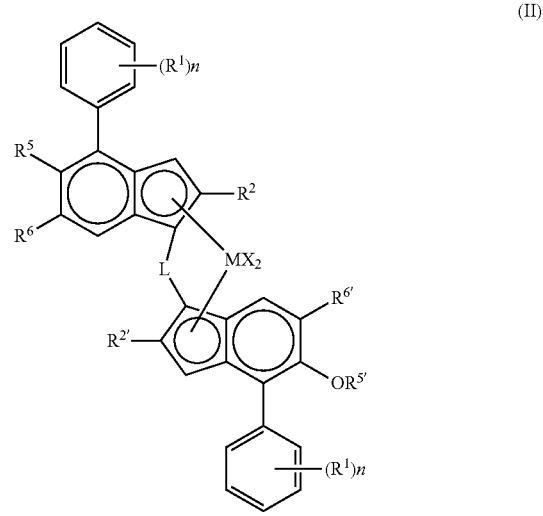

wherein

M is zirconium or hafnium;

each X is a sigma ligand, preferably each X is independently a hydrogen atom, a halogen atom, $C_{1-6}$ alkoxy group, $C_{1-6}$ alkyl, phenyl or benzyl group;

L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, $C_{1-20}$ alkyl, $C_{3-10}$ cycloalkyl, tri($C_{1-20}$-alkyl)silyl, $C_{6-20}$-aryl, $C_{7-20}$ arylalkyl or $C_{7-20}$ alkylaryl;

$R^2$ and $R^{2'}$ are each independently a $C_1$-$C_{10}$ alkyl radical;

$R^{5'}$ is a $C_{1-6}$ alkyl group;

$R^5$ is hydrogen, or a $C_{1-10}$ alkyl group;

$R^6$ is a non tertiary $C_{1-6}$ alkyl, C6-10 aryl group or C7-10 arylalkyl group;

$R^{6'}$ is a tertiary $C_{4-10}$ alkyl group;

each n is independently 0 to 3, e.g. 0, 1 or 2;

and each $R^1$ is independently a $C_{1-10}$ alkyl group.

Viewed from another aspect the invention provides a complex of formula (III):

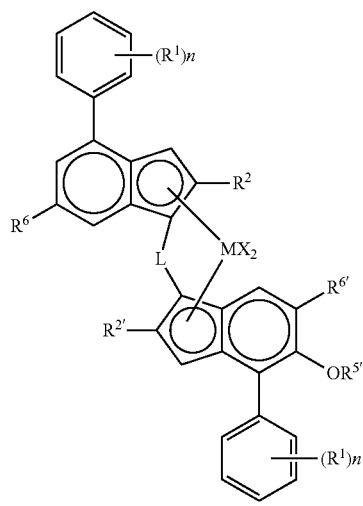

M is zirconium or hafnium;

each X is a sigma ligand, preferably each X is independently a hydrogen atom, a halogen atom, $C_{1-6}$ alkoxy group, $C_{1-6}$ alkyl, phenyl or benzyl group;

L is a divalent bridge selected from —R'$_2$C— or —R'$_2$Si— wherein each R' is independently a hydrogen atom, $C_{1-20}$ alkyl or $C_{3-10}$ cycloalkyl;

$R^2$ and $R^{2'}$ are each independently a $C_{1-6}$ alkyl radical;

$R^{5'}$ is a $C_{1-6}$ alkyl group;

$R^6$ is a non tertiary $C_{1-6}$ alkyl;

$R^{6'}$ is a tertiary $C_{4-8}$ alkyl group;

each n is independently 0 to 3, e.g. 0, 1 or 2;

and each $R^1$ is independently a $C_{1-10}$ alkyl group.

Viewed from a further preferred aspect the invention provides a complex of formula (IV):

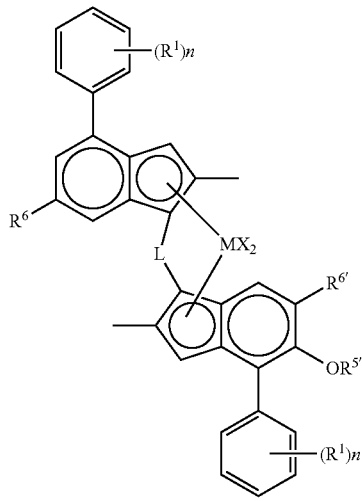

M is zirconium or hafnium;

each X is a sigma ligand, preferably each X is independently a hydrogen atom, a halogen atom, $C_{1-6}$-alkoxy group, $C_{1-6}$-alkyl, phenyl or benzyl group;

L is a divalent bridge selected from —R'$_2$C— or —R'$_2$Si— wherein each R' is independently a hydrogen atom, $C_{1-20}$ alkyl or $C_{3-10}$ cycloalkyl;

$R^{5'}$ is a $C_{1-6}$ alkyl group;

$R^6$ is a $C_{1-3}$ alkyl;

$R^{6'}$ is a tertiary $C_{4-8}$ alkyl group;

each n is independently 0 to 2;

and each $R^1$ is independently a $C_{3-8}$ alkyl group.

Most especially, the complex of the invention is of formula (V):

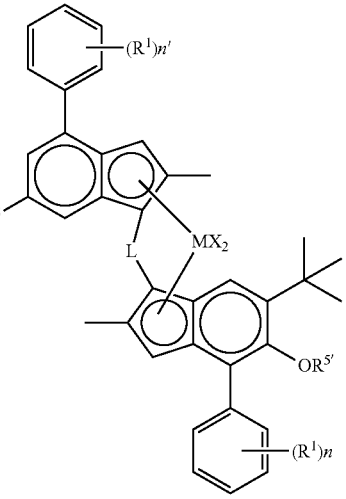

wherein each X is a sigma ligand, preferably each X is independently a hydrogen atom, a halogen atom, $C_{1-6}$-alkoxy group, $C_{1-6}$-alkyl, phenyl or benzyl group;

L is -Me$_2$Si—;

$R^{5'}$ is a $C_{1-6}$ alkyl group;

$R^6$ is a $C_{1-3}$ alkyl;

n' is 1 to 2;

n is 0 to 2;

and each $R^1$ is independently a $C_{3-8}$ alkyl group.

Particular ligand combinations of interest are shown in the following table.

TABLE 1

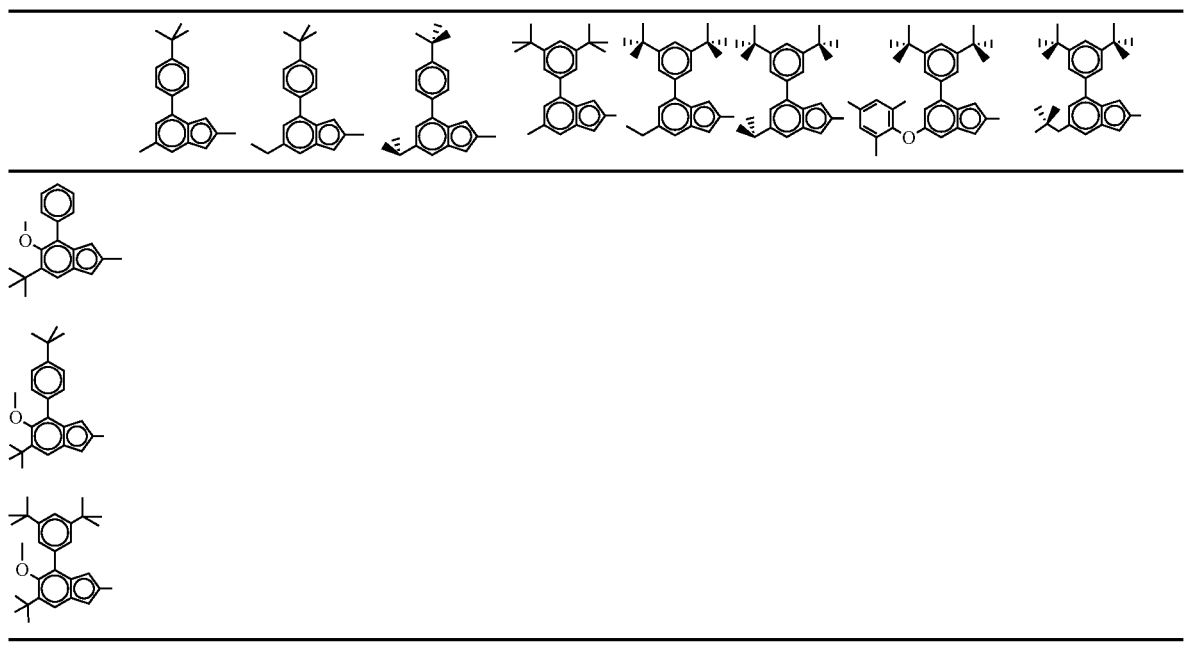

These ligands can be bridged at the 1-position using a linker L as hereinbefore defined and complexed using $MX_2$ groups as hereinbefore defined. Particular compounds of the invention include the following (or their Hf analogues):

TABLE 2

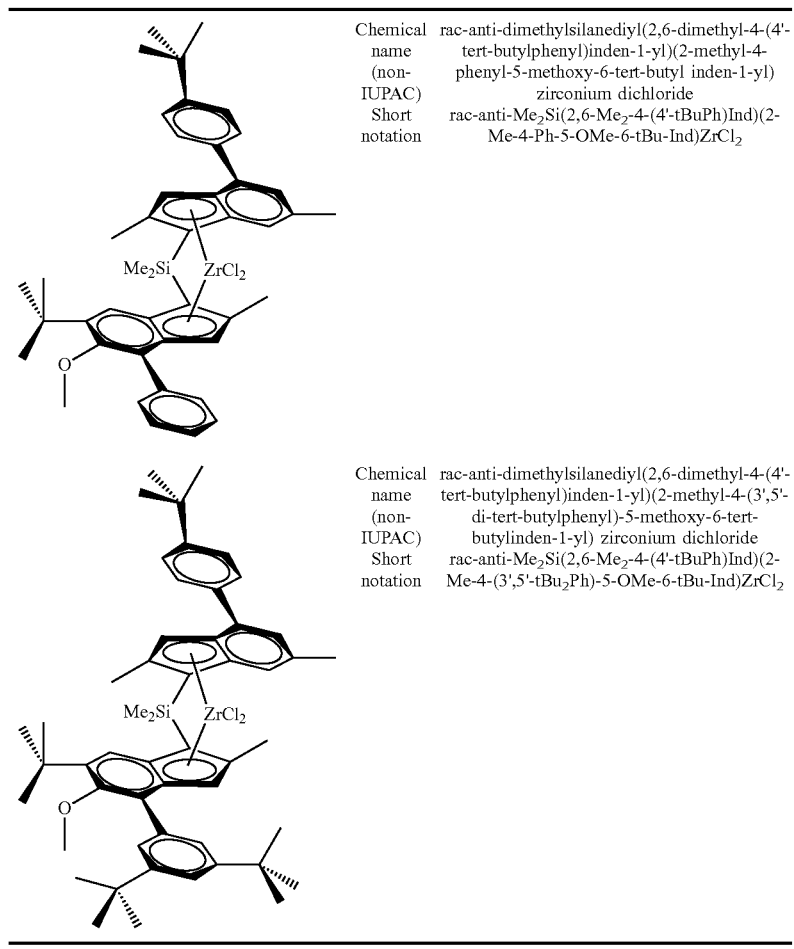

Chemical name (non-IUPAC): rac-anti-dimethylsilanediyl(2,6-dimethyl-4-(4'-tert-butylphenyl)inden-1-yl)(2-methyl-4-phenyl-5-methoxy-6-tert-butyl inden-1-yl) zirconium dichloride
Short notation: rac-anti-Me$_2$Si(2,6-Me$_2$-4-(4'-tBuPh)Ind)(2-Me-4-Ph-5-OMe-6-tBu-Ind)ZrCl$_2$ Chemical name (non-IUPAC): rac-anti-dimethylsilanediyl(2,6-dimethyl-4-(4'-tert-butylphenyl)inden-1-yl)(2-methyl-4-(3',5'-di-tert-butylphenyl)-5-methoxy-6-tert-butylinden-1-yl) zirconium dichloride
Short notation: rac-anti-Me$_2$Si(2,6-Me$_2$-4-(4'-tBuPh)Ind)(2-Me-4-(3',5'-tBu$_2$Ph)-5-OMe-6-tBu-Ind)ZrCl$_2$ For the avoidance of doubt, any narrower definition of a substituent offered above can be combined with any other broad or narrowed definition of any other substituent.

Throughout the disclosure above, where a narrower definition of a substituent is presented, that narrower definition is deemed disclosed in conjunction with all broader and narrower definitions of other substituents in the application.

Synthesis

The ligands required to form the complexes and hence catalysts of the invention can be synthesised by any process and the skilled organic chemist would be able to devise various synthetic protocols for the manufacture of the necessary ligand materials.

For example, the following general synthetic scheme can be used:

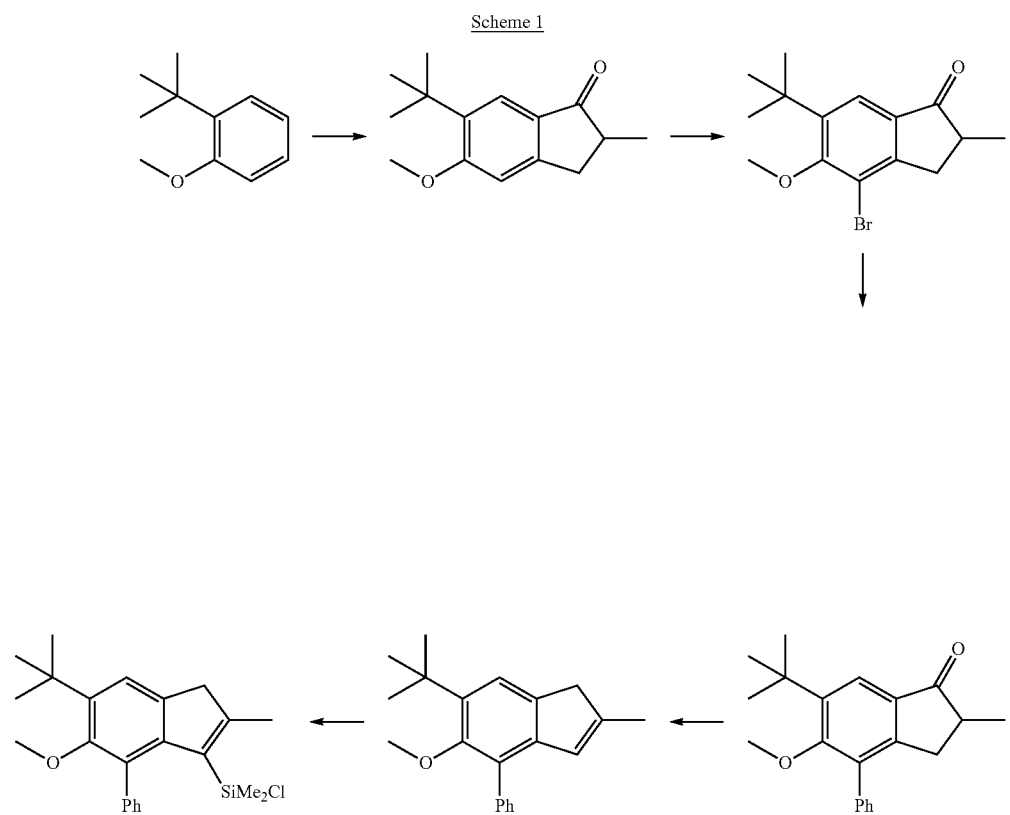

Suitable reagents for this transformation are given in the examples section. Whilst this scheme refers to specific compounds, the general principles displayed here apply to the metallocenes of the invention. The important point to remember is that as the ligands are asymmetric, a conventional reaction with $SiMe_2Cl_2$ cannot be effected to bridge two ligands as that leads to symmetrical products. Instead, each ligand has to be attached to the bridge stepwise with control over the reaction stoichiometry.

This invention also provides an improved method for the production of 2,6-dimethyl-4-bromoindanone, which is a common key intermediate for the synthesis of the complexes of the present invention. This is shown in reaction scheme 2:

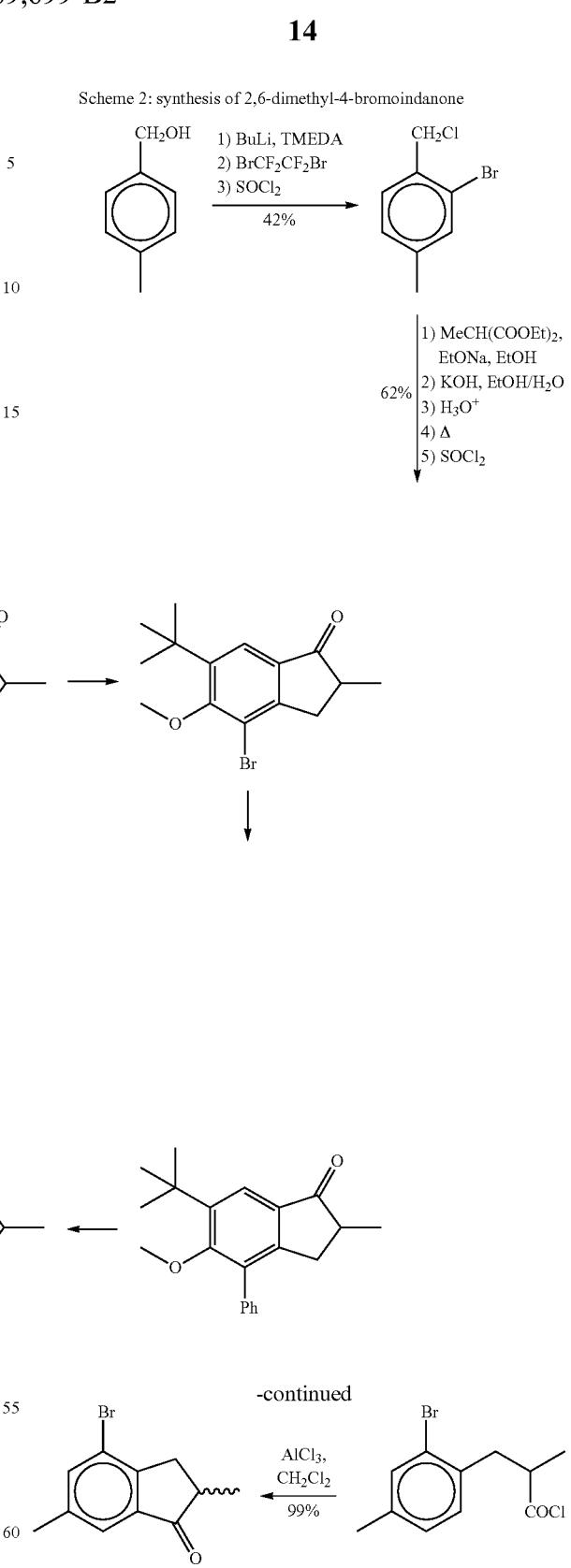

The first step of scheme 2 actually consists of three reactions, i.e.:

(a) ortho-lithiation of benzyl alcohol by n-BuLi in the presence of TMEDA giving the aryllithium compound (the yield of this ortho-lithiation can be considerably improved during the optimization work):

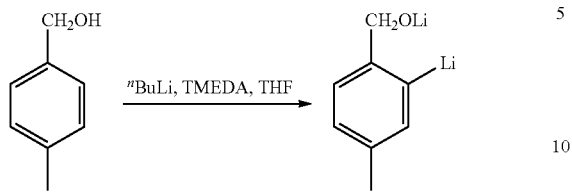

(b) substitution of Li with Br by reaction with 1,2-dibromoperfluoroethane. This reaction gives perfluoroethylene, LiBr and the following aryl bromide (similar reactions usually go in 80-100% yield):

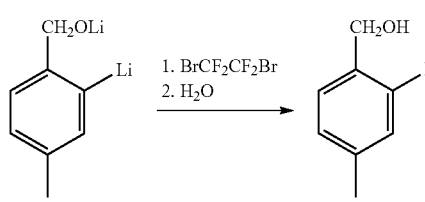

(c) substitution of OH function with Cl by treatment of alcohol with thionyl chloride (common transformation which usually goes in 100% yield).

Traditionally, the regioselective preparation of bromoarenes has been accomplished either by using electrophilic bromination or by using sequence metallation-bromination of appropriate arenes with various reagents (Br$_2$, NBS, C$_2$Br$_2$F$_4$ or 1,2-dibromoethane). Usage the C$_2$Br$_2$F$_4$[(1)] as a source of Br+ in a sequence of lithiation and bromination is preferable in many aspects. In this example we used ortho-lithiation of benzyl alcohol using C$_2$Br$_2$F$_4$ as electrophile. The yield of the desired product can be increased either by choosing the optimal conditions in this scheme, or by changing the order of stages, for example, by using 4-methylbenzaldehyde for metallation-bromination.

The bromoindanone is then converted to the indene of choice in very high yields, as shown in Scheme 3 for the case of 2,6-dimethyl-4-(4'-tert-butylphenyl)indene:

Scheme 3: synthesis of 2,6-dimethyl-4-(4'-tert-butylphenyl)indene

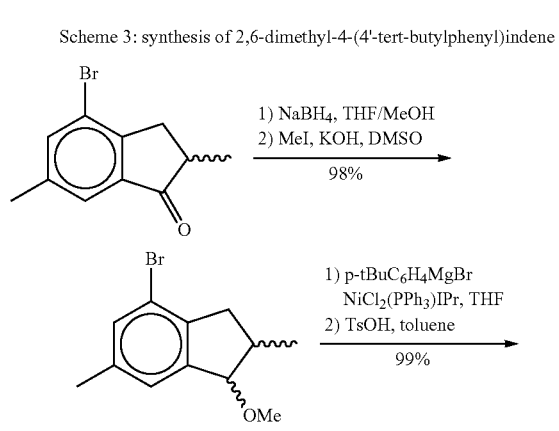

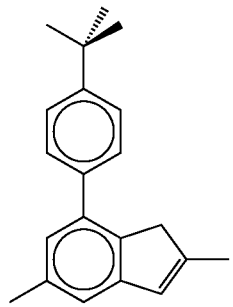

Viewed from another aspect the invention therefore provides a process involving the following transformations:

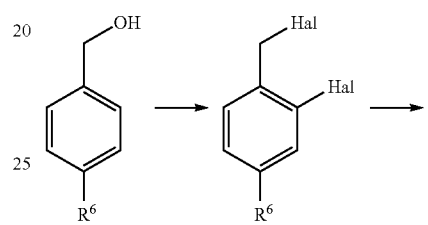

wherein Hal is halide, R$^6$, and Ar is as defined in formula (I); especially:

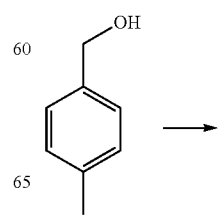

-continued

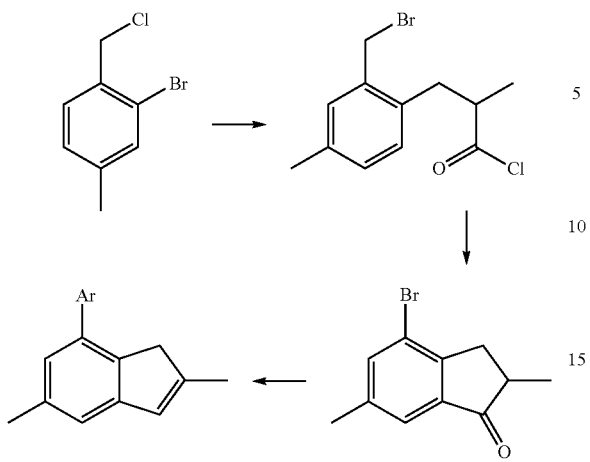

The reagents needed to effect this transfer are given in the schemes above. In particular, the first step involves ortho-lithiation of benzyl alcohol by BuLi, e.g. in the presence of TMEDA (tetramethylethylenediamine). Substitution of the Li with 1,2-dibromoperfluoroethane is preferred to add the Br to the molecule. Conversion of OH to Cl can be carried out conventionally, e.g. using thionyl chloride.

The crucial reaction therefore in this sequence forms a further aspect of the invention, in particular a process involving the following transformations:

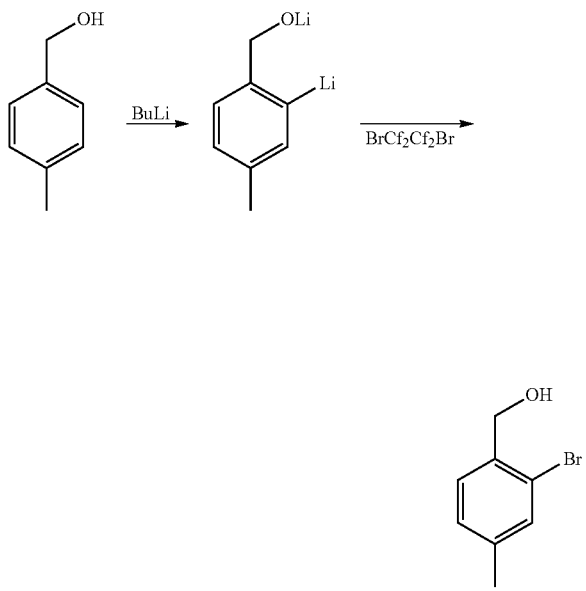

It will be appreciated that the methyl group shown above may be any $R^6$ substituent as herein defined.

Intermediates

Whilst the invention primarily relates to catalysts, it will be appreciated that the complexes of the invention and the ligands used to form those complexes are also new. The invention further relates therefore to complexes of formula (I) to (V) from which the $MX_2$ coordination has been removed and the proton returned to the indenyl.

Ligands of interest are therefore of formula (I')

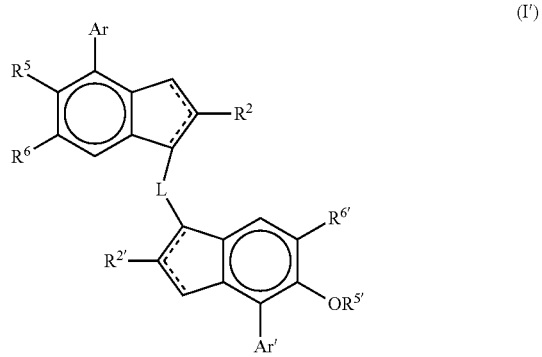

(I')

wherein the substituents are as hereinbefore defined and the dotted lines represent a double bond present in between carbons 1 and 2 or 2 and 3 of the indenyl ring. It will be appreciated therefore that this molecule contains double bond isomers. By double bond isomers is meant the compounds where the double bond is positioned between the 2 and 3 atoms rather than 1 and 2 atoms of the bicyclic ring. It may be that more than one double bond isomer is present in a sample. Preferred ligands are analogues of the complexes described above from which $MX_2$ coordination has been removed and the proton returned to the indenyl.

Cocatalyst

To form an active catalytic species it is normally necessary to employ a cocatalyst as is well known in the art. Cocatalysts comprising one or more compounds of Group 13 metals, like organoaluminium compounds or borates used to activate metallocene catalysts are suitable for use in this invention.

The olefin polymerisation catalyst system of the invention comprises (i) a complex in which the metal ion is coordinated by a ligand of the invention; and normally (ii) an aluminium alkyl compound (or other appropriate cocatalyst), or the reaction product thereof. Thus the cocatalyst is preferably an alumoxane, like MAO or an alumoxane other than MAO.

Borate cocatalysts can also be employed. It will be appreciated by the skilled man that where boron based cocatalysts are employed, it is normal to preactivate the complex by reaction thereof with an aluminium alkyl compound, such as TIBA. This procedure is well known and any suitable aluminium alkyl, e.g. $Al(C_{1-6}\text{-alkyl})_3$, can be used.

Boron based cocatalysts of interest include those of formula $$BY_3$$

wherein Y is the same or different and is a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine. Preferred examples for Y are methyl, propyl, isopropyl, isobutyl or trifluoromethyl, unsaturated groups such as aryl or haloaryl like phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl) phenyl. Preferred options are trifluoroborane, triphenylborane, tris(4-fluorophenyl)borane, tris(3,5-difluorophenyl)borane, tris(4-fluoromethylphenyl)borane, tris(2,4, 6-trifluorophenyl)borane, tris(penta-fluorophenyl)borane, tris(tolyl)borane, tris(3,5-dimethyl-phenyl)borane, tris(3,5-difluorophenyl)borane and/or tris(3,4,5-trifluorophenyl)borane.

Particular preference is given to tris(pentafluorophenyl) borane.

It is preferred however if borates are used, i.e. compounds containing a borate anion. Such ionic cocatalysts preferably contain a non-coordinating anion such as tetrakis(pentafluorophenyl)borate and tetraphenylborate. Suitable counterions are protonated amine or aniline derivatives such as methylammonium, anilinium, dimethylammonium, diethylammonium, N-methylanilinium, diphenylammonium, N,N-dimethylanilinium, trimethylammonium, triethylammonium, tri-n-butylammonium, methyldiphenylammonium, pyridinium, p-bromo-N,N-dimethylanilinium or p-nitro-N,N-dimethylanilinium. Preferred ionic compounds which can be used according to the present invention include: triethylammoniumtetra(phenyl)borate, tributylammoniumtetra(phenyl)borate, trimethylammoniumtetra(tolyl)borate, tributylammoniumtetra(tolyl)borate, tributylammoniumtetra (pentafluorophenyl)borate, tripropylammoniumtetra (dimethylphenyl)borate, tributylammoniumtetra (trifluoromethylphenyl)borate, tributylammoniumtetra(4-fluorophenyl)borate, N,N-dimethylcyclohexylammoniumtetrakis(pentafluorophenyl) borate, N,N-dimethylbenzylammoniumtetrakis (pentafluorophenyl)borate, N,N-dimethylaniliniumtetra (phenyl)borate, N,N-diethylaniliniumtetra(phenyl)borate, N,N-dimethylaniliniumtetrakis(pentafluorophenyl)borate, N,N-di(propyl)ammoniumtetrakis(pentafluorophenyl)borate, di(cyclohexyl)ammoniumtetrakist(pentafluorophenyl) borate, triphenylphosphoniumtetrakis(phenyl)borate, triethylphosphoniumtetrakis(phenyl)borate, diphenylphosphoniumtetrakis(phenyl)borate, tri(methylphenyl)phosphoniumtetrakis(phenyl)borate, tri(dimethylphenyl)phosphoniumtetrakis(phenyl)borate, triphenylcarbeniumtetrakis(pentafluorophenyl)borate, or ferroceniumtetrakis (pentafluorophenyl)borate. Preference is given to triphenylcarbeniumtetrakis(pentafluorophenyl)borate, N,N-dimethylcyclohexylammoniumtetrakis(pentafluorophenyl) borate or N,N-dimethylbenzylammoniumtetrakis(pentafluorophenyl)borate.

The use of $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4^{2-}$ is especially preferred.

Suitable amounts of cocatalyst will be well known to the skilled man.

Catalyst Manufacture

The metallocene complex of the present invention can be used in combination with a suitable cocatalyst as a catalyst for the polymerization of olefins, e.g. in a solvent such as toluene or an aliphatic hydrocarbon, (i.e. for polymerization in solution), as it is well known in the art. Preferably, polymerization of olefins, especially propylene, takes place in the condensed phase or in gas phase.

The catalyst of the invention can be used in supported or unsupported form. The particulate support material used is preferably an organic or inorganic material, such as silica, alumina or zirconia or a mixed oxide such as silica-alumina, in particular silica, alumina or silica-alumina. The use of a silica support is preferred. The skilled man is aware of the procedures required to support a metallocene catalyst.

Especially preferably the support is a porous material so that the complex may be loaded into the pores of the support, e.g. using a process analogous to those described in WO94/14856 (Mobil), WO95/12622 (Borealis) and WO2006/097497. The particle size is not critical but is preferably in the range 5 to 200 μm, more preferably 20 to 80 μm. The use of these supports is routine in the art.

In an alternative embodiment, no support is used at all. Such a catalyst can be prepared in solution, for example in an aromatic solvent like toluene, by contacting the metallocene (as a solid or as a solution) with the cocatalyst, for example methylaluminoxane or a borane or a borate salt previously dissolved in an aromatic solvent, or can be prepared by sequentially adding the dissolved catalyst components to the polymerization medium. In a preferred embodiment, the metallocene (when X differs from alkyl or hydrogen) is prereacted with an aluminum alkyl, in a ratio metal/aluminum of from 1:1 up to 1:500, preferably from 1:1 up to 1:250, and then combined with a solution of the borane or borate cocatalyst dissolved in an aromatic solvent, either in a separate vessel or directly into the polymerization reactor. Preferred metal/boron ratios are between 1:1 and 1:100, more preferably 1:1 to 1:10.

In one particularly preferred embodiment, no external carrier is used but the catalyst is still presented in solid particulate form. Thus no external support material such as inert organic or inorganic carrier, such as for example silica as described above is employed.

In order to provide the catalyst of the invention in solid form but without using an external carrier, it is preferred if a liquid/liquid emulsion system is used. The process involves forming dispersing catalyst components (i) and (ii) in a solvent, and solidifying said dispersed droplets to form solid particles.

In particular, the method involves preparing a solution of one or more catalyst components; dispersing said solution in an solvent to form an emulsion in which said one or more catalyst components are present in the droplets of the dispersed phase; immobilising the catalyst components in the dispersed droplets, in the absence of an external particulate porous support, to form solid particles comprising the said catalyst, and optionally recovering said particles.

This process enables the manufacture of active catalyst particles with improved morphology, e.g. with a predetermined spherical shape, surface properties and particle size and without using any added external porous support material, such as an inorganic oxide, e.g. silica. By the term "preparing a solution of one or more catalyst components" is meant that the catalyst forming compounds may be combined in one solution which is dispersed to the immiscible solvent, or, alternatively, at least two separate catalyst solutions for each part of the catalyst forming compounds may be prepared, which are then dispersed successively to the solvent.

In a preferred method for forming the catalyst at least two separate solutions for each or part of said catalyst may be prepared, which are then dispersed successively to the immiscible solvent.

More preferably, a solution of the complex comprising the transition metal compound and the cocatalyst is combined with the solvent to form an emulsion wherein that inert solvent forms the continuous liquid phase and the solution comprising the catalyst components forms the dispersed phase (discontinuous phase) in the form of dispersed droplets. The droplets are then solidified to form solid catalyst particles, and the solid particles are separated from the liquid and optionally washed and/or dried. The solvent forming the continuous phase may be immiscible to the catalyst solution at least at the conditions (e.g. temperatures) used during the dispersing step.

The term "immiscible with the catalyst solution" means that the solvent (continuous phase) is fully immiscible or partly immiscible i.e. not fully miscible with the dispersed phase solution.

Preferably said solvent is inert in relation to the compounds of the catalyst system to be produced. Full disclosure of the necessary process can be found in WO03/051934 which is herein incorporated by reference.

The inert solvent must be chemically inert at least at the conditions (e.g. temperature) used during the dispersing step. Preferably, the solvent of said continuous phase does not contain dissolved therein any significant amounts of catalyst forming compounds. Thus, the solid particles of the catalyst are formed in the droplets from the compounds which originate from the dispersed phase (i.e. are provided to the emulsion in a solution dispersed into the continuous phase).

The terms "immobilisation" and "solidification" are used herein interchangeably for the same purpose, i.e. for forming free flowing solid catalyst particles in the absence of an external porous particulate carrier, such as silica. The solidification happens thus within the droplets. Said step can be effected in various ways as disclosed in said WO03/051934 Preferably solidification is caused by an external stimulus to the emulsion system such as a temperature change to cause the solidification. Thus in said step the catalyst component (s) remain "fixed" within the formed solid particles. It is also possible that one or more of the catalyst components may take part in the solidification/immobilisation reaction.

Accordingly, solid, compositionally uniform particles having a predetermined particle size range can be obtained.

Furthermore, the particle size of the catalyst particles of the invention can be controlled by the size of the droplets in the solution, and spherical particles with a uniform particle size distribution can be obtained.

The invention is also industrially advantageous, since it enables the preparation of the solid particles to be carried out as a one-pot procedure. Continuous or semicontinuous processes are also possible for producing the catalyst.

Dispersed Phase

The principles for preparing two phase emulsion systems are known in the chemical field. Thus, in order to form the two phase liquid system, the solution of the catalyst component (s) and the solvent used as the continuous liquid phase have to be essentially immiscible at least during the dispersing step. This can be achieved in a known manner e.g. by choosing said two liquids and/or the temperature of the dispersing step/solidifying step accordingly.

A solvent may be employed to form the solution of the catalyst component (s). Said solvent is chosen so that it dissolves said catalyst component (s). The solvent can be preferably an organic solvent such as used in the field, comprising an optionally substituted hydrocarbon such as linear or branched aliphatic, alicyclic or aromatic hydrocarbon, such as a linear or cyclic alkane, an aromatic hydrocarbon and/or a halogen containing hydrocarbon.

Examples of aromatic hydrocarbons are toluene, benzene, ethylbenzene, propylbenzene, butylbenzene and xylene. Toluene is a preferred solvent. The solution may comprise one or more solvents. Such a solvent can thus be used to facilitate the emulsion formation, and usually does not form part of the solidified particles, but e.g. is removed after the solidification step together with the continuous phase.

Alternatively, a solvent may take part in the solidification, e.g. an inert hydrocarbon having a high melting temperature (waxes), such as above 40° C., suitably above 70° C., e.g. above 80° C. or 90° C., may be used as solvents of the dispersed phase to immobilise the catalyst compounds within the formed droplets.

In another embodiment, the solvent consists partly or completely of a liquid monomer, e.g. liquid olefin monomer designed to be polymerised in a "prepolymerisation" immobilisation step.

Continuous Phase

The solvent used to form the continuous liquid phase is a single solvent or a mixture of different solvents and may be immiscible with the solution of the catalyst components at least at the conditions (e.g. temperatures) used during the dispersing step. Preferably said solvent is inert in relation to said compounds.

The term "inert in relation to said compounds" means herein that the solvent of the continuous phase is chemically inert, i.e. undergoes no chemical reaction with any catalyst forming component. Thus, the solid particles of the catalyst are formed in the droplets from the compounds which originate from the dispersed phase, i.e. are provided to the emulsion in a solution dispersed into the continuous phase.

It is preferred that the catalyst components used for forming the solid catalyst will not be soluble in the solvent of the continuous liquid phase. Preferably, said catalyst components are essentially insoluble in said continuous phase forming solvent.

Solidification takes place essentially after the droplets are formed, i.e. the solidification is effected within the droplets e.g. by causing a solidifying reaction among the compounds present in the droplets. Furthermore, even if some solidifying agent is added to the system separately, it reacts within the droplet phase and no catalyst forming components go into the continuous phase.

The term "emulsion" used herein covers both bi- and multiphasic systems.

In a preferred embodiment said solvent forming the continuous phase is an inert solvent including a halogenated organic solvent or mixtures thereof, preferably fluorinated organic solvents and particularly semi, highly or perfluorinated organic solvents and functionalised derivatives thereof. Examples of the above-mentioned solvents are semi, highly or perfluorinated hydrocarbons, such as alkanes, alkenes and cycloalkanes, ethers, e.g. perfluorinated ethers and amines, particularly tertiary amines, and functionalised derivatives thereof. Preferred are semi, highly or perfluorinated, particularly perfluorinated hydrocarbons, e.g. perfluorohydrocarbons of e.g. C3-C30, such as C4-C10. Specific examples of suitable perfluoroalkanes and perfluorocycloalkanes include perfluoro-hexane, -heptane, -octane and -(methylcyclohexane). Semi fluorinated hydrocarbons relates particularly to semifluorinated n-alkanes, such as perfluoroalkyl-alkane.

"Semi fluorinated" hydrocarbons also include such hydrocarbons wherein blocks of —C—F and —C—H alternate. "Highly fluorinated" means that the majority of the —C—H units are replaced with —C—F units. "Perfluorinated" means that all —C—H units are replaced with —C—F units. See the articles of A. Enders and G. Maas in "Chemie in unserer Zeit", 34. Jahrg. 2000, Nr. 6, and of Pierandrea Lo Nostro in "Advances in Colloid and Interface Science", 56 (1995) 245-287, Elsevier Science.

Dispersing Step

The emulsion can be formed by any means known in the art: by mixing, such as by stirring said solution vigorously to said solvent forming the continuous phase or by means of mixing mills, or by means of ultra sonic wave, or by using a so called phase change method for preparing the emulsion by first forming a homogeneous system which is then transferred by changing the temperature of the system to a biphasic system so that droplets will be formed.

The two phase state is maintained during the emulsion formation step and the solidification step, as, for example, by appropriate stirring.

Additionally, emulsifying agents/emulsion stabilisers can be used, preferably in a manner known in the art, for facilitating the formation and/or stability of the emulsion. For the said purposes e.g. surfactants, e.g. a class based on hydrocarbons (including polymeric hydrocarbons with a molecular weight e.g. up to 10 000 and optionally interrupted with a heteroatom(s)), preferably halogenated hydrocarbons, such as semi- or highly fluorinated hydrocarbons optionally having a functional group selected e.g. from —OH, —SH, $NH_2$, $NR"_2$, —COOH, —$COONH_2$, oxides of alkenes, —CR"=$CH_2$, where R" is hydrogen, or C1-C20 alkyl, C2-20-alkenyl or C2-20-alkynyl group, oxo-groups, cyclic ethers and/or any reactive derivative of these groups, like alkoxy, or carboxylic acid alkyl ester groups, or, preferably semi-, highly- or perfluorinated hydrocarbons having a functionalised terminal, can be used. The surfactants can be added to the catalyst solution, which forms the dispersed phase of the emulsion, to facilitate the forming of the emulsion and to stabilize the emulsion.

Alternatively, an emulsifying and/or emulsion stabilising aid can also be formed by reacting a surfactant precursor bearing at least one functional group with a compound reactive with said functional group and present in the catalyst solution or in the solvent forming the continuous phase. The obtained reaction product acts as the actual emulsifying aid and or stabiliser in the formed emulsion system.

Examples of the surfactant precursors usable for forming said reaction product include e.g. known surfactants which bear at least one functional group selected e.g. from —OH, —SH, $NH_2$, $NR"_2$, —COOH, —$COONH_2$, oxides of alkenes, —CR"=$CH_2$, where R" is hydrogen, or C1-C20 alkyl, C2-20-alkenyl or C2-20-alkynyl group, oxo-groups, cyclic ethers with 3 to 5 ring atoms, and/or any reactive derivative of these groups, like alkoxy or carboxylic acid alkyl ester groups; e.g. semi-, highly or perfluorinated hydrocarbons bearing one or more of said functional groups. Preferably, the surfactant precursor has a terminal functionality as defined above.

The compound reacting with such surfactant precursor is preferably contained in the catalyst solution and may be a further additive or one or more of the catalyst forming compounds. Such compound is e.g. a compound of group 13 (e.g. MAO and/or an aluminium alkyl compound and/or a transition metal compound).

If a surfactant precursor is used, it is preferably first reacted with a compound of the catalyst solution before the addition of the transition metal compound. In one embodiment e.g. a highly fluorinated C1-n (suitably C4-30- or C5-15) alcohol (e.g. highly fluorinated heptanol, octanol or nonanol), oxide (e.g. propenoxide) or acrylate ester is reacted with a cocatalyst to form the "actual" surfactant. Then, an additional amount of cocatalyst and the transition metal compound is added to said solution and the obtained solution is dispersed to the solvent forming the continuous phase. The "actual" surfactant solution may be prepared before the dispersing step or in the dispersed system. If said solution is made before the dispersing step, then the prepared "actual" surfactant solution and the transition metal solution may be dispersed successively (e.g. the surfactant solution first) to the immiscible solvent, or be combined together before the dispersing step.

Solidification

The solidification of the catalyst component(s) in the dispersed droplets can be effected in various ways, e.g. by causing or accelerating the formation of said solid catalyst forming reaction products of the compounds present in the droplets. This can be effected, depending on the used compounds and/or the desired solidification rate, with or without an external stimulus, such as a temperature change of the system.

In a particularly preferred embodiment, the solidification is effected after the emulsion system is formed by subjecting the system to an external stimulus, such as a temperature change. Temperature differences of e.g. 5 to 100° C., such as 10 to 100° C., or 20 to 90° C., such as 50 to 90° C. can be used.

The emulsion system may be subjected to a rapid temperature change to cause a fast solidification in the dispersed system. The dispersed phase may e.g. be subjected to an immediate (within milliseconds to few seconds) temperature change in order to achieve an instant solidification of the component (s) within the droplets. The appropriate temperature change, i.e. an increase or a decrease in the temperature of an emulsion system, required for the desired solidification rate of the components cannot be limited to any specific range, but naturally depends on the emulsion system, i.a. on the used compounds and the concentrations/ratios thereof, as well as on the used solvents, and is chosen accordingly. It is also evident that any techniques may be used to provide sufficient heating or cooling effect to the dispersed system to cause the desired solidification.

In one embodiment the heating or cooling effect is obtained by bringing the emulsion system with a certain temperature to an inert receiving medium with significantly different temperature, e.g. as stated above, whereby said temperature change of the emulsion system is sufficient to cause the rapid solidification of the droplets. The receiving medium can be gaseous, e.g. air, or a liquid, preferably a solvent, or a mixture of two or more solvents, wherein the catalyst component (s) is (are) immiscible and which is inert in relation to the catalyst component (s). For instance, the receiving medium comprises the same immiscible solvent used as the continuous phase in the first emulsion formation step.

Said solvents can be used alone or as a mixture with other solvents, such as aliphatic or aromatic hydrocarbons, such as alkanes. Preferably a fluorinated solvent as the receiving medium is used, which may be the same as the continuous phase in the emulsion formation, e.g. perfluorinated hydrocarbon.

Alternatively, the temperature difference may be effected by gradual heating of the emulsion system, e.g. up to 10° C. per minute, preferably 0.5 to 6° C. per minute and more preferably in 1 to 5° C. per minute.

In case a melt of e.g. a hydrocarbon solvent is used for forming the dispersed phase, the solidifcation of the droplets may be effected by cooling the system using the temperature difference stated above.

Preferably, the "one phase" change as usable for forming an emulsion can also be utilised for solidifying the catalytically active contents within the droplets of an emulsion system by, again, effecting a temperature change in the dispersed system, whereby the solvent used in the droplets becomes miscible with the continuous phase, preferably a fluorous continuous phase as defined above, so that the droplets become impoverished of the solvent and the solidifying components remaining in the "droplets" start to solidify. Thus the immisciblity can be adjusted with respect to the solvents and conditions (temperature) to control the solidification step.

The miscibility of e.g. organic solvents with fluorous solvents can be found from the literature and be chosen accordingly by a skilled person. Also the critical temperatures needed for the phase change are available from the literature or can be determined using methods known in the art, e.g. the Hildebrand-Scatchard-Theorie. Reference is also made to the articles of A. Enders and G. and of Pierandrea Lo Nostro cited above.

Thus according to the invention, the entire or only part of the droplet may be converted to a solid form. The size of the "solidified" droplet may be smaller or greater than that of the original droplet, e.g. if the amount of the monomer used for the prepolymerisation is relatively large.

The solid catalyst particles recovered can be used, after an optional washing step, in a polymerisation process of an olefin. Alternatively, the separated and optionally washed solid particles can be dried to remove any solvent present in the particles before use in the polymerisation step. The separation and optional washing steps can be effected in a known manner, e.g. by filtration and subsequent washing of the solids with a suitable solvent.

The droplet shape of the particles may be substantially maintained. The formed particles may have a mean size range of 1 to 500 µm, e.g. 5 to 500 µm, advantageously 5 to 200 µm or 10 to 150 µm. Even a mean size range of 5 to 60 µm is possible. The size may be chosen depending on the polymerisation the catalyst is used for. Advantageously, the mean particle size of the ready particulate catalysts of the invention are in the range of 2 to 150 µm, preferably 5 to 120 µm, more preferably 5 to 90 µm and especially in the range 10 to 70 µm. The particles are essentially spherical in shape, they have a low porosity and a low surface area.

The formation of solution can be effected at a temperature of 0-100° C., e.g. at 20-80° C. The dispersion step may be effected at −20° C.-100° C., e.g. at about −10-70° C., such as at −5 to 30° C., e.g. around 0° C.

To the obtained dispersion an emulsifying agent as defined above, may be added to improve/stabilise the droplet formation. The solidification of the catalyst component in the droplets is preferably effected by raising the temperature of the mixture, e.g. from 0° C. temperature up to 100° C., e.g. up to 60-90° C., gradually. E.g. in 1 to 180 minutes, e.g. 1-90 or 5-30 minutes, or as a rapid heat change. Heating time is dependent on the size of the reactor.

During the solidification step, which is preferably carried out at about 60 to 100° C., preferably at about 75 to 95° C., (below the boiling point of the solvents) the solvents may preferably be removed and optionally the solids are washed with a wash solution, which can be any solvent or mixture of solvents such as those defined above and/or used in the art, preferably a hydrocarbon, such as pentane, hexane or heptane, suitably heptane. The washed catalyst can be dried or it can be slurried into an oil and used as a catalyst-oil slurry in polymerisation process.

All or part of the preparation steps can be done in a continuous manner. Reference is made to WO2006/069733 describing principles of such a continuous or semicontinuous preparation methods of the solid catalyst types, prepared via emulsion/solidification method.

Polymerisation

The olefin polymerized using the catalyst of the invention is preferably propylene or a higher alpha-olefin. It may also be ethylene or a mixture of ethylene and an α-olefin. Alternatively, it may also be mixture of alpha olefins, for example $C_{2-20}$ olefins, e.g. ethylene, propylene, 1-butene, 1-hexene, 4-methyl-1-pentene, 1-octene etc. The olefins polymerized in the method of the invention may include any compound which includes unsaturated polymerizable groups. Thus for example unsaturated compounds, such as $C_{6-20}$ olefins (including cyclic and polycyclic olefins (e.g. norbornene)), and polyenes, especially $C_{4-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include α,ω linear dienes such as 1,5-hexadiene, 1,6-heptadiene, 1,8-nonadiene, 1,9-decadiene, etc.

The catalysts of the present invention are particularly suited for use in the manufacture of polypropylene polymers, either copolymers or homopolymers thereof.

As comonomers to propylene are preferably used ethylene, or higher olefins, e.g. C4-C12 olefins, like 1-butene, 1-hexene, 1-octene or any mixtures thereof, preferably ethylene. It is especially preferred if the copolymer is a propylene ethylene copolymer. That copolymer may be a random copolymer or a heterophasic copolymer. The ethylene content in such a polymer may be up to 50 wt %, e.g. 0.5 to 20 wt %, depending on the desired properties of the polymer. Especially, the catalysts are used to manufacture polypropylene homopolymers, random polypropylene copolymers or heterophasic polypropylene copolymers, preferably with ethylene as comonomer. Heterophasic copolymers may contain a propylene homopolymer or copolymer matrix with an amorphous propylene copolymer component. Such polymers are typically made in a multistep process well known in the art.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase reactors.

In case of propylene polymerisation for slurry reactors, the reaction temperature will generally be in the range 60 to 110° C. (e.g. 60-90° C.), the reactor pressure will generally be in the range 5 to 80 bar (e.g. 20-60 bar), and the residence time will generally be in the range 0.1 to 5 hours (e.g. 0.3 to 2 hours). The monomer is usually used as reaction medium.

For gas phase reactors, the reaction temperature used will generally be in the range 60 to 115° C. (e.g. 70 to 110° C.), the reactor pressure will generally be in the range 10 to 25 bar, and the residence time will generally be 0.5 to 8 hours (e.g. 0.5 to 4 hours). The gas used will be the monomer optionally as mixture with a non-reactive gas such as nitrogen or propane. In addition to actual polymerisation steps and reactors, the process can contain any additional polymerisation steps, like prepolymerisation step, and any further after reactor handling steps as known in the art.

For solution polymerization, an aliphatic or aromatic solvent can be used to dissolve the monomer and the polymer, and the polymerization temperature will generally be in the range 80 to 200° C. (e.g. 90 to 150° C.)

Generally the quantity of catalyst used will depend upon the nature of the catalyst, the reactor types and conditions and the properties desired for the polymer product. As is well known in the art hydrogen can be used for controlling the molecular weight of the polymer.

The metallocene catalysts of the invention possess excellent catalyst activity and good hydrogen response. The catalysts are also able to provide polymers of high weight average molecular weight Mw.

Moreover, the random copolymerisation behaviour of metallocene catalysts of the invention shows comparable polymerisation activity and decay of activity with increase of ethylene feed as a symmetrical analogue but importantly the weight average molecular weight Mw does not show a negative correlation with increasing ethylene feed as it is witnessed with symmetrical catalysts. This indicates a reduced tendency of chain transfer to ethylene.

Another significant difference is the superior conversion of ethylene with metallocenes of the invention.

Polymers obtained with the metallocenes of the invention have normal particle morphologies.

Heterophasic copolymers can be prepared with the catalysts of the invention and the activity of this catalyst in both liquid and gas phase is much better than that obtained with a standard symmetrical metallocene. The higher activity in bulk and gas phase makes those of the invention the preferred catalyst over symmetrical ones.

In general therefore the invention catalysts can provide:
high activity in bulk propylene polymerisation;
very high molecular weight capability;
improved ethylene incorporation in propylene copolymers;
high activity obtained in homopolymerisation and C3/C2 copolymerization;
higher molecular weight of the C3/C2 copolymer produced;
good polymer morphology.

It is a feature of the invention that the claimed catalysts enable the formation of polymers with high molecular weight. These features can be achieved at commercially interesting polymerisation temperatures, e.g. 60° C. or more. It is a preferred feature of the invention that the catalysts of the invention are used to polymerise propylene at a temperature of at least 60° C., preferably at least 65° C., such as at least 70° C.

We have shown in the laboratory scale examples below that catalyst activities can also be high, such as 30 kg polymer/g/cat or more in the examples. It will be appreciated that activity is dependent on hydrogen concentration.

The Mw of the polymers made using the catalysts of the invention may exceed 200,000, preferably at least 300,000, even at least 500,000. Values even more than 800,000 have also been achieved by using catalyst of the invention. It should be noted, however, that hydrogen can be used as molecular weight regulator as is well known in the art. Thus, it's possible to get also low MW polymer, like polymers having Mw 100,00 or even less. Mw/Mn values are generally low, e.g. less than 4, such as less than 3.5 or even less than 3.

Polypropylenes made by the metallocenes of the invention can be made with $MFR_2$ values in the whole range of interest, that is from very high, even as high as 2000, for example 1000 or 500, to very low, that is fractional values of less than 0.1 or even less like 0.05 kg/10 min. For many applications typical $MFR_2$ area is e.g. 0.1 to 200 kg/10 min. Hydrogen can be used to manipulate MFR as is well known. Further, amount of comonomer has effect on MFR values.

The polymers made by the catalysts of the invention are useful in all kinds of end articles such as pipes, films (cast, blown or BOPP films), fibers, moulded articles (e.g. injection moulded, blow moulded, rotomoulded articles), extrusion coatings and so on.

The invention will now be illustrated by reference to the following non-limiting examples.

Analytical Tests: Measurement Methods:
ICP Analysis

The elemental analysis of a catalyst was performed by taking a solid sample of mass M, cooling over dry ice. Samples were diluted up to a known volume, V, by dissolving in nitric acid ($HNO_3$, 65%, 5% of V) and freshly deionised (DI) water (5% of V). The solution was then added to hydrofluoric acid (HF, 40%, 3% of V), diluted with DI water up to the final volume, V, and left to stabilise for two hours. The analysis was run at room temperature using a Thermo Elemental iCAP 6300 Inductively Coupled Plasma—Optical Emission Spectrometer (ICP-OES) which was calibrated using a blank (a solution of 5% $HNO_3$, 3% HF in DI water), and 6 standards of 0.5 ppm, 1 ppm, 10 ppm, 50 ppm, 100 ppm and 300 ppm of Al, with 0.5 ppm, 1 ppm, 5 ppm, 20 ppm, 50 ppm and 100 ppm of Hf and Zr in solutions of 5% $HNO_3$, 3% HF in DI water.

Immediately before analysis the calibration is 'resloped' using the blank and 100 ppm Al, 50 ppm Hf, Zr standard, a quality control sample (20 ppm Al, 5 ppm Hf, Zr in a solution of 5% $HNO_3$, 3% HF in DI water) is run to confirm the reslope. The QC sample is also run after every 5th sample and at the end of a scheduled analysis set.

The content of hafnium was monitored using the 282.022 nm and 339.980 nm lines and the content for zirconium using 339.198 nm line. The content of aluminium was monitored via the 167.079 nm line, when Al concentration in ICP sample was between 0-10 ppm (calibrated only to 100 ppm) and via the 396.152 nm line for Al concentrations above 10 ppm.

The values reported in Table 4 are an average of three successive aliquots taken from the same sample and are related back to the original catalyst by inputting the original mass of sample and the dilution volume into the software.

DSC Analysis

Melting temperature $T_m$ and crystallization temperature $T_c$ were measured on approx. 5 mg samples with a Mettler-Toledo 822e differential scanning calorimeter (DSC), according to ISO11357-3 in a heat/cool/heat cycle with a scan rate of 10° C./min in the temperature range of +23 to +225° C. under a nitrogen flow rate of 50 ml $min^{-1}$. Melting and crystallization temperatures were taken as the endotherm and exotherm peaks, respectively in the second heating and in the cooling step.

Calibration of the instrument was performed with $H_2O$, Lead, Tin, Indium, according to ISO11357-1. The maximum error in temperature from calibration was less than 0.3° C.

Melt Flow Rate

The melt flow rate (MFR) is determined according to ISO 1133 and is indicated in g/10 min. The MFR is an indication of the flowability, and hence the processability, of the polymer. The higher the melt flow rate, the lower the viscosity of the polymer. The MFR is determined at 230° C. and may be determined at different loadings such as 2.16 kg ($MFR_2$) or 21.6 kg ($MFR_{21}$).

Quantification of Polypropylene Homopolymer Microstructure by NMR Spectroscopy

Quantitative nuclear-magnetic resonance (NMR) spectroscopy was used to quantify the isotacticity and content of regio-defects of the polypropylene homopolymers. Quantitative $^{13}C\{^1H\}$ NMR spectra recorded in the solution-state using a Bruker Advance III 400 NMR spectrometer operating at 400.15 and 100.62 MHz for $^1H$ and $^{13}C$ respectively. All spectra were recorded using a $^{13}C$ optimised 10 mm selective excitation probehead at 125° C. using nitrogen gas for all pneumatics. Approximately 200 mg of material was dissolved in 1,2-tetrachloroethane-$d_2$ (TCE-$d_2$). This setup was chosen primarily for the high resolution needed for tacticity distribution quantification (Busico, V., Cipullo, R., Prog. Polym. Sci. 26 (2001) 443; Busico, V.; Cipullo, R., Monaco, G., Vacatello, M., Segre, A. L., Macromolecules 30 (1997) 6251). Standard single-pulse excitation was employed utilising the NOE and bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun. 2007, 28, 11289). A total of 8192 (8 k) transients were acquired per spectra. Quantitative $^{13}C\{^{1}H\}$ NMR spectra were processed, integrated and relevant quantitative properties determined from the integrals using proprietary computer programs. All chemical shifts are internally referenced to the methyl signal of the isotactic pentad mmmm at 21.85 ppm.

The tacticity distribution was quantified through integration of the methyl region between 23.6 and 19.7 ppm correcting for any sites not related to the stereo sequences of interest (Busico, V., Cipullo, R., Prog. Polym. Sci. 26 (2001) 443; Busico, V., Cipullo, R., Monaco, G., Vacatello, M., Segre, A. L., Macromolecules 30 (1997) 6251). The pentad isotacticity was determined through direct integration of the methyl region and reported as either the mole fraction or percentage of isotactic pentad mmmm with respect to all steric pentads i.e. [mmmm]=mmmm/sum of all steric pentads. When appropriate integrals were corrected for the presence of sites not directly associated with steric pentads.

Characteristic signals corresponding to regio irregular propene insertion were observed (Resconi, L., Cavallo, L., Fait, A., Piemontesi, F., Chem. Rev. 2000, 100, 1253). The presence of secondary inserted propene in the form of 2,1 erythro regio defects was indicated by the presence of the two methyl signals at 17.7 and 17.2 ppm and confirmed by the presence of other characteristic signals. The amount of 2,1 erythro regio defects was quantified using the average integral (e) of the e6 and e8 sites observed at 17.7 and 17.2 ppm respectively, i.e. e=0.5*(e6+e8). Characteristic signals corresponding to other types of regio irregularity were not observed (Resconi, L., Cavallo, L., Fait, A., Piemontesi, F., Chem. Rev. 2000, 100, 1253). The amount of primary inserted propene (p) was quantified based on the integral of all signals in the methyl region (CH3) from 23.6 to 19.7 ppm paying attention to correct for other species included in the integral not related to primary insertion and for primary insertion signals excluded from this region such that p=CH3+2*e. The relative content of a specific type of regio defect was reported as the mole fraction or percentage of said regio defect with respect all observed forms of propene insertion i.e. sum of all primary (1,2), secondary (2,1) and tertiary (3,1) inserted propene units, e.g. [21e]=e/(p+e+t+i). The total amount of secondary inserted propene in the form of 2,1-erythro or 2,1-threo regio defects was quantified as sum of all said regio irregular units, i.e. [21]=[21e]+[21t].

Quantification of Copolymer Microstructure by NMR Spectroscopy

Quantitative nuclear-magnetic resonance (NMR) spectroscopy was used to quantify the comonomer content and comonomer distribution of the copolymers, specifically propene-co-ethylene copolymers. Quantitative $^{13}C\{^{1}H\}$ NMR spectra recorded in the solution-state using a Bruker Advance III 400 NMR spectrometer operating at 400.15 and 100.62 MHz for $^{1}H$ and $^{13}C$ respectively. All spectra were recorded using a $^{13}C$ optimised 10 mm selective excitation probehead at 125° C. using nitrogen gas for all pneumatics. Approximately 200 mg of material was dissolved in 1,2-tetrachloroethane-$d_2$ (TCE-$d_2$) with chromium-(III)-acetylacetonate (Cr(acac)$_3$) resulting in a 65 mM solution of relaxation agent in solvent (Singh, G., Kothari, A., Gupta, V., Polymer Testing 28 5 (2009), 475). This setup was chosen primarily for the high resolution and quantitative spectra needed for accurate ethylene content determination. Standard single-pulse excitation was employed without NOE, using an optimised tip angle, 1 s recycle delay and bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun. 2007, 28, 11289). A total of 6144 (6 k) transients were acquired per spectra. Quantitative $^{13}C\{^{1}H\}$ NMR spectra were processed, integrated and relevant quantitative properties determined from the integrals using proprietary computer programs. All chemical shifts were indirectly referenced to the central methylene group of the ethylene block (EEE) at 30.00 ppm using the chemical shift of the solvent. This approach allowed comparable referencing even when this structural unit was not present.

Characteristic signals corresponding to regio irregular propene insertion were observed (Resconi, L., Cavallo, L., Fait, A., Piemontesi, F., Chem. Rev. 2000, 100, 1253).].

Characteristic signals corresponding to the incorporation of ethylene were observed (Cheng, H. N., Macromolecules 17, 1984, 1950). The comonomer content was calculated as the mole fraction or percent of incorporated ethylene with respect to all monomer in the copolymer using the method of Wang et. al. (Wang, W-J., Zhu, S., Macromolecules 33, 2000, 1157) through integration of multiple signals spanning the whole spectral $^{13}C$ spectra. This analyse method was chosen for its robust nature and ability to account for the presence of regio irregular propene insertion when needed. Integral regions were slightly adjusted to increase applicability across the whole range of encountered comonomer contents.

For systems where only isolated ethylene incorporation (PPEPP) was observed the method of Wang et. al. was modified to reduce the influence of non-zero integrals used to quantify higher order comonomer sequences. In such cases the term for the absolute ethylene content was determined based upon only E=0.5(S$\beta\beta$++S$\beta\gamma$+S$\beta\delta$+0.5(S$\alpha\beta$+S$\alpha\gamma$☐)) or E=0.5($I_H$+$I_G$+0.5($I_C$+$I_D$)) using the same notation as Wang et. al. (Wang, W-J., Zhu, S., Macromolecules 33, 2000, 1157). The term used for absolute propylene content (P) was not modified and the mole fraction of ethylene calculated as [E]=E/(E+P). The comonomer content in weight percent was calculated from the mole fraction in the usual way i.e. [E wt %]=100*([E]*28.06)/ ((([E]*28.06)+((1-[E])*42.08)).

GPC: Molecular Weight Averages, Molecular Weight Distribution, and Polydispersity Index ($M_n$, $M_w$, $M_w/M_n$)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2×GMHXL-HT and 1× G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 μL of sample solution were injected per analysis. The column set was calibrated using universal calibration (according to ISO 16014-2:2003) with at least 15 narrow MWD polystyrene (PS) standards in the range of 1 kg/mol to 12 000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Ethylene Content (FTIR $C_2$)

Ethylene content was measured with Fourier transform infrared spectroscopy (FTIR) calibrated to results obtained by $^{13}C$ NMR spectroscopy using a method which accounts for regio-irregular propene insertion. When measuring the ethylene content in polypropylene, a thin film of the sample (thickness about 0.220 to 0.250 mm) was prepared by hotpressing at 230° C. (preheat 5 min., press 1 min., cooling (cold water) 5 min.) using a Graseby Specac press. The FTIR spectra of the sample was recorded immediately with Nicolet Protégé 460 spectrometer from 4000 to 400 $cm^{-1}$, resolution 4 $cm^{-1}$, scans 64. The area of absorption peak at 733 $cm^{-1}$ (baseline from 700 $cm^{-1}$ to 760 $cm^{-1}$) and height of reference peak at 809 $cm^{-1}$ (baseline from 780 $cm^{-1}$ to 880 $cm^{-1}$) were evaluated. The result was calculated using the following formula $$E_{tot}=a \times A/R+b$$

where
A=area of absorption peak at 733 $cm^{-1}$
R=height of reference peak at 809 $cm^{-1}$
$E_{tot}$=C2 content (wt.-%)
a, b are calibration constants determined by correlation of multiple calibration standards of know ethylene content as determined by $^{13}C$ NMR spectroscopy to A/R.

The result was reported as an average of two measurements.

Examples

Chemicals

All the chemicals and chemical reactions were handled under an inert gas atmosphere using Schlenk and glovebox techniques, with oven-dried glassware, syringes, needles or cannulas.

MAO was purchased from Albermarle and used as a 30 wt-% solution in toluene.

The mixture of perfluoroalkylethyl acrylate esters (CAS 65605-70-1) used as the surfactant was purchased from the Cytonix corporation, dried over activated molecular sieves (2 times) and degassed by argon bubbling prior to use.

Perfluoro-1,3-dimethylcyclohexane (PFC, CAS 335-27-3) was dried over activated molecular sieves (2 times) and degassed by argon bubbling prior to use.

Triethylaluminum was purchased from Crompton and used in pure form. Hydrogen is provided by AGA and purified before use.

Propylene is provided by Borealis and adequately purified before use. 2 M HCl, 12 M HCl (Reachim, Russia), silica gel 60 (40-63 um, Merck), $K_2CO_3$ (Merck), $ZrCl_4(THF)_2$ magnesium turnings (Acros), TsOH (Aldrich), nBuLi (Chemetall), n-hexane (Merck), were used as received. Toluene (Merck), THF (Merck), dichloromethane (Merck), were kept and distilled over Na/K alloy. Dichlorodimethylsilane (Merck) was distilled before use. $CDCl_3$, DMSO-$d_6$ and $CD_2Cl_2$ (Deutero GmbH) for NMR experiments were dried and kept over $CaH_2$. methyl iodide (Acros) 1-bromo-3,5-di-tert-butylbenzene (Aldrich) has been used as received. Bis (2,6-diisopropylphenyl)imidazolium chloride, i.e. IPr(HCl), and $(IPr)NiCl_2(PPh_3)$ were synthesized as described in [Hintermann, L. *Beilstein J. Org. Chem.* 2007, 3, 1.] and [Matsubara, K.; Ueno, K.; Shibata, Y. *Organometallics* 2006, 25, 3422.], respectively. 4-Bromo-1-methoxy-2-methylindane was obtained as described in [Izmer, V. V.; Lebedev, A. Y.; Nikulin, M. V.; Ryabov, A. N.; Asachenko, A. F.; Lygin, A. V.; Sorokin, D. A.; Voskoboynikov, A. Z. *Organometallics* 2006, 25, 1217.].

Synthesis of rac-anti-dimethylsilanediyl(2-methyl-4-(4'-tert-butylphenyl)-6-tert-butyl-inden-1-yl)(2-methyl-4-phenyl-5-methoxy-6-tert-butyl-inden-1-yl) zirconium dichloride (Complex CMC1—comparative)

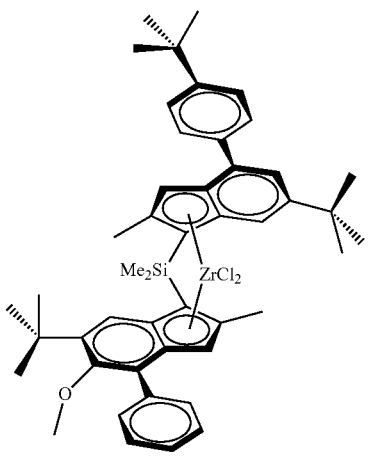

The new synthesis and characterization of the known 7-(4-tert-butylphenyl)-2,5-dimethyl-1H-indene is described below:

2-Bromo-1-(chloromethyl)-4-methylbenzene

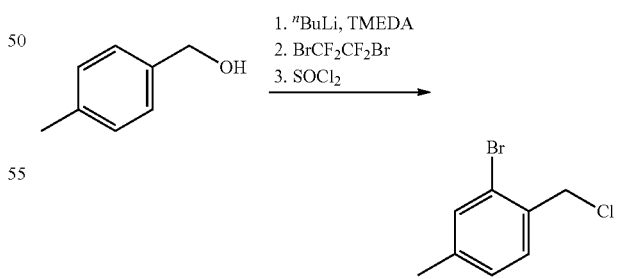

280 ml (0.70 mol) of 2.5 M $^nBuLi$ in hexanes was added dropwise at room temperature to a vigorously stirred mixture of 42.7 g (0.35 mol) of 4-methylbenzyl alcohol and 58.1 g (0.50 mol) of TMEDA in 700 ml of n-hexane. The resulting solution was refluxed for 12 h, then cooled to −78° C., and 137 g (0.52 mol) of 1,2-dibromoperfluoroethane was added dropwise at this temperature. The resulting mixture was allowed to warm to room temperature and stirred for 10 h followed by quenching with water (500 ml). The organic layer was separated, washed with 3×200 ml of water, dried over $Na_2SO_4$, and then evaporated to dryness. The residue dissolved in 600 ml of dichloromethane was treated with 60 ml of thionyl chloride. This mixture was stirred overnight, an excess of thionyl chloride was distilled off at atmospheric pressure. The residue was distilled in vacuum, b.p. 77-85° C./5 mm Hg. Yield 59.0 g (42%) of the title compound.

Anal. calc. for $C_8H_8BrCl$: C, 43.77; H, 3.67. Found: C, 43.90; H, 3.49.

$^1$H NMR ($CDCl_3$): δ 7.41 (s, 1H, 3-H), 7.34 (d, J=7.7 Hz, 1H, 5-H), 7.11 (d, J=7.7 Hz, 1H, 6-H), 4.67 (s, 2H, $CH_2Cl$), 2.32 (s, 3H, Me).

3-(2-Bromo-4-methylphenyl)-2-methylpropanoyl chloride

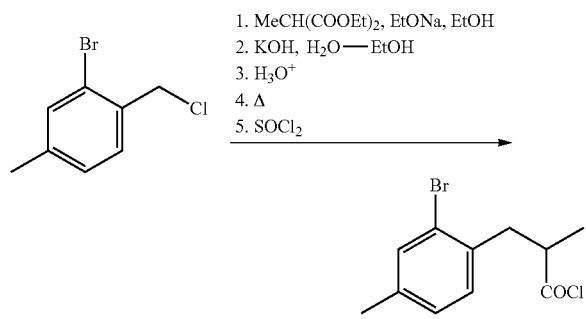

26.2 g (0.150 mol) of diethyl methylmalonate was added to a sodium ethoxide solution (prepared from 3.50 g of sodium metal and 120 ml of dry ethanol). This mixture was stirred for 15 min, then 59.0 g (0.150 mol) of 2-bromo-1-(chloromethyl)-4-methylbenzene was added dropwise with vigorous stirring at such a rate as to maintain gentle reflux. This mixture was refluxed for 2 h and then cooled to room temperature. A solution of 30 g of KOH in 80 ml of water was added. This mixture was refluxed for 4 h to saponificate the ester formed. Ethanol and water were distilled off until temperature reached 95° C., and 1000 ml of water and then 12 M HCl (to pH 1) were added to the residue. The precipitated substituted methylmalonic acid was filtered off, washed with 2×100 ml of water. Crude 3-(2-bromo-4-methylphenyl)-2-methylpropanoic acid was obtained as brown oil after decarboxylation of this substituted methylmalonic acid at 180° C. A mixture of this acid and 60 ml of $SOCl_2$ was stirred at room temperature for 24 h, then an excess of thionyl chloride was distilled off at atmospheric pressure. The product was distilled in vacuum, b.p. 102-125° C./5 mm Hg. Yield 25.8 g (62%).

Anal. calc. for $C_{11}H_{12}BrClO$: C, 47.94; H, 4.39. Found: C, 48.25; H, 4.61.

$^1$H NMR ($CDCl_3$): δ 7.38 (s, 1H, 3-H), 7.10 (d, J=7.7 Hz, 1H, 6-H), 7.04 (d, J=7.7 Hz, 5-H), 3.34-3.21 (m, 2H, CHH'CHMeCOCl and $CH_2$CHMeCOCl), 2.81 (dd, J=13.2 Hz, J=6.8 Hz, 1H, CHH'CHMeCOCl), 2.30 (s, 3H, 4-Me), 1.30 (d, J=6.7 Hz, 3H, $CH_2$CHMeCOCl).

4-Bromo-2,6-dimethylindan-1-one

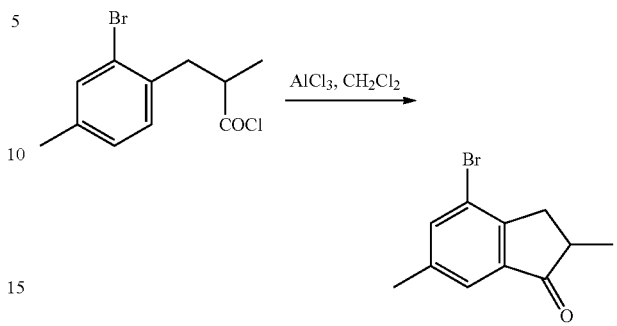

A solution of 25.8 g (93.6 mmol) of 3-(2-bromo-4-methylphenyl)-2-methylpropanoyl chloride in 50 ml of dichloromethane was added dropwise to a stirred suspension of 15.6 g (117 mmol, 1.25 eq.) of $AlCl_3$ in 120 ml of dichloromethane at +5° C. This mixture was stirred overnight at room temperature and then poured on 100 g of crushed ice. The organic layer was separated, and the aqueous layer was extracted with 2×75 ml of dichloromethane. The combined organic extract was washed by aqueous $K_2CO_3$, dried over $K_2CO_3$, passed through a short pad of silica gel 60 (40-63 μm), and then evaporated to dryness. This procedure gave 22.5 g (99%) of 4-bromo-2,6-dimethylindan-1-one which was further used without an additional purification.

Anal. calc. for $C_{11}H_{11}BrO$: C, 55.25; H, 4.64. Found: C, 55.49; H, 4.74.

$^1$H NMR ($CDCl_3$): δ 7.55 (s, 1H, 7-H), 7.45 (s, 1H, 5-H), 3.26 (dd, J=17.4 Hz, J=8.0 Hz, 1H, 3-H), 2.76-2.67 (m, 1H, 2-H), 2.57 (dd, J=17.4 Hz, J=3.7 Hz, 3'-H), 2.38 (s, 3H, 6-Me), 1.31 (d, J=7.5 Hz, 3H, 2-Me).

1-methoxy-2,6-dimethyl-4-Bromo-indane

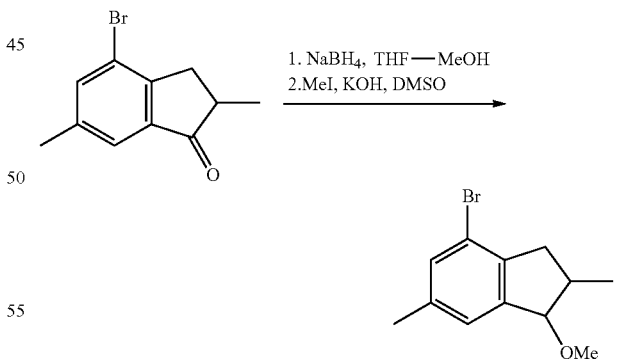

To a mixture of 22.5 g (ca. 94 mmol) of 2,6-dimethyl-4-bromo-indan-1-one and 5.32 g (141 mmol) of $NaBH_4$ in 200 ml of THF 100 ml of methanol was added dropwise by vigorous stirring for 7 h at 0-5° C. This mixture was stirred overnight at room temperature and then added to 1 liter of cold water. The resulting mixture was acidified by 2 M HCl to pH 5 and then extracted with 3×250 ml of dichloromethane. The combined organic extract was dried over $Na_2SO_4$ and evaporated to dryness. To a solution of the residue in 200 ml of DMSO 24.0 g (428 mmol) of KOH and 30.0 g (211 mmol) of MeI were added. This mixture was stirred overnight at ambient temperature, then the solution was decanted from an excess of KOH. The latter was washed with 2×150 ml of dichlorometane. The combined organic solution was washed with 2000 ml of water. The organic layer was separated, and the aqueous layer was additionally extracted with 2×100 ml of dichloromethane. The combined organic extract was washed with 5×1000 ml of water, dried over $Na_2SO_4$, passed through a short pad of silica gel 60 (40-63 μm), and the elute was evaporated dryness. This procedure gave 23.5 g (98%) of the title product as a slightly yellowish liquid.

Anal. calc. for $C_{12}H_{15}BrO$: C, 56.49; H, 5.93. Found: C, 56.64; H, 5.80.

$^1$H NMR (CDCl$_3$): δ 7.24 (s, 1H, 5-H of anti-isomer), 7.23 (s, 1H, 5-H of syn-isomer), 7.11 (s, 1H, 7-H of anti-isomer), 7.10 (s, 1H, 7-H of syn-isomer), 4.54 (d, J=5.7 Hz, 1H, 1-H of syn-isomer), 4.40 (d, J=4.3 Hz, 1H, 1-H of anti-isomer), 3.45 (s, 3H, OMe of anti-isomer), 3.41 (s, 3H, OMe of syn-isomer), 3.17 (dd, J=16.2 Hz, J=7.6 Hz, 1H, 3-H of anti-isomer), 2.93-2.86 (m, 1H, 3-H of syn-isomer), 2.66-2.59 (m, 2H, 3-H' and 2-H of syn-isomer), 2.54-2.45 (m, 1H, 2-H of anti-isomer), 2.39 (dd, J=16.2 Hz, J=5.3 Hz, 1H, 3-H' of anti-isomer), 2.32 (s, 6H, 6-Me of syn- and anti-isomer), 1.16 (d, J=7.1 Hz, 2-Me of anti-isomer), 1.07 (d, J=6.8 Hz, 2-Me of syn-isomer).

2,5-dimethyl-7-(4-tert-Butylphenyl)-1H-indene

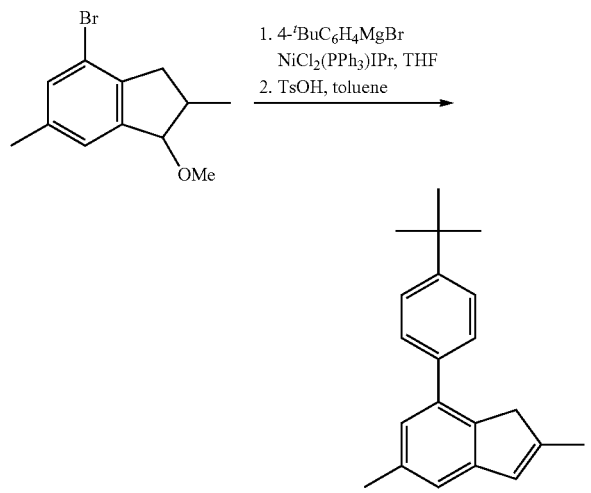

0.78 g (1.0 mmol, 1.1 mol. %) of NiCl$_2$(PPh$_3$)IPr and a solution of 23.5 g (92.1 mmol) of 1-methoxy-2,6-dimethyl-4-bromoindane in 50 ml of THF were added to a solution of 4-tert-butylphenylmagnesium bromide obtained from 42.6 g (0.200 mol) of 1-bromo-4-tert-butylbenzene and 7.00 g (0.288 mol, 1.44 eq.) of magnesium turnings in 250 ml of THF. A moderate reflux occurred after gentle warming of the reaction mixture which ceased after the following 3 min. This mixture was refluxed for 0.5 h. Finally, 1000 ml of 10% HCl was added, and the product was extracted with 500 ml of dichloromethane. The organic layer was separated, the aqueous layer was extracted with 100 ml of dichloromethane. The combined organic extract was evaporated to dryness to give a slightly greenish oily liquid. The aryl-substituted methoxyindane was isolated by flash-chromatography on silica gel 60 (40-63 μm; eluent: hexanes-dichloromethane=3:1, vol., then dichloromethane). To the solution of this product in 350 ml of toluene 0.5 g of TsOH was added. The resulting mixture was refluxed using Dean-Stark head for 20 min, then cooled to room temperature, and washed by 200 ml of 10% aqueous NaHCO$_3$. The organic layer was separated, the aqueous layer was extracted with 2×75 ml of dichloromethane. The combined organic solution was passed through a short pad of silica gel 60 (40-63 μm) and then evaporated to dryness. This procedure gave 25.4 g (99%) of the title product as a yellow oil.

Anal. calc. for $C_{21}H_{24}$: C, 91.25; H, 8.75. Found: C, 91.42; H, 8.89.

$^1$H NMR (CDCl$_3$): δ 7.44 (m, 4H, 2,3,5,6-H in C$_6$H$_4^t$Bu), 7.04 (s, 1H, 6-H in indenyl), 6.96 (s, 1H, 4-H in indenyl), 6.46 (s, 1H, 3-H in indenyl), 3.35 (s, 2H, 1-H in indenyl), 2.39 (s, 3H, 5-Me in indenyl), 2.10 (s, 3H, 2-Me in indenyl), 1.36 (s, 9H, $^t$Bu in C$_6$H$_4^t$Bu).

Alternative Process 5-tert-Butyl-7-(4-tert-butylphenyl)-2-methyl-1H-indene

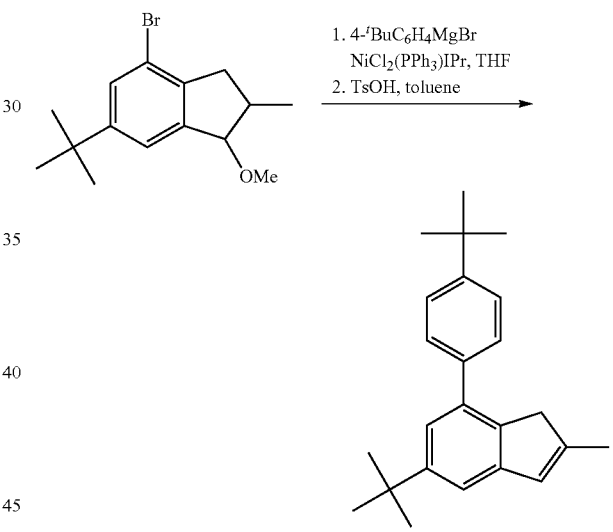

To a solution of 4-tert-butylphenylmagnesium bromide obtained from 43.1 g (0.202 mol) of 1-bromo-4-tert-butylbenzene and 7.60 g (0.313 mol, 1.55 eq) of magnesium turnings in 300 ml of THF 0.70 g (0.90 mmol, 0.45 mol. %) of NiCl$_2$(PPh$_3$)IPr and a solution of 60.0 g (0.202 mol) of 4-bromo-6-tert-butyl-1-methoxy-2-methylindane in 50 ml of THF were added. A moderate reflux occurs after gentle warming of the reaction mixture which ceased after the following 3 minutes. This mixture was refluxed for 0.5 h, and 1000 cm$^3$ of 10% HCl was added. The crude product was extracted with 500 ml of dichloromethane. The organic layer was separated, the aqueous layer was additionally extracted with 100 ml of dichloromethane. The combined organic extract was evaporated to dryness to give a slightly greenish oily liquid. This liquid was dissolved in 500 ml of toluene, and then 1.0 g of TsOH was added. The obtained solution was refluxed using Dean-Stark head for 25 min. The resulting mixture was washed by 200 ml of 10% aqueous NaHCO$_3$. The organic layer was separated, the aqueous layer was extracted with 2×75 ml of dichloromethane. The combined organic extract was evaporated to dryness, the residue was dissolved in 500 ml of dichloromethane, and the formed solution was passed through a short pad of silica gel 60 (40-63 um). The obtained elute was evaporated to dryness top give a slightly yellowish crude product which was then distilled in vacuum to give 49.2 g (77%) of the title product, b.p. 190-210° C./5 mm Hg.

Anal. calc. for $C_{24}H_{30}$: C, 90.51; H, 9.49. Found: C, 90.63; H, 9.33.

$^1$H NMR (CDCl$_3$): δ 7.49 (d, J=8.5 Hz, 2H, 2,6-H in $C_6H_4{}^tBu$), 7.45 (d, J=8.5 Hz, 2H, 3,5-H in $C_6H_4{}^tBu$), 7.29 (d, J=1.6 Hz, 1H, 6-H in indenyl), 7.18 (d, J=1.6 Hz, 1H, 4-H in indenyl), 6.51 (m, 1H, 3-H in indenyl), 3.36 (s, 2H, 1-H in indenyl), 2.12 (s, 3H, 2-Me in indenyl), 1.38 (s, 9H, 5-$^t$Bu in indenyl), 1.37 (s, 9H, $^t$Bu in $C_6H_4{}^tBu$).

[6-tert-Butyl-4-(4'-tert-butylphenyl)-2-methyl-1H-inden-1-yl](6-tert-butyl-5-methoxy-2-methyl-4-phenyl-1H-inden-1-yl)dimethylsilane

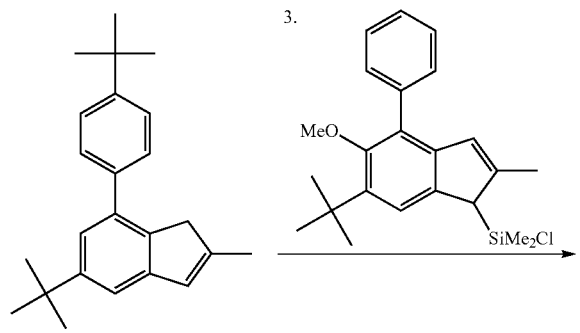

To a solution of 10.4 g (32.7 mmol) of 5-tert-butyl-7-(4-tert-butylphenyl)-2-methyl-1H-indene in 200 ml of ether 13.1 ml (32.8 mmol) of 2.5 M $^n$BuLi in hexanes were added in one portion at −40° C. This mixture was stirred overnight at room temperature, then cooled to −40° C., and 180 mg of CuCN was added. The resulting mixture was stirred for 1 h at −20° C., then cooled to −40° C., and a solution of 12.6 g (32.7 mmol) of (6-tert-butyl-5-methoxy-2-methyl-4-phenyl-1H-inden-1-yl)(chloro)dimethylsilane in 150 ml of ether was added in one portion. The formed mixture was stirred overnight at ambient temperature, and then 0.5 ml of water was added. This solution was filtered through a pad of silica gel 60 (40-63 um) which was additionally washed by dichloromethane (50 ml, then 2×20 ml). The combined organic elute was evaporated to dryness, and the residue was dried in vacuum. This procedure gave 22.8 g of [6-tert-butyl-4-(4-tert-butylphenyl)-2-methyl-1H-inden-1-yl](6-tert-butyl-5-methoxy-2-methyl-4-phenyl-1H-inden-1-yl)dimethylsilane (on the evidence of NMR spectroscopy, >90% purity as a ca. 3:1 mixture of diastereoisomers) which was further used without an additional purification.

Anal. calc. for $C_{47}H_{58}OSi$: C, 84.63; H, 8.76. Found: C, 84.89; H, 8.94.

$^1$H NMR (CDCl$_3$): δ 7.55-7.30 (m), 6.79 (s), 6.71 (s), 6.47 (s), 6.39 (s), 3.66-3.63 (m), 3.24 (s), 2.18 (s), 2.15 (s), 2.06 (s), 1.99 (s), 1.44 (s), 1.43 (s), 1.40 (s), 1.39 (s), 1.37 (s), 1.36 (s), −0.10 (s), −0.10 (s), −0.16 (s), −0.18 (s).

Dimethylsilanediyl[2-methyl-4-(4'-tert-butylphenyl)-6-tert-butyl-inden-1-yl](2-methyl-4-phenyl-5-methoxy-6-tert-butyl-inden-1-yl)zirconium dichloride (CMC1))

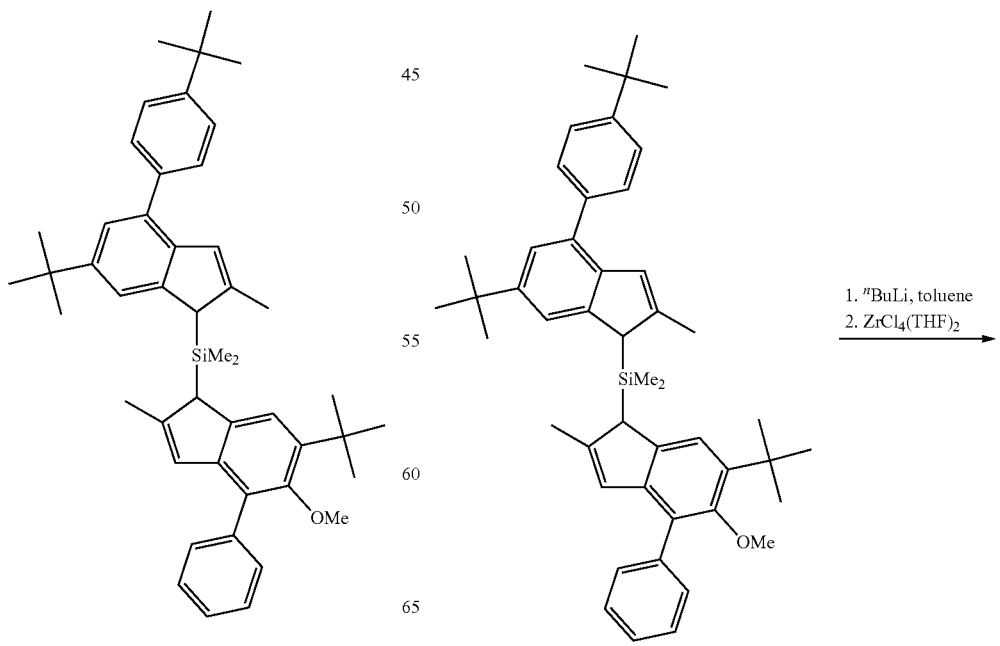

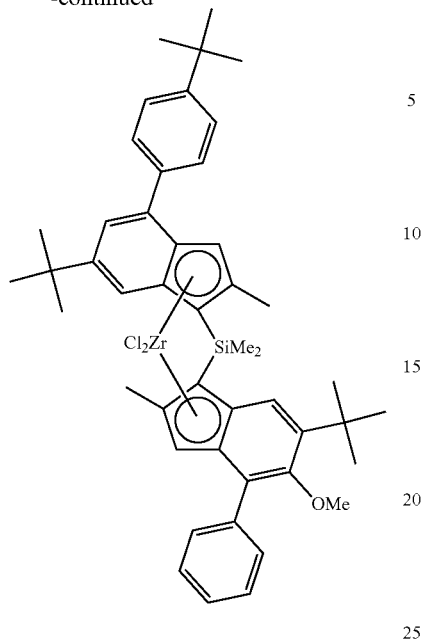

To a solution of 22.8 g (ca. 32.7 mmol) of [6-tert-butyl-4-(4'-tert-butylphenyl)-2-methyl-1H-inden-1-yl](6-tert-butyl-5-methoxy-2-methyl-4-phenyl-1H-inden-1-yl)dimethylsilane (of >90% purity as described above) in 300 ml of toluene 27.4 ml (68.5 mmol) of 2.5 M $^n$BuLi in hexanes was added in one portion. This mixture was stirred overnight at room temperature, then for 2 h at 80° C. The resulting orange-red solution was cooled to −20° C., and 12.9 g (34.2 mmol) of ZrCl$_4$(THF)$_2$ was added. The reaction mixture was stirred for 24 h, then 30 ml of THF was added, and the formed mixture was stirred at 80° C. for 3 h. After evaporation of 50 ml of the solvents, the resulting solution warmed to 80° C. was filtered through glass frit (G4), and the filtrate was evaporated to dryness. On the evidence of NMR spectroscopy, the residue is a ca. 60 to 40 mixture of anti- and syn-zirconocenes. Pure anti-zirconocene was obtained via crystallizations of this mixture from toluene-hexanes. This procedure gave 9.38 g (35%) of anti-zirconocene. Assignment in NMR spectra was made using the following abbreviations: L$^1$ for 6-tert-butyl-4-(4-tert-butylphenyl)-2-methyl-1H-inden-1-yl and L$^2$ for 6-tert-butyl-5-methoxy-2-methyl-4-phenyl-1H-inden-1-yl.

Anti-Zirconocene.

Anal. calc. for C$_{47}$H$_{56}$Cl$_2$OSiZr: C, 68.25; H, 6.82. Found: C, 68.45; H, 7.02.

$^1$H NMR (CDCl$_3$): δ 7.63-7.57 (m, 4H, 7-H in L$^1$, 7-H in L$^2$ and 2,6-H in Ph), 7.53 (d, J=6.5 Hz, 2H, 2,6-H in C$_6$H$_4$$^t$Bu), 7.48-7.46 (m, 3H, 3,5-H in C$_6$H$_4$$^t$Bu and 5-H in L$^1$), 7.43-7.39 (m, 2H, 3,5-H in Ph), 7.30 (t, J=7.3 Hz, 1H, 4-H in Ph), 6.95 (s, 1H, 3-H in L$^1$), 6.57 (s, 1H, 3-H in L$^2$), 3.39 (s, 3H, OMe), 2.23 (s, 3H, 2-Me in L$^1$), 2.19 (s, 3H, 2-Me in L$^2$), 1.39 (s, 9H, 6-$^t$Bu in L$_2$), 1.34 (s, 9H, $^t$Bu in C$_6$H$_4$$^t$Bu), 1.32 (s, 3H, SiMeMe'), 1.31 (s, 9H, 6-$^t$Bu in L$^1$), 1.31 (s, 3H, SiMeMe').

Synthesis of dimethylsilanediyl[2-methyl-4-(4'-tert-butylphenyl)-inden-1-yl][2-methyl-4-(3',5'-di-tert-butylphenyl)-5-methoxy-6-tert-butyl-inden-1-yl] zirconium dichloride (Complex CMC2—comparative)

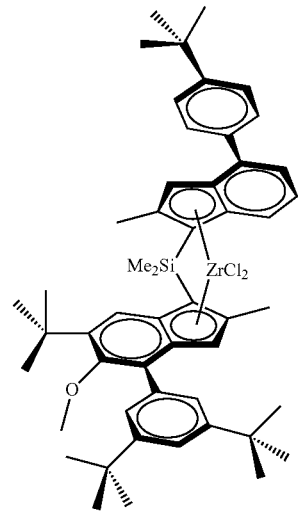

6-tert-Butyl-4-(3,5-di-tert-butylphenyl)-5-methoxy-2-methylindan-1-one

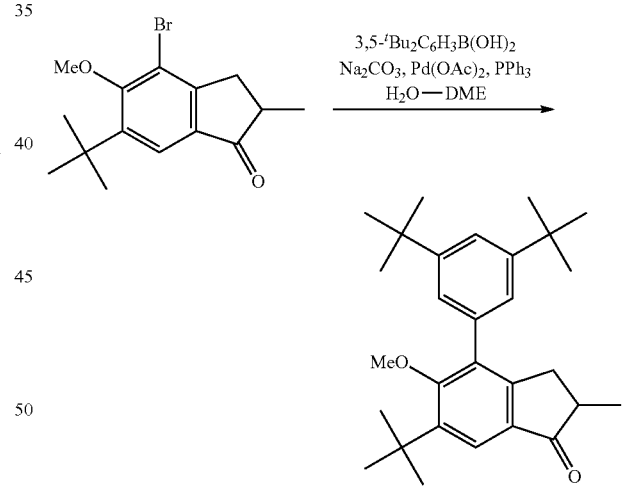

A mixture of 30.7 g (98.6 mmol) of 4-bromo-6-tertbutyl-5-methoxy-2-methylindanone, 30.6 g (128 mmol) 3,5-di-tert-butylphenylboronic acid, 29.7 g (280 mmol) of Na$_2$CO$_3$, 1.35 g (5.92 mmol; 6 mol. %) of Pd(OAc)$_2$, 3.15 g (11.8 mmol; 12 mol. %) of PPh$_3$, 130 ml of water, and 380 ml of 1,2-dimethoxyethane was refluxed for 12 h. Further on, the reaction mixture was quenched with water, solvents were evaporated. The residue was dissolved in 500 ml of dichloromethane, and this solution was washed by 500 ml of water. The organic layer was separated, the aqueous layer was additionally extracted with 100 ml of dichloromethane. The combined organic extract was dried over Na$_2$SO$_4$, then evaporated to dryness. The crude product isolated from the residue using flash chromatography on silica gel 60 (40-63 um, hexanes-dichloromethane=2:1, vol.) was then re-crystallized from n-hexane to give 18.5 g (43%) of a white solid.

Anal. calc. for $C_{29}H_{40}O_2$: C, 82.81; H, 9.59. Found: C, 83.04; H, 9.75.

$^1$H NMR (CDCl$_3$): δ 7.74 (s, 1H, 7-H in indan-1-one), 7.41 (t, J=1.6 Hz, 1H, 4-H in C$_6$H$_3$$^t$Bu$_2$), 7.24 (d, J=1.6 Hz, 2,6-H in C$_6$H$_3$$^t$Bu$_2$), 3.24 (s, 3H, OMe), 3.17 (dd, J=17.3 Hz, J=8.0 Hz, 1H, 3-H in indan-1-one), 2.64 (m, 1H, 2-H in indan-1-one), 2.47 (dd, J=17.3 Hz, J=3.7 Hz, 1H, 3-H' in indan-1-one), 1.43 (s, 9H, 6-$^t$Bu in indan-1-one), 1.36 (s, 18H, $^t$Bu in C$_6$H$_3$$^t$Bu$_2$), 1.25 (d, J=7.3 Hz, 3H, 2-Me in indan-1-one).

5-tert-Butyl-7-(3,5-di-tert-butylphenyl)-6-methoxy-2-methyl-1H-indene

Anal. calc. for $C_{29}H_{40}O$: C, 86.08; H, 9.96. Found: C, 86.26; H, 10.21.

$^1$H NMR (CDCl$_3$): δ 7.36 (t, J=1.8 Hz, 1H, 4H in C$_6$H$_3$$^t$Bu$_2$), 7.33 (d, J=1.8 Hz, 2H, 2,6-H in C$_6$H$_3$$^t$Bu$_2$), 7.21 (s, 1H, 4-H in indenyl), 6.44 (m, 1H, 3-H in indenyl), 3.17 (s, 3H, OMe), 3.14 (s, 2H, 1-H in indenyl), 2.06 (s, 3H, 2-Me in indenyl), 1.44 (s, 9H, 5-$^t$Bu in indenyl), 1.35 (s, 18H, $^t$Bu in C$_6$H$_3$$^t$Bu$_2$). $^{13}$C{$^1$H} NMR (CDCl$_3$): δ 150.4, 145.2 (two resonances), 141.7, 140.9, 140.6, 137.3, 132.5, 126.9, 124.0, 120.1, 116.9, 60.2, 43.0, 35.2, 34.9, 31.5, 31.0, 16.7.

[2-methyl-4-(3',5'-di-tert-butylphenyl)-6-tert-butyl-5-methoxy-1H-inden-1-yl]chlorodimethylsilane

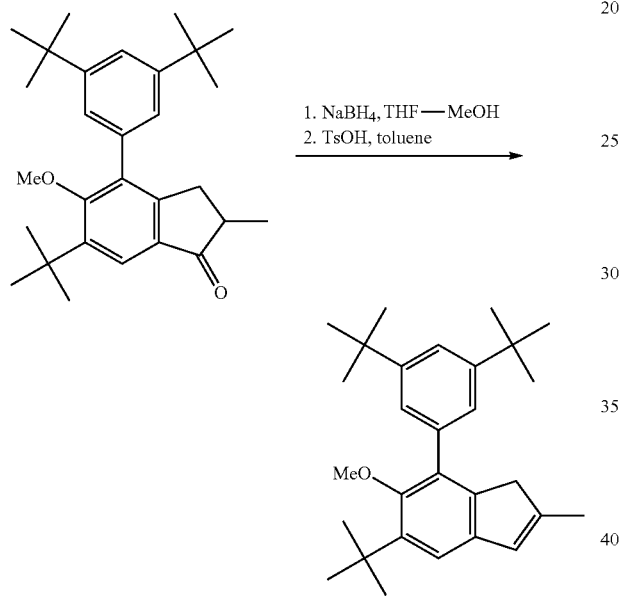
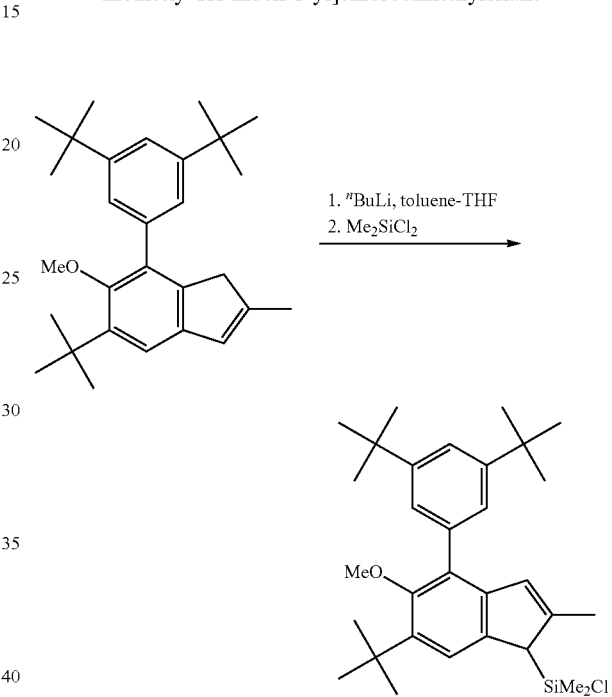

To a solution of 16.3 g (38.8 mmol) of 6-tert-butyl-4-(3,5-di-tert-butylphenyl)-5-methoxy-2-methylindan-1-one in 200 ml of THF cooled to 5° C. 1.47 g (38.9 mmol) of NaBH$_4$ was added. Further on, 80 ml of methanol was added dropwise to this mixture by vigorous stirring for ca. 7 h at 5° C. The resulting mixture was evaporated to dryness, and the residue was treated by 300 ml of dichloromethane and 300 ml of 2 M HCl. The organic layer was separated, the aqueous layer was additionally extracted with 100 ml of dichloromethane. The combined organic extract was evaporated to dryness to give a colorless oil. To a solution of this oil in 250 ml of toluene 0.1 g of TsOH was added, this mixture was refluxed with Dean-Stark head for 15 min and then cooled to room temperature using water bath. The resulting solution was washed by 10% aqueous Na$_2$CO$_3$. The organic layer was separated, the aqueous layer was extracted with 2×50 ml of dichloromethane. The combined organic extract was dried over K$_2$CO$_3$ and then passed through a short layer of silica gel 60 (40-63 um). The silica gel layer was additionally washed by 100 ml of dichloromethane. The combined organic elute was evaporated to dryness to give 15.7 g (99%) of a white crystalline product which was further used without an additional purification.

To a solution of 15.7 g (38.8 mmol) of 5-tert-butyl-7-(3, 5-di-tert-butylphenyl)-6-methoxy-2-methyl-1H-indene in 200 ml of toluene 16.0 ml (40.0 mmol) of 2.5 M $^n$BuLi in hexanes was added at room temperature. The resulting viscous solution was stirred for 10 h, and then 10 ml of THF was added. This mixture was stirred for 2 h at 60° C., then cooled to −20° C., and 25.0 g (194 mmol, 5 eq.) of dichlorodimethylsilane was added in one portion. The resulting solution was refluxed for 2 h, then evaporated to ca. ¾ of its volume, and filtered through glass frit (G3). The precipitate was additionally washed by 2×30 ml of toluene. The combined filtrate was evaporated to dryness to give 19.2 g (99%) of white solid which was further used without an additional purification.

Anal. calc. for $C_{31}H_{45}ClOSi$: C, 74.88; H, 9.12. Found: C, 75.12; H, 9.37.

$^1$H NMR (CDCl$_3$): δ 7.38 (s, 1H, 7-H in indenyl), 7.36 (t, J=1.6 Hz, 1H, 4-H in C$_6$H$_3$$^t$Bu$_2$), 7.33 (d, J=1.6 Hz, 2H, 2,6-H in C$_6$H$_3$$^t$Bu$_2$), 6.49 (m, 1H, 3-H in indenyl), 3.54 (s, 1H, 1-H in indenyl), 3.17 (s, 3H, OMe), 2.19 (s, 3H, 2-Me in indenyl), 1.44 (s, 9H, 6-$^t$Bu in indenyl), 1.36 (s, 18H, $^t$Bu in C$_6$H$_3$$^t$Bu$_2$), 0.45 (s, 3H, SiMeMe'), 0.18 (s, 3H, SiMeMe').

[6-tert-Butyl-4-(3,5-di-tert-butylphenyl)-5-methoxy-2-methyl-1H-inden-1-yl][4-(4-tert-butylphenyl)-2-methyl-1H-inden-1-yl]dimethylsilane

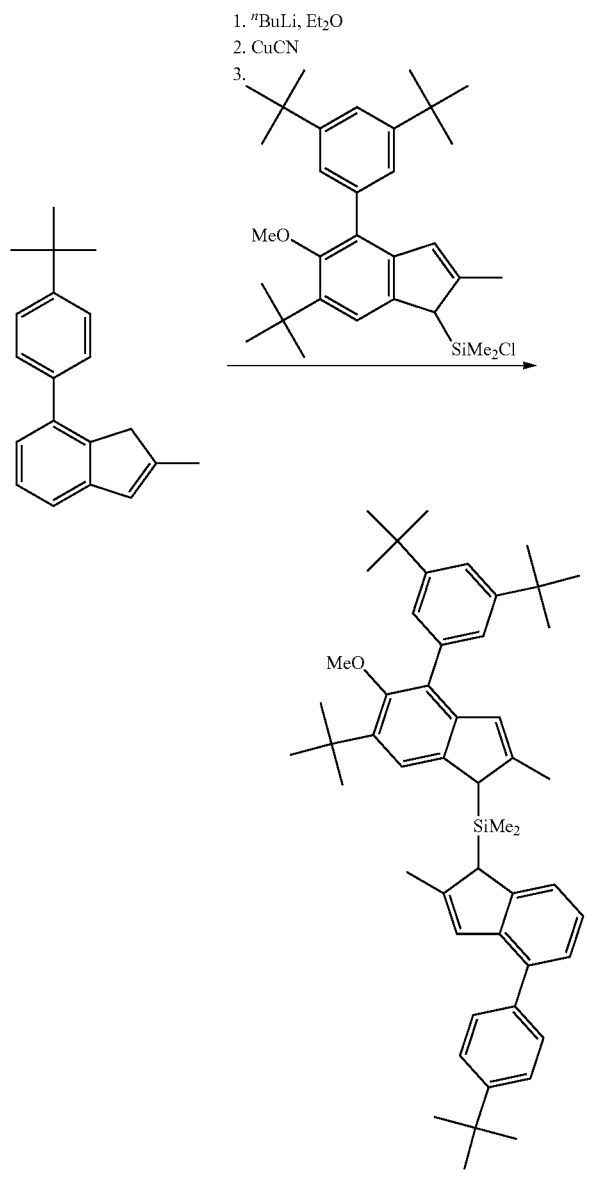

To a solution of 5.54 g (21.1 mmol) of 7-(4-tert-butylphenyl)-2-methyl-1H-indene in 150 ml of ether 8.50 ml (21.3 mmol) of 2.5 M $^n$BuLi in hexanes was added in one portion at −40° C. This mixture was stirred overnight at room temperature, then cooled to −40° C., and 190 mg of CuCN was added. The resulting mixture was stirred for 1 h at −20° C., then cooled to −40° C., and a solution of 10.5 g (21.1 mmol) of [6-tert-butyl-4-(3,5-di-tert-butylphenyl)-5-methoxy-2-methyl-1H-inden-1-yl](chloro)dimethylsilane in 150 ml of ether was added in one portion. Further on, this mixture was stirred overnight at ambient temperature, then 0.5 ml of water was added. This solution was filtered through a pad of silica gel 60 (40-63 um) which was additionally washed by 2×75 ml of dichloromethane. The combined elute was evaporated to dryness, and the residue was triturated with 70 ml of n-hexane. The obtained suspension was filtered on glass frit, the precipitate was washed with 30 ml of n-hexane and dried in vacuum to give a white powder. Additionally, the mother liquor was evaporated to small volume. The formed suspension was filtered through glass frit (G3), and the precipitate was washed with 2×15 ml of n-hexane and then dried in vacuum. Again, the mother liquor was evaporated to give a yellowish oil which was re-crystallized at −30° C. for two months. Crystals precipitated from this solution were collected and dried in vacuum. Thus, 12.2 g (80%) of the title product was isolated. Assignment in NMR spectra was made using the following abbreviations: $L^1$ for 4-(4-tert-butylphenyl)-2-methyl-1H-inden-1-yl and $L^2$ for 6-tert-butyl-4-(3,5-di-tert-butylphenyl)-5-methoxy-2-methyl-1H-inden-1-yl.

Anal. calc. for $C_{51}H_{66}OSi$: C, 84.70; H, 9.20. Found: C, 84.91; H, 9.35.

$^1$H NMR (CDCl$_3$): δ 7.48-7.46 (s, 5H, 2,6-H in $C_6H_4{}^tBu$ and 2,4,6-H in $C_6H_3{}^tBu_2$), 7.38 (s, 3H, 3,5-H in $C_6H_4{}^tBu$ and 7-H in $L^2$), 7.34 (d, J=7.5 Hz, 1H, 7-H in $L^1$), 7.24 (d, J=7.5 Hz, 1H, 5-H in $L^1$), 7.14 (t, J=7.5 Hz, 1H, 6-H in $L^1$), 6.80 (s, 1H, 3-H in $L^1$), 6.51 (s, 1H, 3-H in $L^2$), 3.71 (s, 1H, 1-H in $L^1$), 3.68 (s, 1H, 1-H in $L^2$), 3.20 (s, 3H, OMe), 2.18 (s, 3H, 2-Me in $L^1$), 2.13 (s, 3H, 2-Me in $L^2$), 1.44 (s, 9H, 6-$^t$Bu in $L^2$), 1.39 (s, 9H, $^t$Bu in $C_6H_4{}^tBu$), 1.38 (s, 18H, $^t$Bu in $C_6H_3{}^tBu_2$), −0.13 (s, 3H, SiMeMe'), −0.21 (s, 3H, SiMeMe').

Dimethylsilanediyl[2-methyl-4-(4-tert-butylphenyl)-inden-1-yl][2-methyl-4-(3,5-di-tert-butylphenyl)-5-methoxy-6-tert-butyl-inden-1-yl]zirconium dichloride (CMC2)

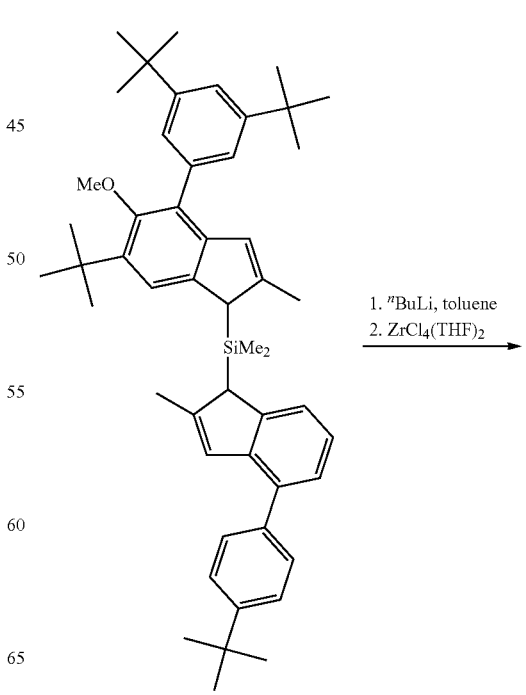

-continued

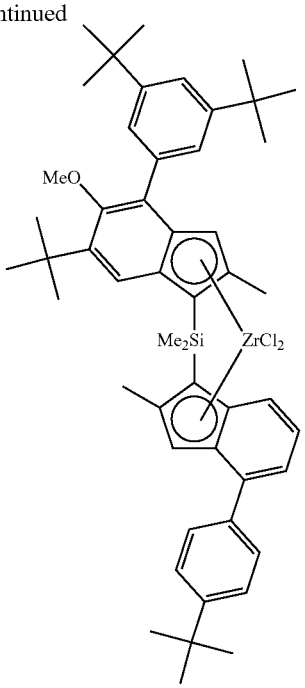

To a solution of 10.3 g (14.2 mmol) of [6-tert-butyl-4-(3,5-di-tert-butylphenyl)-5-methoxy-2-methyl-1H-inden-1-yl][4-(4-tert-butylphenyl)-2-methyl-1H-inden-1-yl]dimethylsilane in 200 ml of toluene (slightly warm solution was used because of low solubility of the starting bridging ligand) 11.4 ml (28.5 mmol) of 2.5 M $^n$BuLi in hexanes was added in one portion. This mixture was stirred overnight at room temperature, then for 2 h at 80° C. The resulting mixture was cooled to −20° C., and 5.37 g (14.2 mmol) of $ZrCl_4(THF)_2$ was added. This mixture was stirred for 24 h, then 20 ml of THF was added. The formed mixture was stirred for 3 h at 80° C. and then evaporated to ca. 150 ml. The resulting mixture was filtered through glass frit (G4) at 80° C. to give on the evidence of NMR spectroscopy a ca. 1 to 1 solution of anti- and syn-zirconocenes. This filtrate was then evaporated to ca. 10 ml, and then 100 ml of n-hexane was added. The formed orange precipitate was immediately filtered off on glass frit (G4), washed with 2×10 ml of n-hexane, and dried in vacuum. This procedure gave 2.10 g of syn-zirconocene contaminated with 2% of anti-isomer. The filtrate was evaporated to dryness, and the residue was re-crystallized from n-hexane. Crystals precipitated from this solution were collected and dried in vacuum to give 3.52 g of a ca. 1:1 mixture of syn- and anti-zirconocenes. Additionally, 1.46 g of a ca. 1:10 mixture of syn- and anti-zirconocenes precipitated after one week from the filtrate at room temperature. The latter product was re-crystallized from 25 ml of hot n-octane. Crystals precipitated at room temperature were collected and dried in vacuum to give 0.75 g of pure anti-zirconocene. The mother liquor was evaporated to 7 ml, then the residue was heated to dissolve the formed precipitate. Crystals precipitated from this solution at room temperature were collected and dried in vacuum to give 490 mg of anti-zirconocene contaminated with 8% of syn-isomer. Assignment in NMR spectra was made using the following abbreviations: $L^1$ for 4-(4-tert-butylphenyl)-2-methyl-1H-inden-1-yl and $L^2$ for 6-tert-butyl-4-(3,5-di-tert-butylphenyl)-5-methoxy-2-methyl-1H-inden-1-yl.

Anti-Zirconocene.

Anal. calc. for $C_{51}H_{64}Cl_2OSiZr$: C, 69.35; H, 7.30. Found: C, 69.54; H, 7.49.

$^1$H NMR (CDCl$_3$): δ 7.63-7.61 (m, 3H, 7-H in $L^1$ and 2,6-H in $C_6H_4{}^tBu$), 7.51 (s, 1H, 7-H in $L^2$), 7.47 (d, J=8.5 Hz, 2H, 3,5-H in $C_6H_4{}^tBu$), 7.44 (br. s, 2H, 2,6-H in $C_6H_3{}^tBu_2$), 7.37 (d, J=6.8 Hz, 1H, 5-H in $L^1$), 7.34 (t, J=1.6 Hz, 1H, 4-H in $C_6H_3{}^tBu_2$), 7.07 (dd, J=8.5 Hz, J=6.9 Hz, 1H, 6-H in $L^1$), 7.01 (s, 1H, 3-H in $L^1$), 6.62 (s, 1H, 3-H in $L^2$), 3.35 (s, 3H, OMe), 2.25 (s, 3H, 2-Me in $L^2$), 2.19 (s, 3H, 2-Me in $L^1$), 1.40 (s, 9H, 6-$^t$Bu in $L^2$), 1.34 (s, 9H, $^t$Bu in $C_6H_4{}^tBu$), 1.33-1.23 (m, $^t$Bu in $C_6H_3{}^tBu_2$, SiMeMe' and SiMeMe').

Syn-Zirconocene.

Anal. calc. for $C_{51}H_{64}Cl_2OSiZr$: C, 69.35; H, 7.30. Found: C, 69.33; H, 7.58.

$^1$H NMR (CDCl$_3$): δ 7.65 (d, 1H, J=8.6 Hz, 7-H in $L^1$), 7.57 (d, J=8.5 Hz, 2H, 2,6-H in $C_6H_4{}^tBu$), 7.52 (s, 1H, 7-H in $L^2$), 7.47 (d, J=8.5 Hz, 2H, 3,5-H in $C_6H_4{}^tBu$), 7.44 (br. s, 2H, 2,6-H in $C_6H_3{}^tBu_2$), 7.33 (t, J=1.6 Hz, 1H, 4-H in $C_6H_3{}^tBu_2$), 7.13 (d, J=6.8 Hz, 1H, 5-H in $L^1$), 6.90 (s, 1H, 3-H in $L^1$), 6.85 (dd, J=8.6 Hz, J=6.8 Hz, 1H, 6-H in $L^1$), 6.50 (s, 1H, 3-H in $L^2$), 3.14 (s, 3H, OMe), 2.44 (s, 3H, 2-Me in $L^2$), 2.38 (s, 3H, 2-Me in $L^1$), 1.44 (s, 3H, SiMeMe'), 1.35-1.33 (m, 36H, 6-$^t$Bu in $L^2$, $^t$Bu in $C_6H_4{}^tBu$ and $^t$Bu in $C_6H_3{}^tBu_2$), 1.22 (s, 3H, SiMeMe').

Inventive Metallocenes 1 and 2 (MC1 and MC2)

The novel metallocenes rac-dimethylsilanediyl(2-methyl-4-(4'-tert-butylphenyl)-6-methylinden-1-yl)(2-methyl-4-phenyl-5-methoxy-6-tert-butylinden-1-yl)zirconium dichloride (complex MC1) and rac-dimethylsilanediyl(2-methyl-4-(4'-tert-butylphenyl)-6-methylinden-1-yl)(2-methyl-4-(3',5'-ditertbutylphenyl)-5-methoxy-6-tert-butyl-inden-1-yl)zirconium dichloride (complex MC2) have been synthesized and isolated as follows:

Synthesis of dimethylsilanediyl[2,6-dimethyl-4-(4'-tert-butylphenyl)inden-1-yl][2-methyl-4-phenyl-5-methoxy-6-tert-butyl-inden-1-yl]zirconium dichloride (Complex MC1)

[2,6-dimethyl-4-(4'-tert-butylphenyl)-1H-inden-1-yl](2-methyl-4-phenyl-5-methoxy-6-tert-butyl-1H-inden-1-yl)dimethylsilane 1. $^n$BuLi, Et$_2$O
2. CuCN
3.

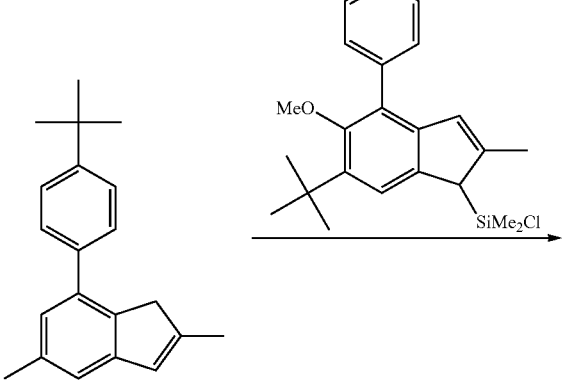

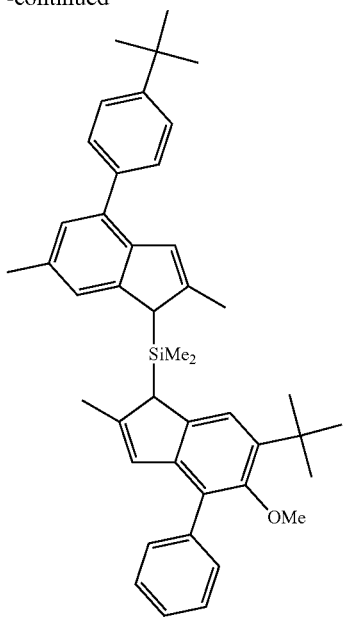

10.0 ml (25.0 mmol) of 2.5 M ⁿBuLi in hexanes was added in one portion at −40° C. to a solution of 6.92 g (25.0 mmol) of 2,5-dimethyl-7-(4'-tert-butylphenyl)-1H-indene in 150 ml of ether. This mixture was stirred overnight at room temperature, then cooled to −40° C., and 150 mg of CuCN was added. The resulting mixture was stirred for 1 h at −20° C., then cooled to −40° C., and a solution of 9.63 g (25.0 mmol) of (2-methyl-4-phenyl-5-methoxy-6-tert-butyl-1H-inden-1-yl)chlorodimethylsilane in 150 ml of ether was added in one portion. Further on, this mixture was stirred overnight at ambient temperature, then 0.5 ml of water was added. The resulting solution was filtered through a pad of silica gel 60 (40-63 μm) which was additionally washed by 3×30 ml of dichloromethane. The combined organic elute was evaporated to dryness, and the residue was dried in vacuum. This procedure gave 16.2 g (94%) of the title product (of ca. 90% purity as a ca. 60:40 mixture of the stereoisomers on the evidence of NMR spectroscopy) which was further used without additional purification.

Anal. calc. for $C_{44}H_{52}OSi$: C, 84.56; H, 8.39. Found: C, 84.85; H, 8.58.

$^1$H NMR (CDCl$_3$): δ 7.53-7.42 (m), 7.37-7.32 (m), 7.20 (s), 7.15 (s), 7.09 (s), 6.79 (s), 6.74 (s), 6.46 (s), 6.43 (s), 3.69 (s), 3.67 (s), 3.65 (s), 3.63 (s), 3.25 (s), 3.23 (s), 2.40 (s), 2.18 (s), 2.10 (s), 2.06 (s), 1.44 (s), 1.42 (s), 1.39 (s), 1.38 (s), −0.10 (s), −0.16 (s), −0.18 (s), −0.19 (s).

Dimethylsilanediyl[2,6-dimethyl-4-(4'-tert-butylphenyl)inden-1-yl](2-methyl-4-phenyl-5-methoxy-6-tert-butylinden-1-yl]-zirconium dichloride (MC1)

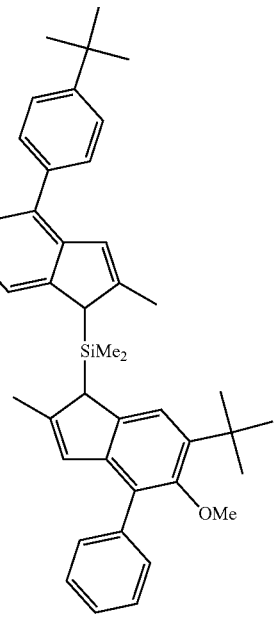

1. ⁿBuLi, Et$_2$O
2. ZrCl$_4$

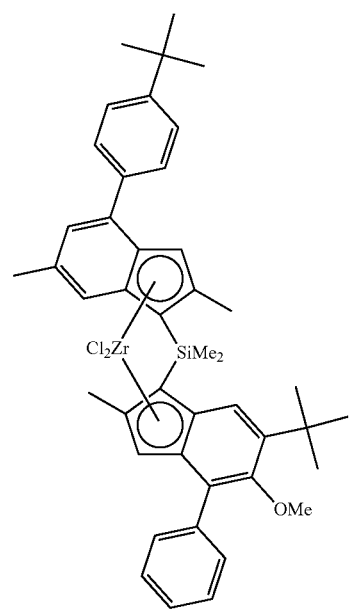

20.0 ml (50.0 mmol) of 2.5 M ⁿBuLi in hexanes was added in one portion to a solution of 16.2 g (ca. 25.0 mmol) of (2-methyl-4-phenyl-5-methoxy-6-tert-butyl-1H-inden-1-yl)[2,6-dimethyl-4-(4'-tert-butylphenyl)-1H-inden-1-yl]dimethylsilane (prepared as described above) in 200 ml of ether cooled to −30° C. This mixture was stirred overnight at room temperature, then cooled to −50° C., and 5.83 g (25.0 mmol) of ZrCl$_4$ was added. The reaction mixture was stirred for 24 h and then evaporated to dryness. The residue was dissolved in 200 ml of warm toluene, and the resulting suspension was filtered through glass frit (G4) giving a solution which on the evidence of NMR spectroscopy includes a ca. 65 to 35 mixture of anti- and syn-zirconocenes. The filtrate was evaporated to 110 ml. Crystals precipitated at room temperature were collected, washed with 2×5 ml of a mixture of toluene and n-hexane (ca. 1:1, vol.), then 10 ml of n-hexane, and dried in vacuum. This procedure gave 0.97 g of anti-zirconocene contaminated with 2% of syn-isomer. The mother liquor was evaporated to 70 ml. Crystals precipitated at room temperature were collected, washed with 3×5 ml of toluene, then 10 ml of n-hexane, and dried in vacuum. This procedure gave 4.75 g of anti-zirconocene contaminated with 2% of syn-isomer. Thus, the total yield of the target anti-zirconocene was 5.72 g (29%). The mother liquor was evaporated to 30 ml. Crystals precipitated at room temperature were collected, washed with 2×5 ml of toluene, then 5 ml of n-hexane, and dried in vacuum. This procedure gave 4.40 g (22%) of syn-zirconocene contaminated with 4% of anti-isomer. The mother liquors was evaporated to dryness, and 20 ml of n-hexane was added. Crystals precipitated at room temperature were collected and dried in vacuum. This procedure gave 2.87 g of a ca. 4:3 mixture of anti- and syn-zirconocenes. Thus, the total yield of all zirconocenes isolated in this synthesis was 13.0 g (66%). Assignment in NMR spectra was made using the following abbreviations: $L^1$ for 2,6-dimethyl-4-(4'-tert-butylphenyl)-1H-inden-1-yl and $L^2$ for 2-methyl-4-phenyl-5-methoxy-6-tert-butyl-1H-inden-1-yl.

Anti-Zirconocene.

Anal. calc. for $C_{44}H_{50}Cl_2OSiZr$: C, 67.31; H, 6.42. Found: C, 67.43; H, 6.44.

$^1$H NMR (CDCl$_3$): δ 7.62-7.60 (m, 4H, 2,6-H in C$_6$H$_4$$^t$Bu and 2,6-H in Ph), 7.53 (s, 1H, 7-H in L$^2$), 7.47-7.40 (m, 4H, 3,5-H in C$_6$H$_4$$^t$Bu and 3,5-H in Ph), 7.37 (s, 1H, 7-H in L$^1$), 7.32 (t, J=7.4 Hz, 1H, 4-H in Ph), 7.24 (s, 1H, 5-H in L$^1$), 7.96 (s, 1H, 3-H in L$^1$), 6.58 (s, 1H, 3-H in L$^2$), 3.39 (s, 3H, OMe), 2.36 (s, 3H, 6-Me in L$^1$), 2.23 (s, 3H, 2-Me in L$^1$), 2.18 (s, 3H, 2-Me in L$^2$), 1.39 (s, 9H, $^t$Bu in C$_6$H$_4$$^t$Bu), 1.33 (s, 9H, 6-$^t$Bu in L$^2$), 1.32 (s, 3H, SiMeMe'), 1.30 (s, 3H, SiMeMe').

Syn-Zirconocene.

Anal. calc. for $C_{44}H_{50}Cl_2OSiZr$: C, 67.31; H, 6.42. Found: C, 67.39; H, 6.62.

$^1$H NMR (CDCl$_3$): δ 7.60-7.58 (m, 4H, 2,6-H in C$_6$H$_4$$^t$Bu and 2,6-H in Ph), 7.55 (s, 1H, 7-H in L$^2$), 7.48-7.41 (m, 4H, 3,5-H in C$_6$H$_4$$^t$Bu and 3,5-H in Ph), 7.38 (s, 1H, 7-H in L$^1$), 7.32 (t, J=7.4 Hz, 1H, 4-H in Ph), 7.04 (s, 1H, 5-H in L$^1$), 7.90 (s, 1H, 3-H in L$^1$), 6.50 (s, 1H, 3-H in L$^2$), 3.22 (s, 3H, OMe), 2.43 (s, 3H, 6-Me in L$^1$), 2.38 (s, 3H, 2-Me in L$^1$), 2.32 (s, 3H, 2-Me in L$^2$), 1.46 (s, 3H, SiMeMe'), 1.36 (s, 9H, $^t$Bu in C$_6$H$_4$$^t$Bu), 1.34 (s, 9H, 6-$^t$Bu in L$^2$), 1.22 (s, 3H, SiMeMe').

rac-dimethylsilanediyl(2,6-dimethyl-4-(4'-tert-butylphenyl)inden-1-yl)(2-methyl-4-(3',5'-di-tert-butylphenyl)-5-methoxy-6-tert-butyl-inden-1-yl)zirconium dichloride (complex MC2)

[2-methyl-4-(3',5'-di-tert-butylphenyl)-5-methoxy-6-tert-butyl-1H-inden-1-yl]chlorodimethylsilane was synthesized as described for CMC2.

[2,6-dimethyl-4-(4'-tert-butylphenyl)-1H-inden-1-yl] [2-methyl-4-(3',5'-di-tert-butylphenyl)-5-methoxy-6-tert-butyl-1H-inden-1-yl]dimethylsilane

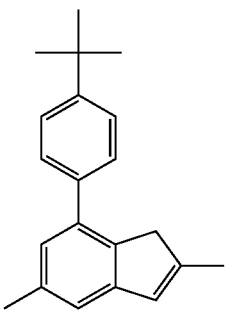

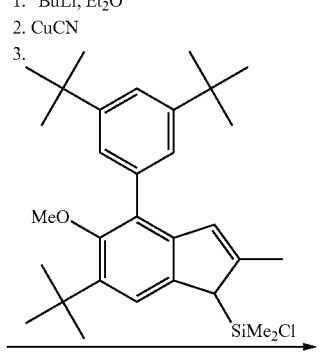

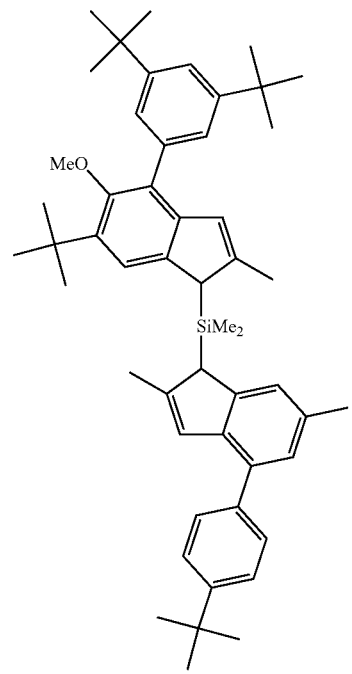

7.0 ml (17.5 mmol) of 2.5 M $^n$BuLi in hexanes was added in one portion at −40° C. to a solution of 4.81 g (17.4 mmol) of 2,5-dimethyl-7-(4'-tert-butylphenyl)-1H-indene in 150 ml of ether. This mixture was stirred overnight at room temperature, then cooled to −40° C., and 150 mg of CuCN was added. The resulting mixture was stirred for 1 h at −20° C., then cooled to −40° C., and a solution of 8.65 g (17.4 mmol) of [2-methyl-4-(3',5'-di-tert-butylphenyl)-5-methoxy-6-tert-butyl-1H-inden-1-yl](chloro)dimethylsilane in 150 ml of ether was added in one portion. Further on, this mixture was stirred overnight at ambient temperature, then 0.5 ml of water was added. This solution was filtered through a pad of silica gel 60 (40-63 μm) which was additionally washed by 3×30 ml of dichloromethane. The combined organic elute was evaporated to dryness, and the residue was dried in vacuum. This procedure gave 13.0 g (86%) of [2-methyl-4-(3',5'-di-tert-butylphenyl)-5-methoxy-6-tert-butyl-1H-inden-1-yl][2,6-dimethyl-4-(4'-tert-butylphenyl)-1H-inden-1-yl]dimethylsilane (of ca. 85% purity as a ca. 55:45 mixture of the stereoisomers on the evidence of NMR spectroscopy) which was further used without additional purification.

Anal. calc. for $C_{52}H_{68}OSi$: C, 84.72; H, 9.30. Found: C, 85.07; H, 9.66.

$^1$H NMR (CDCl$_3$): δ 7.49-7.44 (m), 7.38-7.34 (m), 7.20 (s), 7.16 (s), 7.09 (s), 6.79 (s), 6.76 (s), 6.51 (s), 3.70-3.66 (m), 3.20 (s), 3.19 (s), 2.40 (s), 2.40 (s), 2.21 (s), 2.19 (s), 2.17 (s), 2.14 (s), 1.44 (s), 1.42 (s), 1.38-1.37 (m), −0.14 (s), −0.16 (s), −0.19 (s), −0.22 (s).

Dimethylsilanediyl[η$^5$-6-tert-butyl-4-(3,5-di-tert-butylphenyl)-5-methoxy-2-methylinden-1-yl][η$^5$-4-(4-tert-butylphenyl)-2,6-dimethylinden-1-yl]zirconium dichloride (MC2)

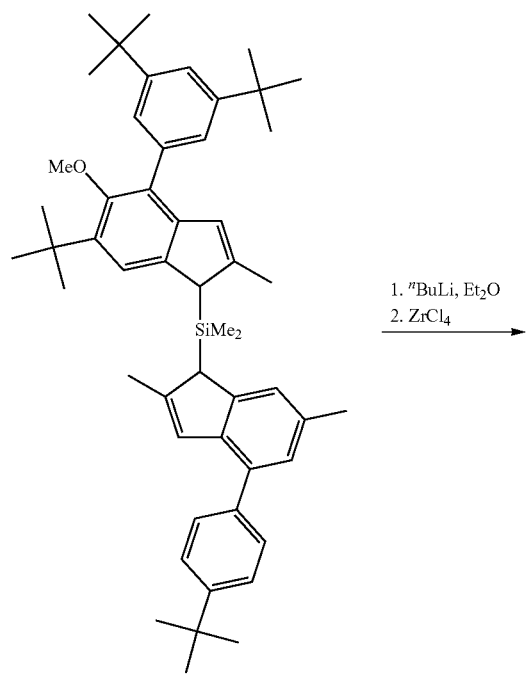

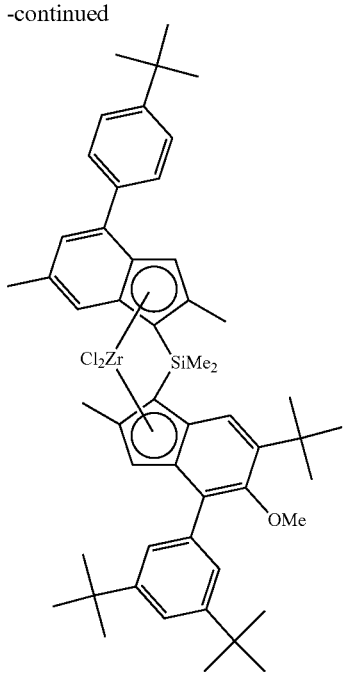

14.0 ml (35.0 mmol) of 2.5 M $^n$BuLi in hexanes was added in one portion to a solution of 13.0 g (ca. 17.4 mmol) of [2-methyl-4-(3',5'-di-tert-butylphenyl)-5-methoxy-6-tert-butyl-1H-inden-1-yl][2,6-dimethyl-4-(4'-tert-butylphenyl)-1H-inden-1-yl]dimethylsilane (prepared as described above) in 200 ml of ether cooled to −30° C. This mixture was stirred overnight at room temperature, then cooled to −50° C., and 4.06 g (17.4 mmol) of ZrCl$_4$ was added. The reaction mixture was stirred for 24 h and then evaporated to dryness. The residue was dissolved in 100 ml of warm toluene, and the resulting suspension was filtered through glass frit (G4) to form a solution which on the evidence of NMR spectroscopy includes a ca. 55 to 45 mixture of anti- and syn-zirconocenes. The filtrate was evaporated to 30 ml, and 30 ml of n-hexane was added. Crystals precipitated at room temperature were collected, washed by 2×10 ml of a mixture of toluene-n-hexane (1:2, vol.), then 10 ml of n-hexane, and dried in vacuum. This procedure gave 2.97 g of syn-zirconocene contaminated with 4% of anti-isomer. The mother liquor was evaporated to dryness, and 40 ml of n-hexane was added. Crystals precipitated from this solution at room temperature after 3 h were collected, washed by 2×5 ml of n-hexane, and dried in vacuum. This procedure gave 0.30 g of syn-zirconocene contaminated with 8% of anti-isomer. Crystals precipitated from the mother liquor overnight at room temperature were collected, washed by 2×5 ml of cold n-hexane, and dried in vacuum. This procedure gave 2.95 g (19%) of anti-isomer. The mother liquor was evaporated to dryness, and 20 ml of n-hexane were added to the residue. Crystals precipitated from this solution at room temperature were collected and dried in vacuum. This procedure gave 3.32 g of a ca. 6:5 mixture of anti- and syn-zirconocenes. Thus, the total yield of all zirconocenes isolated in this synthesis was 9.54 g (61%). Assignment in NMR spectra was made using the following abbreviations: L$^1$ for 2,6-dimethyl-4-(4'-tert-butylphenyl)-1H-inden-1-yl and L$^2$ for 2-methyl-4-(3',5'-di-tert-butylphenyl)-5-methoxy-6-tert-butyl-1H-inden-1-yl.

Anti-Zirconocene.

Anal. calc. for $C_{52}H_{66}Cl_2OSiZr$: C, 69.60; H, 7.41. Found: C, 69.82; H, 7.49.

$^1$H NMR (CDCl$_3$): δ 7.61 (d, J=8.4 Hz, 2H, 2,6-H in $C_6H_4{}^tBu$), 7.55 (br. s, 2H, 2,6-H in $C_6H_3{}^tBu_2$), 7.50 (s, 1H, 7-H in L$^2$), 7.46 (d, J=8.4 Hz, 2H, 3,5-H in $C_6H_4{}^tBu$), 7.37 (s, 1H, 7-H in L$^1$), 7.35 (m, 1H, 4-H in $C_6H_3{}^tBu_2$), 7.22 (s, 1H, 5-H in L$^1$), 6.95 (s, 1H, 3-H in L$^1$), 6.62 (s, 1H, 3-H in L$^2$), 3.35 (s, 3H, OMe), 2.35 (s, 3H, 6-Me in L$^1$), 2.23 (s, 3H, 2-Me in L$^1$), 2.19 (s, 3H, 2-Me in L$^2$), 1.40 (s, 9H, 6-$^t$Bu in L$^2$), 1.34 (s, 9H, $^t$Bu in $C_6H_4{}^tBu$), 1.32 (s, 18H, $^t$Bu in $C_6H_3{}^tBu_2$), 1.30 (s, 3H, SiMeMe'), 1.29 (s, 3H, SiMeMe').

Syn-Zirconocene.

Anal. calc. for $C_{52}H_{66}Cl_2OSiZr$: C, 69.60; H, 7.41. Found: C, 69.84; H, 7.62.

$^1$H NMR (CDCl$_3$): δ 7.58 (d, J=8.3 Hz, 2H, 2,6-H in $C_6H_4{}^tBu$), 7.55 (br. s, 2H, 2,6-H in $C_6H_3{}^tBu_2$), 7.52 (s, 1H, 7-H in L$^2$), 7.47 (d, J=8.3 Hz, 2H, 3,5-H in $C_6H_4{}^tBu$), 7.37 (s, 1H, 7-H in L$^1$), 7.35 (s, 1H, 4-H in $C_6H_3{}^tBu_2$), 7.01 (s, 1H, 5-H in L$^1$), 6.87 (s, 1H, 3-H in L$^1$), 6.52 (s, 1H, 3-H in L$^2$), 3.15 (s, 3H, OMe), 2.43 (s, 3H, 6-Me in L$^1$), 2.39 (s, 3H, 2-Me in L$^1$), 2.31 (s, 3H, 2-Me in L$^2$), 1.45 (s, 3H, SiMeMe'), 1.36-1.34 (m, 36H, $^t$Bu in $C_6H_4{}^tBu$, $^t$Bu in $C_6H_3{}^tBu_2$ and 6-$^t$Bu in L$^2$), 1.22 (s, 3H, SiMeMe').

Synthesis of anti-dimethylsilylene(2-methyl-4-phenyl-5-methoxy-6-tert-butyl-indenyl)(2-methyl-4-(4-tert-butyl-phenyl)indenyl)zirconium dichloride (Metallocene CMC3)

4/7-(4-tert-Butylphenyl)-2-methyl-3/1H-indene

To a solution of 4-tert-butylphenylmagnesium bromide obtained from 110 g (0.518 mol) of 1-bromo-4-tert-butyl-benzene and 12.6 g (0.518 mol) of magnesium turnings in 500 ml of THF, 0.65 g (0.83 mmol) (IPr)NiCl$_2$PPh$_3$ and a solution of 77.6 g (0.371 mol) of 4/7-bromo-2-methyl-3/1H-indene in 50 ml of THF were added. This mixture was stirred at reflux for 30 min, and then for 20 min at room temperature. Finally, 150 ml of water and then 70 ml of 4 M HCl were added. The product was extracted with 200 ml of ether and then 2×100 ml of dichloromethane. The combined organic extract was dried over K$_2$CO$_3$, passed through a short column with Silica Gel 60, and evaporated to dryness. Rectification of the residue, b.p. 163-171° C./5 mm Hg, gave 93.8 g (96%) of a mixture of the title isomeric indenes as yellowish viscous oil which is slowly crystallized.

Anal. calc. for $C_{20}H_{22}$: C, 91.55; H, 8.45. Found: C, 91.62; H, 8.52.

$^1$H NMR (CDCl$_3$): δ 7.62 (m, $C_6H_4$ of both isomers), 7.46 (m, 5- and 6-H in 4- and 7-arylindenes), 7.40 (m, 7- and 4-H in 4- and 7-arylindenes), 7.31 (m, 6- and 5-H in 4- and 7-arylindenes), 6.88 (m, 3-H in 4/7-arylindene), 6.68 (m, 3-H in 7/4-arylindene), 3.55 (m, 1-CH$_2$ in 7/4-arylindene), 3.49 (m, 1-CH$_2$ in 4/7-arylindene), 2.28 (2-Me in 4/7-arylindene), 2.27 (2-Me in 7/4-arylindene), 1.54 (s, $^t$Bu in 4- and 7-arylindenes).

(6-tert-Butyl-5-methoxy-2-methyl-4-phenyl-1H-inden-1-yl)[4-(4-tert-butylphenyl)-2-methyl-1H-inden-1-yl]dimethylsilane

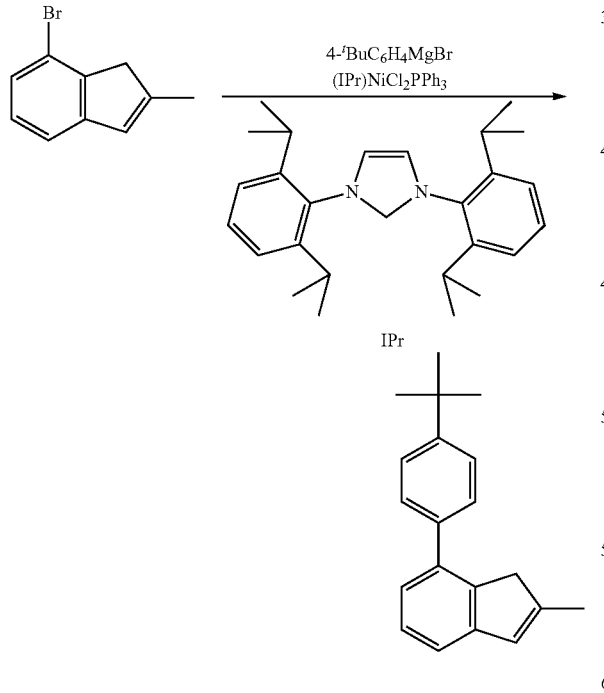

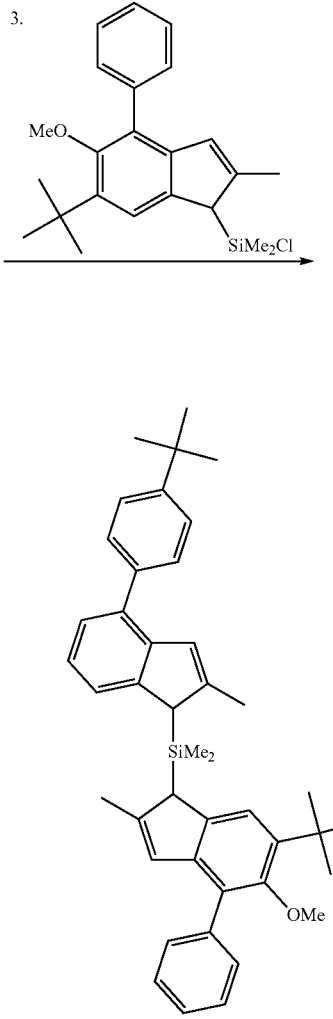

To a solution of 11.5 g (43.8 mmol) of 7-(4-tert-butyl-phenyl)-2-methyl-1H-indene in 300 ml of ether, 17.0 ml (42.5 mmol) of 2.5 M "BuLi in hexanes was added in one portion at −78° C. This mixture was stirred overnight at room temperature, then cooled to −60° C., and 150 mg of CuCN was added. The resulting mixture was stirred for 1 h at −20° C., then cooled to −70° C., and 16.2 g of (6-tert-butyl-5-methoxy-2-methyl-4-phenyl-1H-inden-1-yl)(chloro)-dimethylsilane (42.08 mmol) in 150 ml of ether was added. Further on, this mixture was stirred overnight at ambient temperature, then 0.5 ml of water was added. This solution was filtered through a pad of silica gel 60 (40-63 um) which was additionally washed by dichloromethane. The combined organic elute was evaporated to dryness, and the obtained yellowish oil was purified by flash chromatography on silica gel 60 (40-63 um; eluent: hexane-dichloromethane, from 10:1 to 3:1, vol.). This procedure gave 23.4 g (91%) of the title compound as yellowish glass.

Anal. Calcd. for $C_{43}H_{50}OSi$: C, 84.54; H, 8.25%. Found: C, 84.70; H, 8.33%.

$^1$H NMR (CDCl$_3$): δ 7.59-7.18 (m), 6.89 (m), 6.83 (m), 6.51 (m), 6.48 (m), 3.77 (m), 3.73 (m), 3.68-3.70 (m), 3.31 (s), 3.29 (s), 2.25 (s), 2.23 (s), 2.16 (s), 2.10 (s), 1.50 (s), 1.48 (s), 1.45 (s), 1.44 (s), 0.00 (s), −0.09 (s), −0.11 (s), −0.12 (s).

Anti- and syn-dimethylsilylene(2-methyl-4-phenyl-5-methoxy-6-tert-butyl-indenyl)(2-methyl-4-(4-tert-butyl-phenyl)indenyl)zirconium dichloride

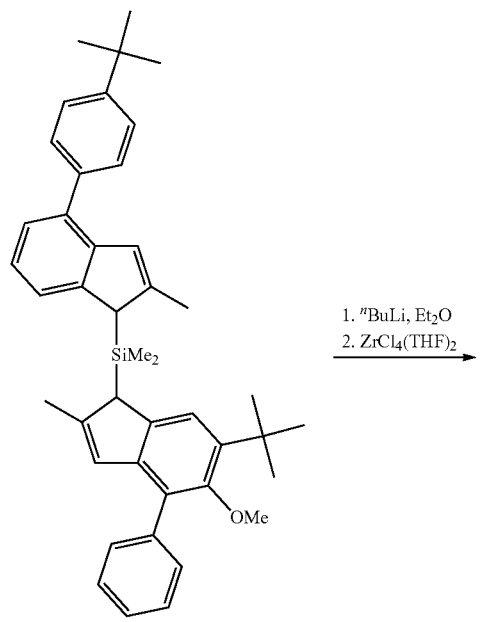

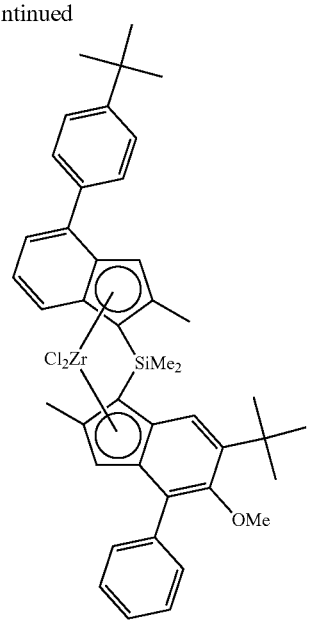

To a solution of 15.3 g (25.0 mmol) of (6-tert-butyl-5-methoxy-2-methyl-4-phenyl-1H-inden-1-yl)[4-(4-tert-butylphenyl)-2-methyl-1H-inden-1-yl]dimethylsilane in 300 ml of ether cooled to −78° C., 20.0 ml (50.0 mmol) of 2.5 M "BuLi in hexanes was added in one portion. This mixture was stirred overnight at room temperature, then cooled to −60° C., and 9.43 g (25.0 mmol) of ZrCl$_4$(THF)$_2$ was added. The resulting mixture was stirred for 24 h (a light orange solution with a significant amount of precipitate was formed), then evaporated to dryness, and 350 ml of toluene was added. The resulting solution warmed to 80° C. was filtered through glass frit (G4) to form on the evidence of NMR spectroscopy a ca. 1 to 1 mixture of anti- and syn-zirconocenes. Crystals precipitated overnight from this solution at room temperature were collected, washed by 2×10 ml of cold toluene, and dried in vacuum. This procedure gave 3.50 g of pure syn-zirconocene as a light-orange microcrystalline powder. The mother liquor was evaporated to ca. 100 ml. Crystals precipitated overnight from this solution at room temperature were collected, washed with 10 ml of cold toluene, and dried in vacuum. This procedure gave additional amount (4.10 g) of pure syn-zirconocene. Thus, the combined yield of pure syn-zirconocene was 7.60 g (39%) as a light-orange microcrystalline powder. Crystals precipitated after 3 days at room temperature were collected, washed by 10 ml of cold toluene, and dried in vacuum. This procedure gave 2.95 g of pure anti-zirconocene as a slightly orange microcrystalline powder. Additional amount of this product was obtained in a similar manner from mother liquor evaporated to ca. 35 ml. Thus, the combined yield of anti-zirconocene was 5.65 g (29%).

Anti-|CMC3

Anal. Calcd. for $C_{43}H_{48}Cl_2OSiZr$: C, 66.98; H, 6.27%. Found: C, 67.00; H, 6.31%.

¹H NMR (CDCl₃): δ 7.61-7.63 (m, 3H, 2,6-H in C₆H₄ and 5-H in indenyl of I), 7.54 (s, 1H, 7-H in indenyl of II), 7.46-7.48 (m, 2H, 3,5-H in C₆H₄ of I), 7.42 (m, 2H, 3,5-H in Ph of II), 7.37 (d, J=7.1 Hz, 1H, 7-H in indenyl of I), 7.32 (m, 1H, 4-H in Ph of II), 7.09 (dd, J=8.6 Hz, J=7.1 Hz, 1H, 6-H in indenyl of I), 7.02 (s, 1H, 3-H in indenyl of II), 6.57 (s, 1H, 3-H in indenyl of I), 3.39 (s, 3H, OMe), 2.25 (s, 3H, 2-Me in I), 2.17 (s, 3H, 2-Me in II), 1.39 (s, 9H, 6-$^t$Bu in II), 1.33 (s, 9H, 4-$^t$Bu in I), 1.31 (s, 6H, SiMe₂); where I is 4-(4-tert-butylphenyl)-2-methyl-1H-inden-1-yl, II-6-tert-butyl-5-methoxy-2-methyl-4-phenyl-1H-inden-1-yl.

syn-CMC3

Anal. Found: C, 66.12; H, 6.35%.

¹H NMR (CDCl₃): δ 7.64 (m, 1H, 5-H in indenyl of I), 7.56-7.58 (m, 2H, 2,6-H in C₆H₄ of I), 7.54 (s, 1H, 7-H in indenyl of II), 7.44-7.46 (m, 2H, 3,5-H in C₆H₄ of I), 7.41 (m, 2H, 3,5-H in Ph of II), 7.30 (m, 1H, 4-H in Ph of II), 7.15 (d, J=7.1 Hz, 1H, 7-H in indenyl of I), 6.91 (s, 1H, 3-H in indenyl of II), 6.87 (dd, J=8.6 Hz, J=7.1 Hz, 1H, 6-H in indenyl of I), 6.47 (s, 1H, 3-H in indenyl of I), 3.20 (s, 3H, OMe), 2.44 (s, 3H, 2-Me in I), 2.37 (s, 3H, 2-Me in II), 1.44 (s, 3H, SiMeMe'), 1.34 (s, 9H, 6-$^t$Bu in II), 1.33 (s, 9H, 4-$^t$Bu in I), 1.22 (s, 3H, SiMeMe'); where I is 4-(4-tert-butylphenyl)-2-methyl-1H-inden-1-yl, II-6-tert-butyl-5-methoxy-2-methyl-4-phenyl-1H-inden-1-yl.

Catalyst Synthesis—Inventive Catalyst 1—E1

Inside the glovebox, 80 μL of dry and degassed surfactant solution were mixed with 2 mL of MAO in a septum bottle and left to react overnight. The following day, 59.8 mg of the metallocene MC1 (0,076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.37 g of a red powder was obtained.

Inventive Catalyst 2—E2

Inside the glovebox, 80 μL of dry and degassed surfactant solution were mixed with 2 mL of MAO in a septum bottle and left to react overnight. The following day, 68.35 mg of the metallocene MC2 (0,076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.41 g of a red powder was obtained.

Comparison Catalyst CE3

Inside the glovebox, 80 μL of dry and degassed surfactant solution were mixed with 2 mL of MAO in a septum bottle and left to react overnight. The following day, 58.69 mg of the metallocene CMC3 (0,076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.52 g of a red powder was obtained.

Comparison Catalyst CE1

Inside the glovebox, 80 μL of dry and degassed surfactant solution were mixed with 2 mL of MAO in a septum bottle and left to react overnight. The following day, 62.86 mg of the metallocene CMC1 (0,076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.42 g of a red powder was obtained.

Comparison Catalyst CE2

Inside the glovebox, 80 µL of dry and degassed surfactant solution were mixed with 2 mL of MAO in a septum bottle and left to react overnight. The following day, 67.13 mg of the metallocene CMC2 (0,076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.49 g of a red powder was obtained.

TABLE 3

ICP analysis of un-prepped catalysts

| Catalyst name | Zr (%) | Al (%) | Al/Zr (molar) |
|---|---|---|---|
| E1 | 26.4 | 0.37 | 241 |
| E2 | 26.6 | 0.34 | 264 |
| CE3 | 18.9 | 0.24 | 266 |
| CE1 | 23.9 | 0.32 | 252 |
| CE2 | 28.3 | 0.34 | 281 |

Polymerisations
Homopolymerisation

The polymerisations were performed in a 5 L reactor. 200 µl of triethylaluminum was fed as a scavenger in 5 mL of dry and degassed pentane. The desired amount of hydrogen was then loaded (measured in mmol) and 1100 g of liquid propylene was fed into the reactor.

The temperature was set to 20° C. The desired amount of catalyst (5 to 30 mg) in 5 mL of PFC is flushed into the reactor with a nitrogen overpressure. After 5 minutes of the temperature is raised to 70° C. over a period of 15 minutes. The polymerisation is stopped after 60 minutes by venting the reactor and flushing with nitrogen before the polymer is collected.

The catalyst activity was calculated on the basis of the 60 minutes period according to the following formula:

$$\text{Catalyst Activity (kg}/g_{cat}/h) = \frac{\text{amount of polymer produced (kg)}}{\text{catalyst loading (g)} \times \text{polymerisation time (h)}}$$

TABLE 4

Homopolymerization results

| Catalyst | Test # | Cat. (mg) | Time min | $H_2$ mmol | Pol. Yield, g | Act cat kg/g/h | $MFR_2$ (*) or $MFR_{21}$ g/10 min. | $M_w$ kg/mol | $M_w/M_n$ | $T_m$ (° C.) | $T_c$ (° C.) |
|---|---|---|---|---|---|---|---|---|---|---|---|
| CE3 | 1 | 9.4 | 60 | 1.0 | 114 | 12.1 | 4.6 | 857 | 2.6 | 147.1 | 105.8 |
|  | 2 | 10.0 | 60 | 6.0 | 298 | 29.8 | 31.0 | 486 | 2.3 | 146.9 | 107.9 |
|  | 3 | 10.0 | 60 | 15.0 | 389 | 38.9 | 3.2* | 264 | 2.5 | 148.8 | 108.3 |
| CE1 | 4 | 10.9 | 60 | 1.0 | 250 | 22.9 | 4.4 | 753 | 2.5 | 143.6 | 103.6 |
|  | 5 | 10.3 | 60 | 6.0 | 424 | 41.1 | 56.0 | 389 | 2.5 | 143.8 | 105.2 |
|  | 6 | 6.1 | 60 | 15.0 | 279 | 45.7 | 9.4* | 217 | 2.5 | 143.8 | 106.6 |
| CE2 | 7 | 12.7 | 60 | 1.0 | 209 | 16.4 | 5.4 | 711 | 2.7 | 151.5 | 109.1 |
|  | 8 | 10.0 | 60 | 6.0 | 309 | 30.9 | 43.0 | 418 | 2.7 | 151.6 | 110.5 |
|  | 9 | 10.0 | 60 | 15.0 | 410 | 41.0 | 5.0* | 270 | 2.6 | 152.3 | 110.9 |
| E1 | 10 | 10.3 | 60 | 1.0 | 340 | 33.0 | 3.0 | 847 | 2.3 | 147.1 | 107.2 |
|  | 11 | 9.1 | 60 | 6.0 | 530 | 58.3 | 39.0 | 441 | 2.1 | 147.7 | 107.9 |
|  | 12 | 5.8 | 60 | 15.0 | 368 | 63.5 | 0.81* | 405 | 2.3 | 148.5 | 107.0 |
| E2 | 13 | 10.2 | 60 | 1.0 | 352 | 34.5 | 4.1 | 813 | 2.3 | 151.6 | 109.4 |
|  | 14 | 8.7 | 60 | 6.0 | 512 | 58.9 | 38.0 | 464 | 2.3 | 151.8 | 109.4 |
|  | 15 | 5.8 | 60 | 15.0 | 406 | 69.9 | 6.6* | 237 | 2.6. | 152.8 | 110.9 |

*$MFR_2$ (g/10 min)

Random Polymerisation

The polymerisations were performed in a 5 L reactor. 200 μl of triethylaluminum was fed as a scavenger in 5 mL of dry and degassed pentane. The desired amount of hydrogen (6 mmol) was then loaded (measured in mmol) and 1100 g of liquid propylene was fed into the reactor. The desired amount of ethylene was fed to the reactor.

The temperature was set to 30° C. The desired amount of catalyst (5 to 30 mg) in 5 mL of PFC is flushed into the reactor with a nitrogen overpressure. The temperature is then raised to 70° C. over a period of 15 minutes. The polymerisation is stopped after 30 minutes by venting the reactor and flushing with nitrogen before the polymer is collected.

The catalyst activity was calculated on the basis of the 30 minutes period according to the following formula:

$$\text{Catalyst Activity (kg/} g_{cat}/\text{h)} = \frac{\text{amount of polymer produced (kg)}}{\text{catalyst loading (g)} \times \text{polymerisation time (h)}}$$

TABLE 5

$C_3/C_2$ random copolymerisation results

| Catalyst | Test # | Cat. (mg) | Time (min) | $C_2$ Feed (g) | Pol. Yield, (g) | A cat (kg/g/h) | $MFR_{21}$ (g/10 min) | $M_w$ (kg/mol) | $M_w/M_n$ | NMR $C_2$ (wt.-%) | $T_m$ (° C.) | $T_c$ (° C.) |
|---|---|---|---|---|---|---|---|---|---|---|---|---|
| CE3 | 16 | 5.1 | 30 | 19.9 | 149 | 58.5 | 18.0 | 538 | 2.4 | 1.44 | 135.2 | 98.7 |
|  | 17 | 10.0 | 30 | 40.2 | 193 | 38.6 | 19.0 | 516 | 2.4 | 3.34 | 124.2 | 88.2 |
|  | 18 | 15.0 | 30 | 49.9 | 236 | 31.4 | 21.0 | 504 | 2.6 | 3.58 | 119.3 | 83.1 |
| CE1 | 19 | 5.6 | 30 | 20.0 | 210 | 74.9 | 42.0 | 441 | 2.3 | 1.61 | 132.0 | 95.5 |
|  | 20 | 9.4 | 30 | 40.0 | 177 | 37.6 | 51.0 | 430 | 2.5 | 3.31 | 120.9 | 85.4 |
|  | 21 | 8.2 | 30 | 50.0 | 150 | 36.5 | 36.0 | 462 | 2.4 | 3.88 | 115.7 | 79.7 |
| CE2 | 22 | 8.9 | 30 | 20.0 | 280 | 63.0 | 41.0 | 466 | 2.3 | 1.41 | 139.0 | 99.5 |
|  | 23 | 8.9 | 30 | 40.0 | 203 | 45.5 | 40.0 | 471 | 2.6 | 2.86 | 127.3 | 89.5 |
|  | 24 | 9.7 | 30 | 49.9 | 173 | 35.6 | 41.0 | 458 | 2.6 | 3.63 | 121.3 | 83.6 |
| E1 | 25 | 8.7 | 30 | 19.9 | 424 | 97.5 | 38.0 | 448 | 2.3 | 1.35 | 135.6 | 97.2 |
|  | 26 | 8.1 | 30 | 39.9 | 258 | 63.6 | 27.0 | 475 | 2.4 | 3.23 | 123.7 | 86.9 |
| E2 | 27 | 8.2 | 30 | 19.9 | 408 | 99.4 | 46.0 | 437 | 2.4 | 1.52 | 138.5 | 100.0 |
|  | 28 | 8.3 | 30 | 39.9 | 280 | 67.5 | 52.0 | 420 | 2.5 | 3.23 | 126.2 | 88.5 |

TABLE 6

Summary of the bench evaluation results for the novel MC- complexes, compared to their analogues comparative complexes

| MC complex | CE3 | E1 | CE1 |
|---|---|---|---|
| Activity (PP-h)* ($kg_{pol}/g_{cat}$/h) | 30 | 58 | 41 |
| $T_m$** (° C.) | 149 | 147 | 144 |
| $M_w$ capability*** (kg/mol) | Excellent (994) | Excellent (847) | Good (753) |
| $MFR_{21}$ (1 mmol H2) | 1.6 | 3.0 | 4.4 |

TABLE 6-continued

Summary of the bench evaluation results for the novel MC- complexes, compared to their analogues comparative complexes

| | | |
|---|---|---|
| Stereoregularity | High | High |
| (mmmm %) | (99.4) | (99.7) |
| Regioregularity | Low | Low |
| (2,1e %) | (1.2) | (1.2) |
| MW depression in $C_2/C_3$ copol. | modest | None |
| $C_3/C_2$ Activity**** ($kg_{pol}/g_{cat}/h$) | 58 | 97.5 |

(third column values for above section: High (99.7); Low (1.7); none; 74.9)

| | CE2 | E2 |
|---|---|---|
| MC complex | 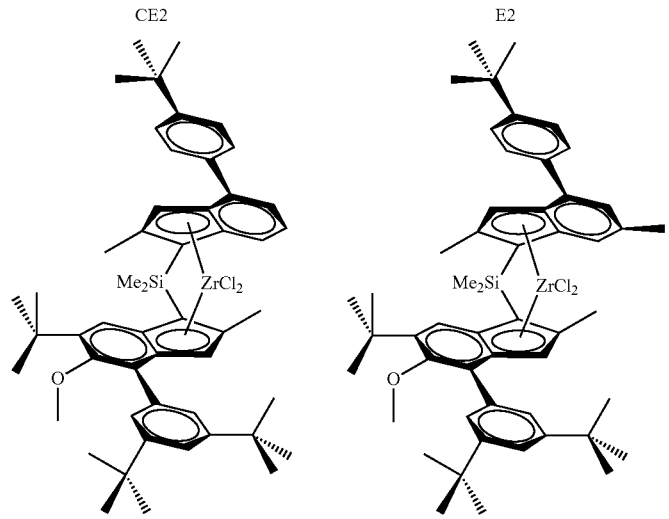 | |
| Activity (PP-h)* ($kg_{pol}/g_{cat}/h$) | 31 | 59 |
| $T_m$** (° C.) | 152 | 152 |
| $M_w$ capability*** | Good | Excellent |
| (kg/mol) | (711) | (813) |
| $MFR_{21}$ (1 mmol H2) | 5.4 | 4.1 |
| Stereoregularity | High | High |
| (mmmm %) | (99.5) | (99.5) |
| Regioregularity | Low | Low |
| (2,1e %) | (0.9) | (0.8) |
| MW depression in $C_2/C_3$ copol. | none | none |
| $C_3/C_2$ Activity**** ($kg_{pol}/g_{cat}/h$) | 63.0 | 99.4 |

*6 mmol (0.016 mol-%) $H_2$, 60 min. polymerisation, Average from 3 runs, *1 mmol (0.009 mol-%) $H_2$, 60 min. polymerisation, ****20 g $C_2$, 30 min. polymerisation As shown in Table 6, the catalysts of the invention show an excellent balance between catalyst activity, PP molecular weight and PP melting temperature. In particular, inventive catalyst E1 is much more active than comparative catalysts CE3 or CE1, and inventive catalyst E2 is more active compared to CE2. E2 in particular combines the best performance, having high activity and producing PP with the relatively high melting temperature of 152° C.

The invention claimed is:

1. An asymmetric complex of formula (I)

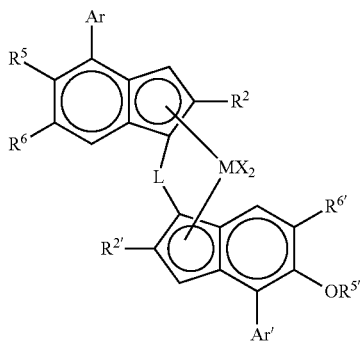

wherein
M is zirconium or hafnium;
each X is a sigma ligand;
L is a divalent bridge selected from the group consisting of —R'$_2$C—, —R'$_2$C—CR'$_2$—, —R'$_2$Ge—, wherein each R' is independently a hydrogen atom, C1-C20-alkyl, tri(C1-C20-alkyl)silyl, C6-C20-aryl, C7-C20-arylalkyl and C7-C20-alkylaryl;
$R^2$ and $R^{2'}$ are each independently a $C_1$-$C_{20}$ hydrocarbyl radical;
$R^{5'}$ is a $C_{1-20}$ hydrocarbyl group;
$R^5$ is hydrogen, or a $C_{1-20}$ hydrocarbyl group;
$R^6$ is a non tertiary $C_{1-10}$ alkyl group or C6-10-aryl group or C7-10 arylalkyl group or $ZR^3$;
Z is O or S;
$R^{6'}$ is a tertiary $C_{4-20}$ alkyl group;
$R^3$ is a C1-20 hydrocarbyl group optionally substituted with halo;
Ar is an aryl or heteroaryl group having up to 20 carbon atoms optionally substituted by one or more groups $R^1$;
Ar' is an aryl or heteroaryl group having up to 20 carbon atoms optionally substituted by one or more groups $R^1$;
each $R^1$ is a $C_{1-20}$ hydrocarbyl group or two $R^1$ groups on adjacent carbon atoms taken together can form a fused 5 or 6 membered ring with the Ar group, said ring being itself optionally substituted with one or more groups $R^4$; and
each $R^4$ is a $C_{1-20}$ hydrocarbyl group.

2. A complex as claimed in claim 1 being a racemic anti isomer.

3. A complex as claimed in claim 1 wherein Ar and Ar' are different.

4. A complex as claimed in claim 1 wherein $R^2$ and $R^{2'}$ are methyl.

5. A complex as claimed in claim 1 wherein $R^5$ is H and/or wherein $R^{5'}$ is methoxy.

6. A complex as claimed in claim 1 wherein $R^6$ is methyl and/or $R^{6'}$ is tBu.

7. A complex as claimed in claim 1 being of formula (II):

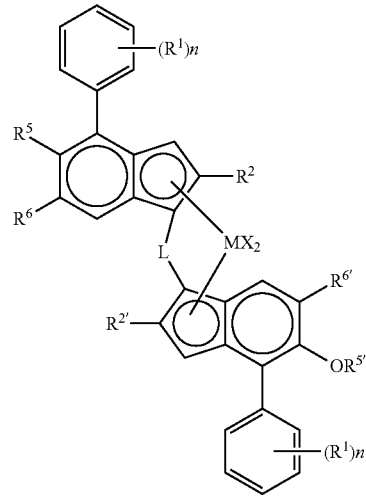

wherein
M is zirconium or hafnium;
each X is independently a hydrogen atom, a halogen atom, $C_{1-6}$ alkoxy group, $C_{1-6}$ alkyl, phenyl or benzyl group;
L is a divalent bridge selected from the group consisting of —R'$_2$C—, —R'$_2$C—CR'$_2$—, —R'$_2$Ge—, wherein each R' is independently a hydrogen atom, $C_{1-20}$ alkyl, $C_{3-10}$ cycloalkyl, $C_{6-20}$-aryl, $C_{7-20}$ arylalkyl and $C_{7-20}$ alkylaryl;
$R^2$ and $R^{2'}$ are each independently a $C_1$-$C_{10}$ alkyl radical;
$R^{5'}$ is a $C_{1-6}$ alkyl group;
$R^5$ is hydrogen, or a $C_{1-10}$ alkyl group;
$R^6$ is a non tertiary $C_{1-6}$ alkyl, C6-10 aryl group or C7-10 arylalkyl group;
$R^{6'}$ is a tertiary $C_{4-10}$ alkyl group;
each n is independently 0 to 3;
and each $R^1$ is independently a $C_{1-10}$ alkyl group.

8. A complex as claimed in claim 1 of formula (III):

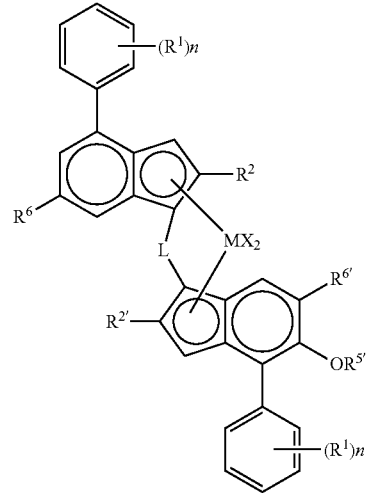

wherein

M is zirconium or hafnium;

each X is independently a hydrogen atom, a halogen atom, $C_{1-6}$ alkoxy group, $C_{1-6}$ alkyl, phenyl or benzyl group;

L is a divalent bridge selected from the group consisting of —R'$_2$C— or —R'$_2$Si— wherein each R' is independently a hydrogen atom, $C_{1-20}$ alkyl and $C_{3-10}$ cycloalkyl;

$R^2$ and $R^{2'}$ are each independently a $C_{1-6}$ alkyl radical;

$R^{5'}$ is a $C_{1-6}$ alkyl group;

$R^6$ is a non tertiary $C_{1-6}$ alkyl;

$R^{6'}$ is a tertiary $C_{4-8}$ alkyl group;

each n is independently 0 to 3;

and each $R^1$ is independently a $C_{1-10}$ alkyl group.

9. A complex as claimed in claim 1 of formula (IV):

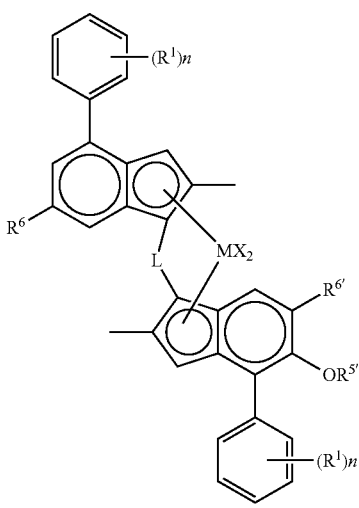

M is zirconium or hafnium;

each X is independently a hydrogen atom, a halogen atom, $C_{1-6}$-alkoxy group, $C_{1-6}$-alkyl, phenyl or benzyl group;

L is a divalent bridge selected from the group consisting of —R'$_2$C— or —R'$_2$Si— wherein each R' is independently a hydrogen atom, $C_{1-20}$ alkyl and $C_{3-10}$ cycloalkyl;

$R^{5'}$ is a $C_{1-6}$ alkyl group;

$R^6$ is a $C_{1-3}$ alkyl;

$R^{6'}$ is a tertiary $C_{4-8}$ alkyl group;

each n is independently 0 to 2;

and each $R^1$ is independently a $C_{3-8}$ alkyl group.

10. A complex as claimed in claim 1 of formula (V):

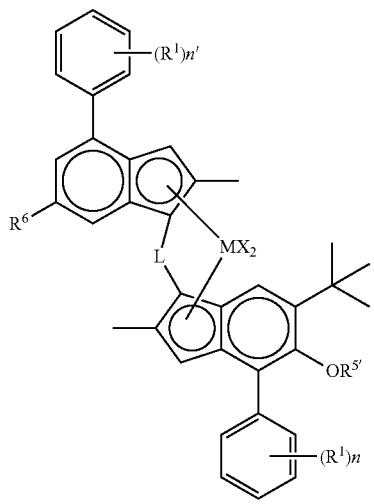

wherein each X is independently a hydrogen atom, a halogen atom, $C_{1-6}$-alkoxy group, $C_{1-6}$-alkyl, phenyl or benzyl group;

L is -Me$_2$Si—;

$R^5$ is a $C_{1-6}$ alkyl group;

$R^6$ is a $C_{1-3}$ alkyl;

n' is 1 to 2;

n is 0 to 2;

and each $R^1$ is independently a $C_{3-8}$ alkyl group.

11. A catalyst comprising (i) an asymmetric complex of formula (I) as claimed in claim 1 and (ii) a cocatalyst comprising a compound of a group 13 metal.

12. A catalyst as claimed in claim 11 obtained by a process in which
   (a) a liquid/liquid emulsion system is formed, said liquid/liquid emulsion system comprising a solution of the catalyst components (i) and (ii) dispersed in a solvent so as to form dispersed droplets; and
   (b) solid particles are formed by solidifying said dispersed droplets.

13. A process for the manufacture of a catalyst as claimed in claim 11 comprising contacting a complex of formula (I) and a cocatalyst as hereinbefore described;
   forming a liquid/liquid emulsion system, which comprises a solution of catalyst components (i) and (ii) dispersed in a solvent, and solidifying said dispersed droplets to form solid particles.

14. A process for the polymerisation of at least one olefin comprising reacting said at least one olefin with a catalyst as claimed in claim 11.

* * * * *